(12) United States Patent
Zwierstra et al.

(10) Patent No.: US 10,555,861 B2
(45) Date of Patent: Feb. 11, 2020

(54) DYNAMIC HEADSET APPARATUS

(71) Applicant: Neural Analytics, Inc., Los Angeles, CA (US)

(72) Inventors: Jan Zwierstra, Los Angeles, CA (US); Trevor Dunlop, Los Angeles, CA (US); Lane Stith, Los Angeles, CA (US)

(73) Assignee: Neural Analytics, Inc., Los Angeles, CA (US)

( * ) Notice: Subject to any disclaimer, the term of this patent is extended or adjusted under 35 U.S.C. 154(b) by 5 days.

(21) Appl. No.: 16/101,352

(22) Filed: Aug. 10, 2018

(65) Prior Publication Data

US 2019/0045868 A1 Feb. 14, 2019

Related U.S. Application Data

(60) Provisional application No. 62/544,347, filed on Aug. 11, 2017.

(51) Int. Cl.
*A61G 13/12* (2006.01)
*A47G 9/10* (2006.01)
*A47C 7/38* (2006.01)

(52) U.S. Cl.
CPC .............. *A61G 13/121* (2013.01); *A47C 7/38* (2013.01); *A47C 7/383* (2013.01); *A47G 9/10* (2013.01); *A47G 9/1009* (2013.01)

(58) Field of Classification Search
CPC ................ A47G 9/10; A47G 9/1009; A47G 2009/1018; A47G 9/1081; A47G 9/109; A47C 7/38; A47C 7/383; A61G 7/065; A61G 7/075; A61G 13/1205; A61G 13/121

USPC .... 5/622, 621, 636, 637, 640, 643, 632, 630
See application file for complete search history.

(56) References Cited

U.S. PATENT DOCUMENTS

| | | | |
|---|---|---|---|
| 4,465,069 A | 8/1984 | Barbier et al. | |
| 5,879,281 A | 3/1999 | Ein-Gal | |
| 6,198,961 B1 | 3/2001 | Stern et al. | |
| 9,498,290 B2 * | 11/2016 | Piferi | A61N 1/0534 |
| 10,213,184 B2 * | 2/2019 | Rincker | A61B 8/0808 |
| 2015/0031982 A1 | 1/2015 | Piferi et al. | |
| 2015/0297176 A1 | 10/2015 | Rincker et al. | |
| 2018/0235824 A1 * | 8/2018 | Nordgren | A61B 90/14 |
| 2019/0045868 A1 * | 2/2019 | Zwierstra | A42B 3/0473 |
| 2019/0082098 A1 * | 3/2019 | Costa | A61B 8/4209 |

FOREIGN PATENT DOCUMENTS

FR 1514314 A 2/1968
WO WO-03/005922 A1 1/2003

OTHER PUBLICATIONS

International Search Report and Written Opinion dated Dec. 17, 2018, from application No. PCT/US2018/046372.
Partial International Search Report dated Oct. 12, 2018, from application No. PCT/US2018/046372.

* cited by examiner

*Primary Examiner* — Robert G Santos
(74) *Attorney, Agent, or Firm* — Foley & Lardner LLP

(57) ABSTRACT

A dynamic headset system is provided. The dynamic headset system includes a head cradle configured to receive a head of a subject and having a bottom surface configured to face a platform on which the dynamic headset apparatus is placed. The dynamic headset system further includes a device including an instrument adjacent to the head of the subject when the head of the subject is in the head cradle.

26 Claims, 49 Drawing Sheets

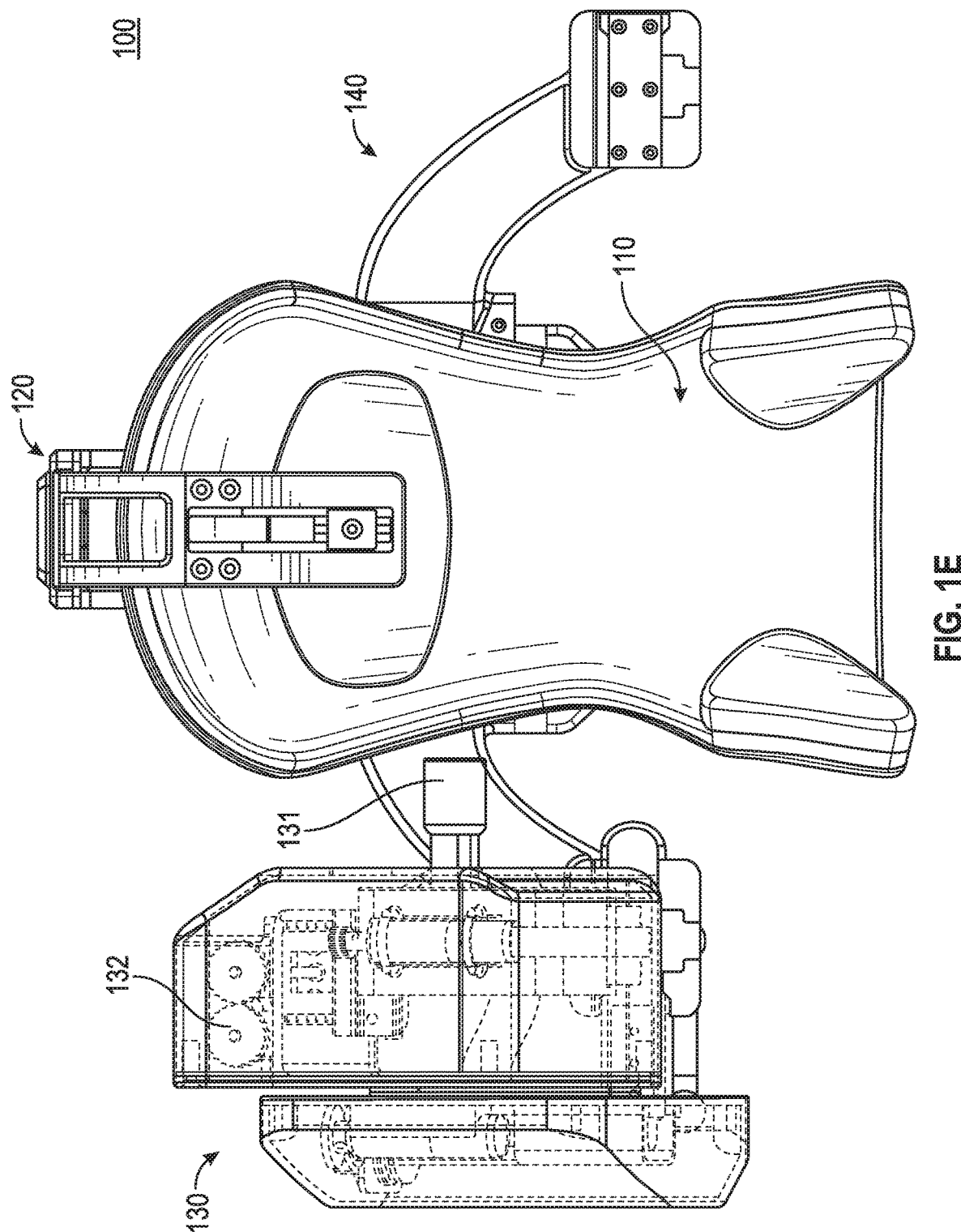

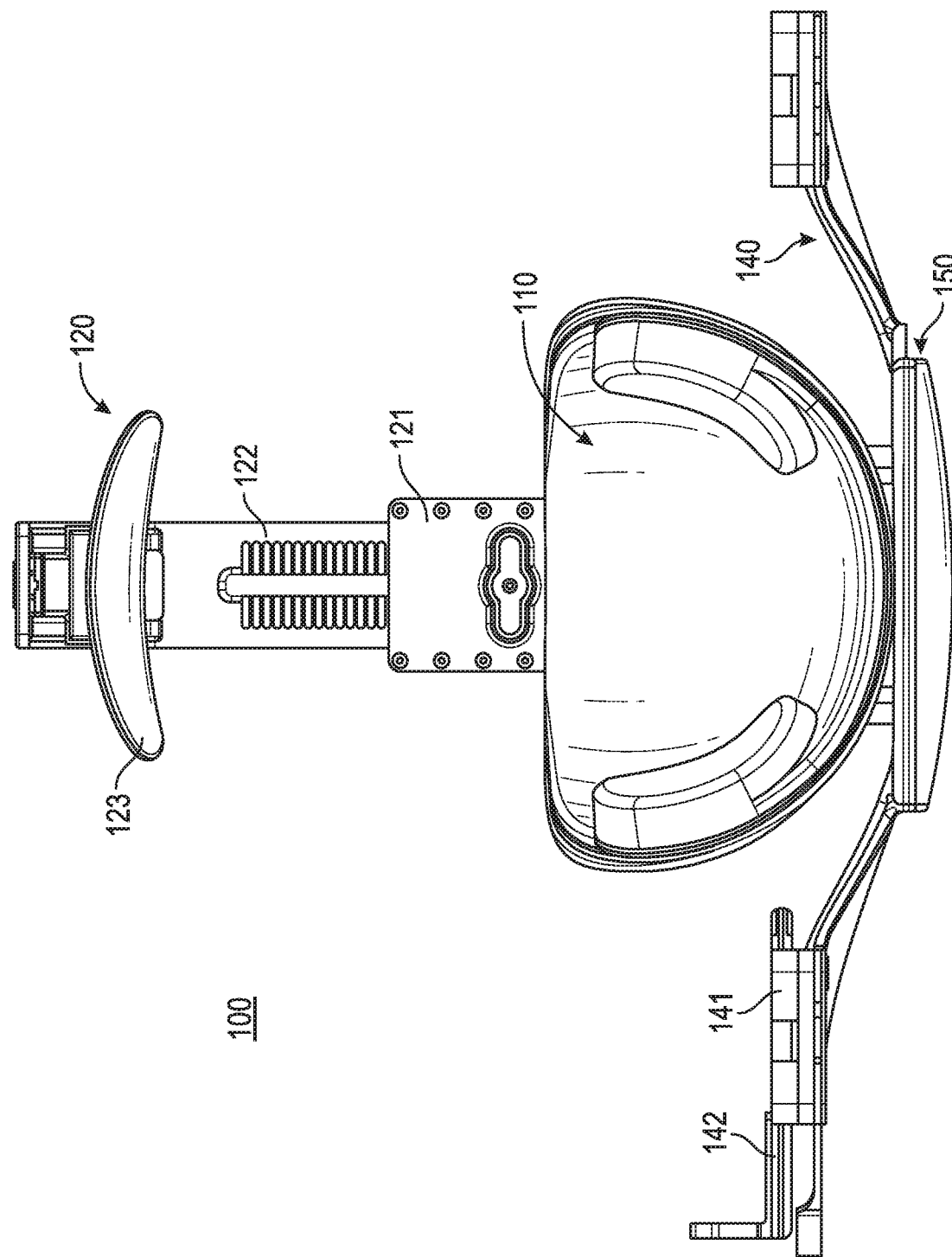

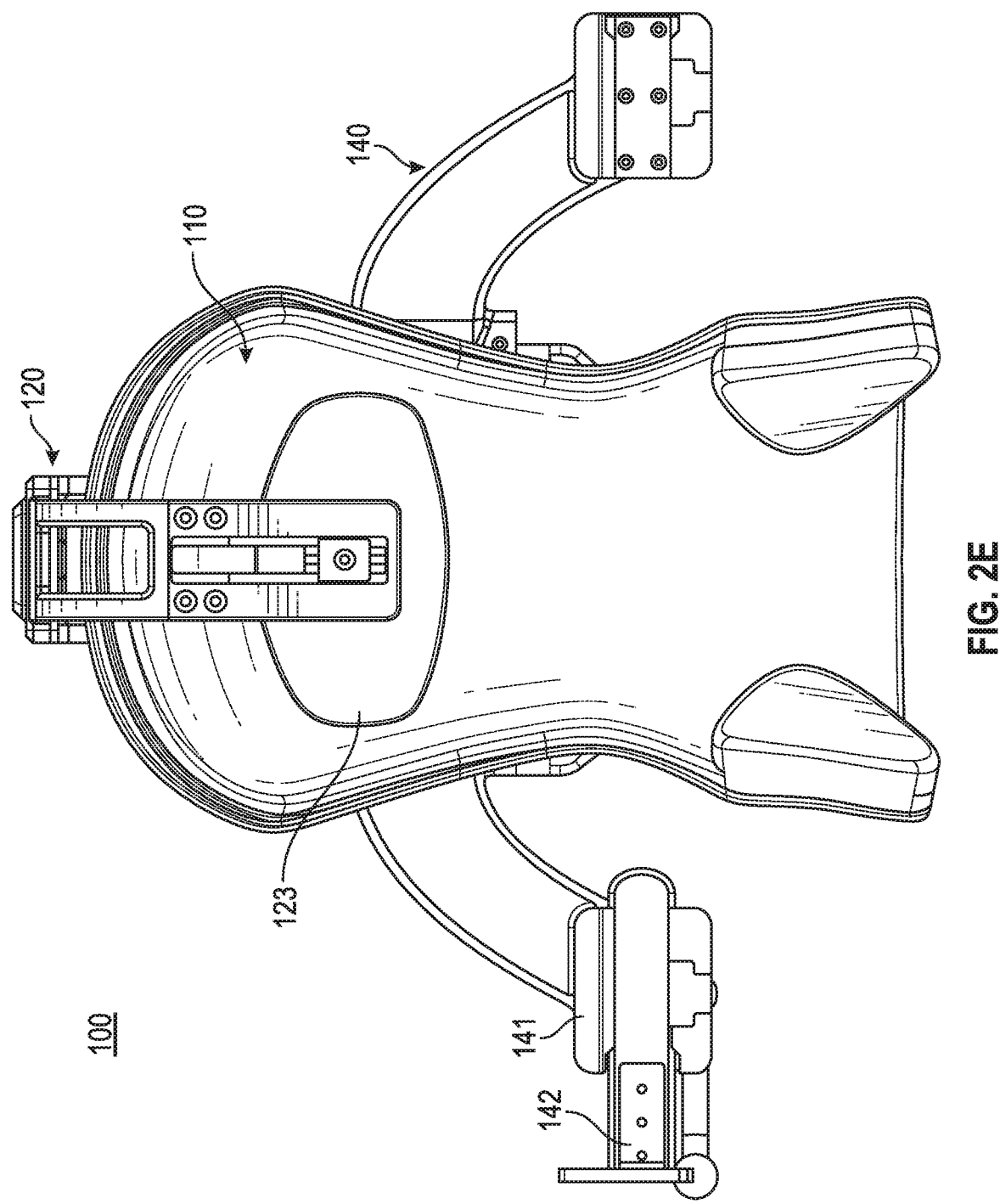

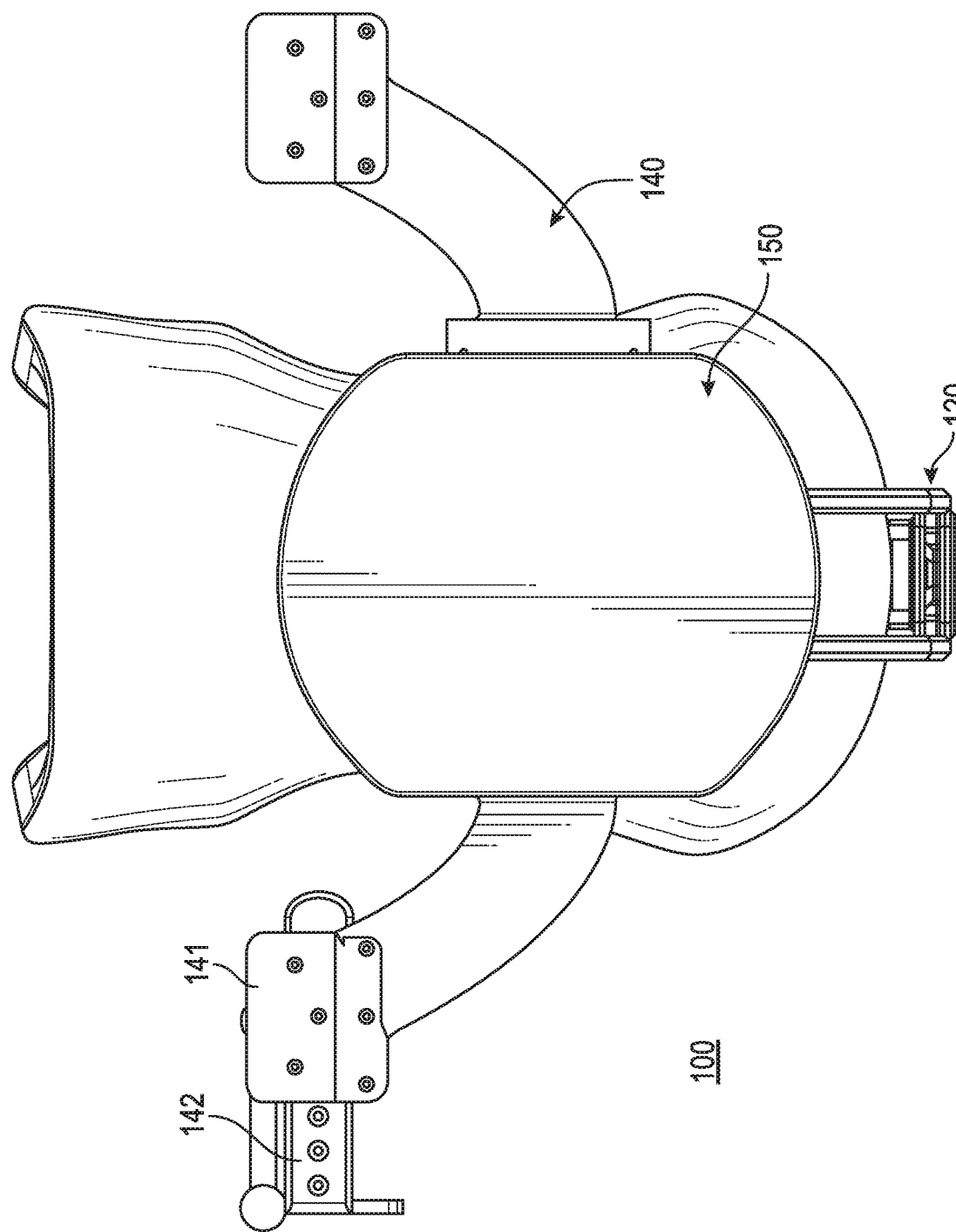

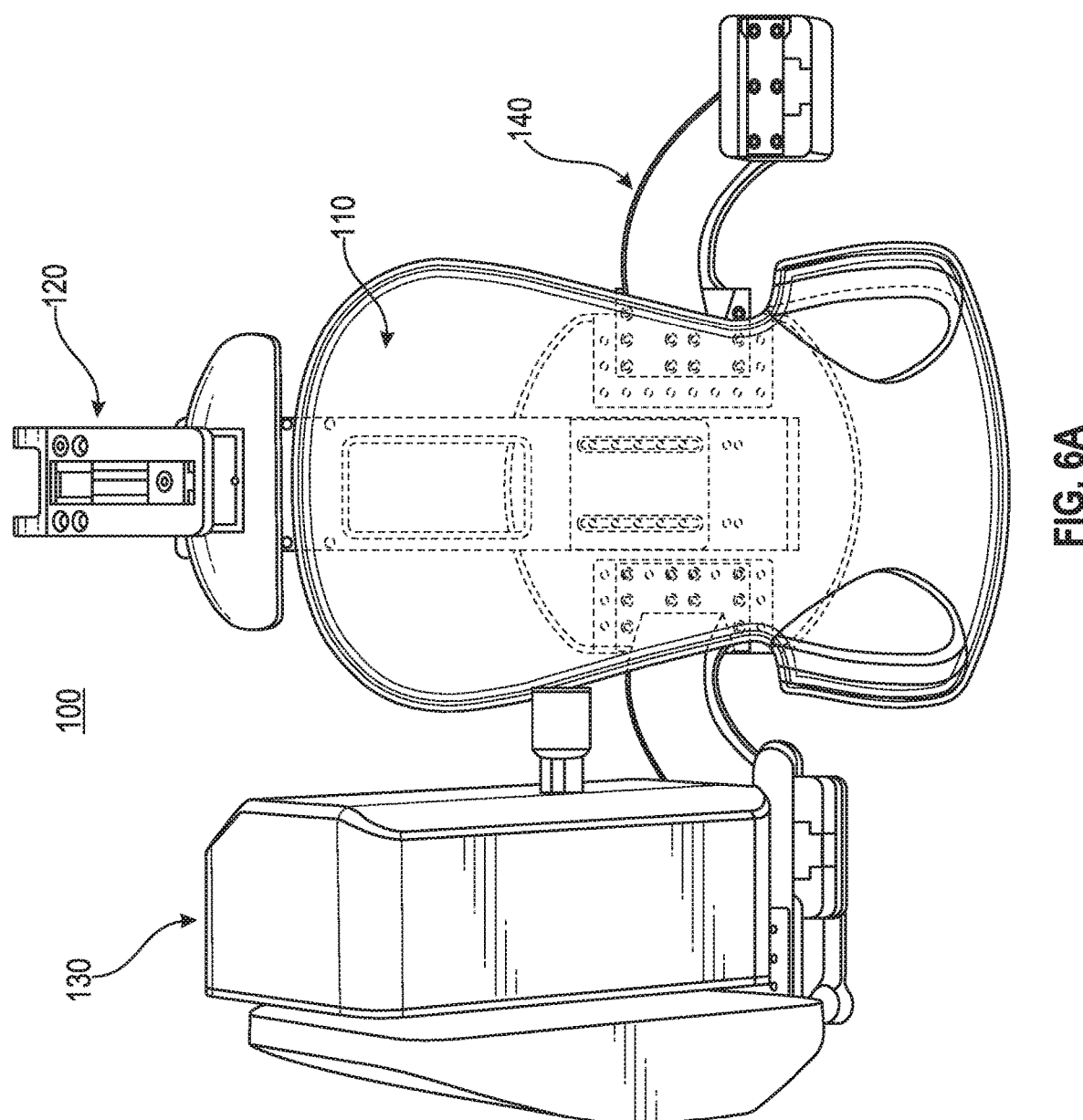

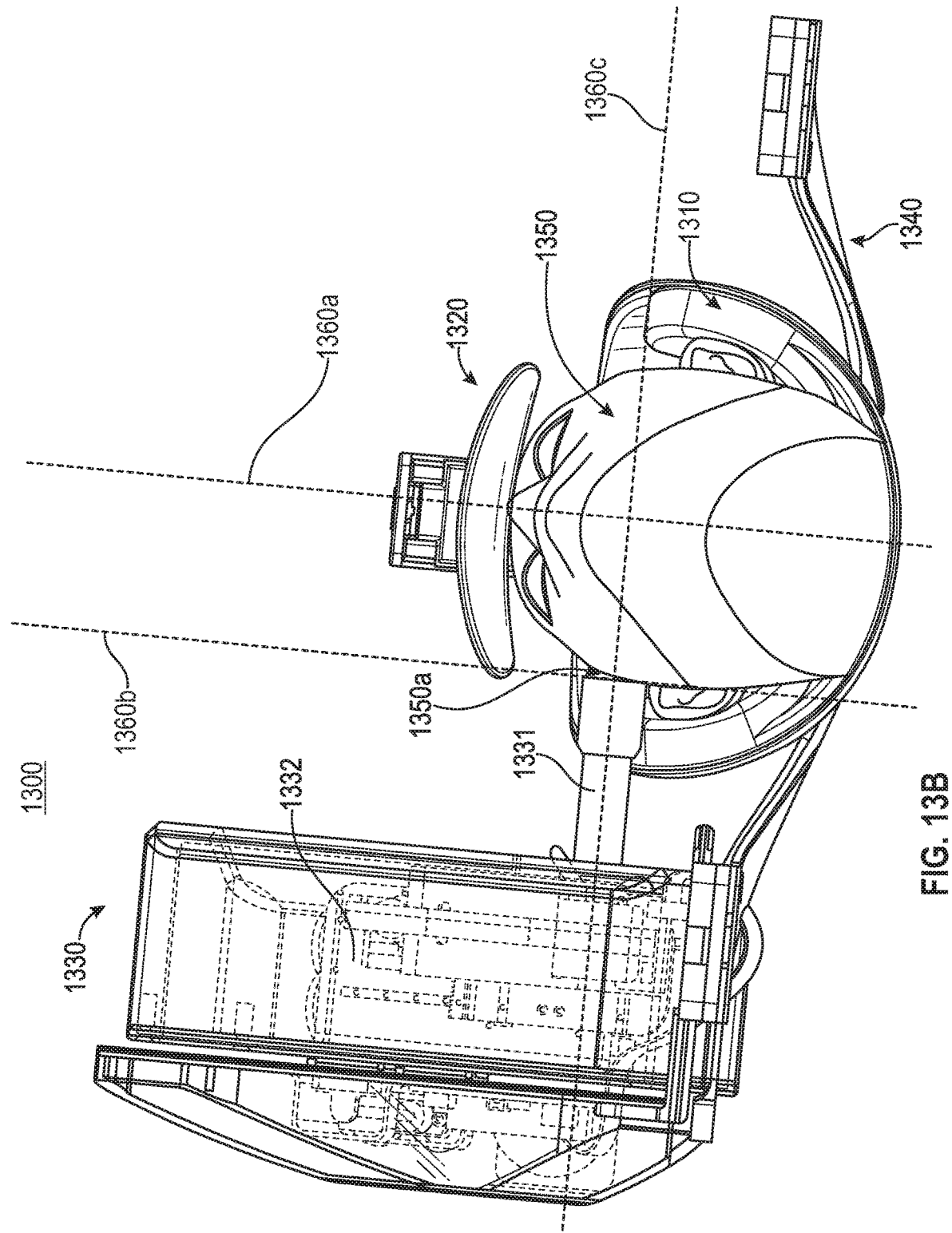

DYNAMIC HEADSET APPARATUS

CROSS-REFERENCE TO RELATED PATENT APPLICATION

This application claims priority from U.S. Provisional Application No. 62/544,347, filed on Aug. 11, 2017, incorporated herein by reference in its entirety.

BACKGROUND

For devices utilizing a headset whose performance is optimized by remaining stable with respect to a subject's head (e.g., optical devices, virtual reality headsets, surgical devices, automated Transcranial Doppler devices, and so on), alignment of the device during operation with respect to particular areas of a subject's head is important to maintain for accurate readings and for minimizing operation time by the device (e.g., due to restarts by the device attributable to movements by the subject). Furthermore, if a subject is restrained by a headset such that minimal movement is allowed, comfortability and anxiety of the subject due to the restraint may become issues (e.g., causing the subject to fight against the restraint to create unnecessary displacement between the device and subject).

SUMMARY

According to various arrangements, provided is a headset that allows for dynamic stability of a subject's head therein such that a device attached to the headset can move along with head movements of the subject, thereby allowing the device to remain properly aligned or otherwise properly positioned with respect to locations of the subject's head. In various arrangements, the dynamic headset apparatus optimizes performance and comfort of the headset and device (e.g., by accurately and precisely scanning physiological readings taken with respect to the subject's head and minimizing the time that the procedure implemented by the device takes due to the adequate quality of the data readings).

According to various arrangements, there is provided a dynamic headset apparatus including a head cradle configured to receive a head of a subject. In some arrangements, the head cradle has a bottom surface configured to face a platform on which the dynamic headset apparatus is placed. In some arrangements, the dynamic headset apparatus has a device comprising an instrument adjacent to the head of the subject when the head of the subject is in the head cradle.

In some arrangements, the bottom surface of the head cradle has a convex shape such that an amount of rotation of the head of the subject in the head cradle results in a same amount of rotation at the instrument.

In some arrangements, the rotation of the head of the subject and the rotation of the instrument are about a same axis.

In some arrangements, the head cradle is shaped such that the instrument is adjacent to a same location at the head of the subject before and after the rotation of the head of the subject.

In some arrangements, the bottom surface of the head cradle has a convex and rounded shape.

In some arrangements, the head cradle contacts the platform on which the dynamic headset apparatus is placed.

In some arrangements, the dynamic headset apparatus further includes a mount under the head cradle and having a convex bottom surface configured to face a platform on which the dynamic headset apparatus is placed.

In some arrangements, the mount is attached to the head cradle.

In some arrangements, the dynamic headset apparatus further includes a base having a cavity configured to receive the convex bottom surface of the mount.

In some arrangements, the base is configured to be interposed between the mount and the platform on which the dynamic headset apparatus is placed.

In some arrangements, the cavity of the base has a larger area than that of the convex bottom surface of the mount such that the cavity defines one or more paths of movement for the mount within the cavity.

In some arrangements, the cavity of the base defines a rotational path of movement and a sliding path of movement of the mount.

In some arrangements, the cavity has a circular shape and the rotational path of movement and the sliding path of movement are in any direction from a center of the cavity.

In some arrangements, the cavity has an elongated arc shape and the sliding path of movement is along the elongated arc shape.

In some arrangements, the rotational path of movement and the sliding path of movement are in a same direction.

In some arrangements, the cavity has a concave inner surface for receiving the convex bottom surface of the mount.

In some arrangements, the concave inner surface of the cavity and the convex bottom surface of the mount are rounded.

In some arrangements, the base is releasably attached to the mount.

In some arrangements, the mount is shaped such that an amount of rotation of the head of the subject in the head cradle results in the same amount of rotation at the instrument.

In some arrangements, the mount is shaped such that the instrument is adjacent to a same location at the head of the subject before and after the amount of rotation of the head of the subject.

In some arrangements, the convex bottom surface of the mount has a round shape.

In some arrangements, the instrument is configured to be located proximate to or in contact with a temporal window of the head of the subject.

In some arrangements, the instrument comprises a transducer configured to transmit or receive energy waves with respect to the head of the subject.

In some arrangements, the energy waves comprise ultrasound, infrared, or near-infrared spectroscopy (NIRS) energy waves.

In some arrangements, the dynamic headset apparatus further includes a device attachment mechanism extending from the head cradle, wherein the device is releasably attached to the device attachment mechanism.

In some arrangements, the head cradle is configured to receive a back portion of the head of the subject such that the subject is in a supine position when the head of the subject is in the head cradle.

According to various arrangements, a method of manufacturing a dynamic headset apparatus includes providing a head cradle configured to receive a head of a subject and having a bottom surface configured to face a platform on which the headset system is placed. The method further includes providing a device including an instrument adjacent to the head of the subject when the head of the subject is in the head cradle.

BRIEF DESCRIPTION OF THE FIGURES

Features, aspects, and advantages of the present invention will become apparent from the following description and the accompanying example arrangements shown in the drawings, which are briefly described below.

FIG. 1A, FIG. 1B, FIG. 1C, FIG. 1D, FIG. 1E, FIG. 1F, and FIG. 1G illustrate various views of a dynamic headset apparatus including a device coupled thereto according to various arrangements.

FIG. 2A, FIG. 2B, FIG. 2C, FIG. 2D, FIG. 2E, FIG. 2F, and FIG. 2G illustrate various views of the dynamic headset apparatus illustrated in FIGS. 1A-1G, without the coupled device, according to various arrangements.

FIG. 6A and FIG. 6B illustrate transparent views of the dynamic headset apparatus illustrated in FIGS. 1A-1G according to various arrangements.

FIG. 13B illustrates a front view of the dynamic headset apparatus and the head of the subject therein as illustrated in FIG. 13A after an amount of rotation of the head of the subject according to various arrangements.

DETAILED DESCRIPTION

Figure 1A:
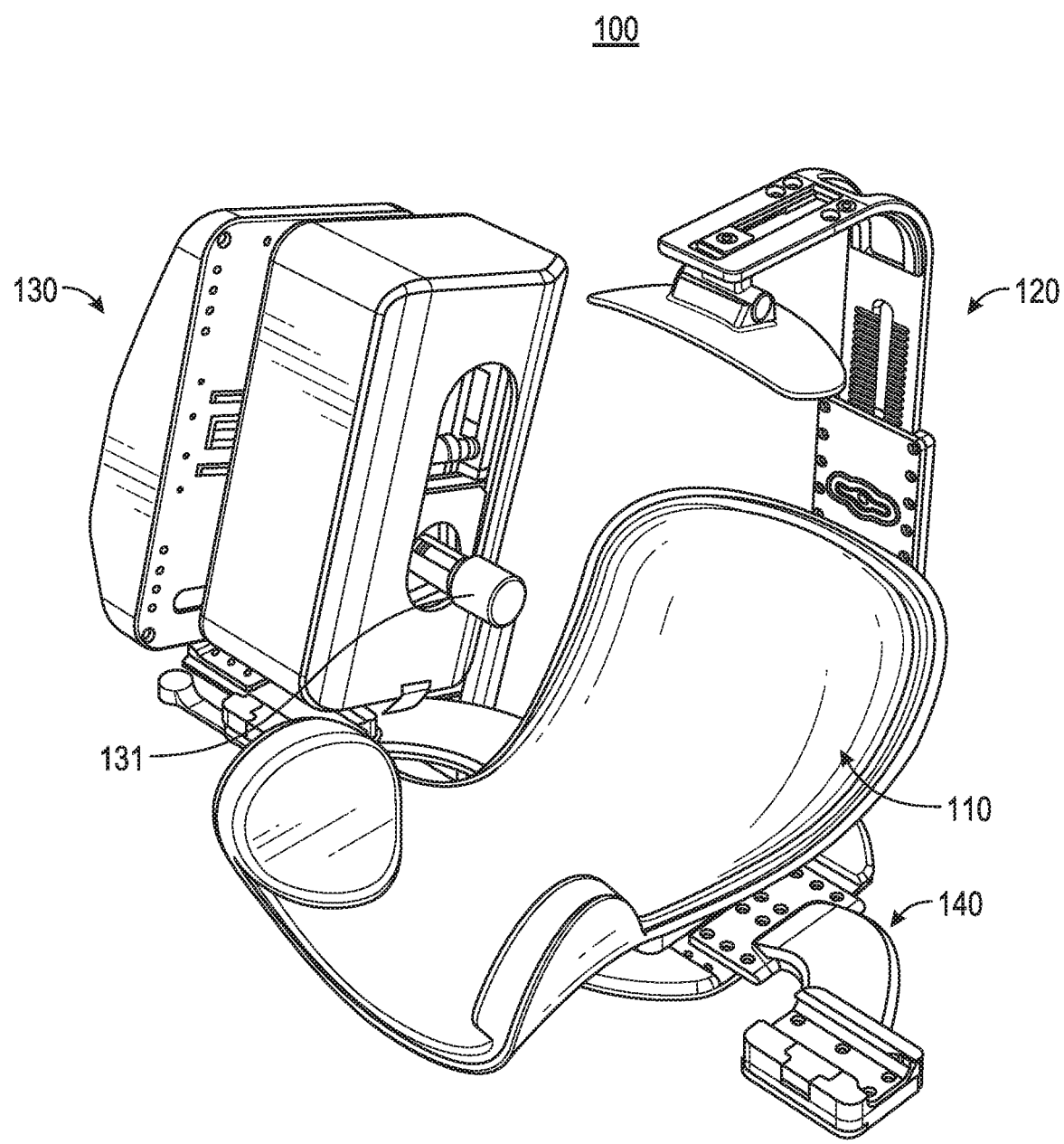
Figure 1B:
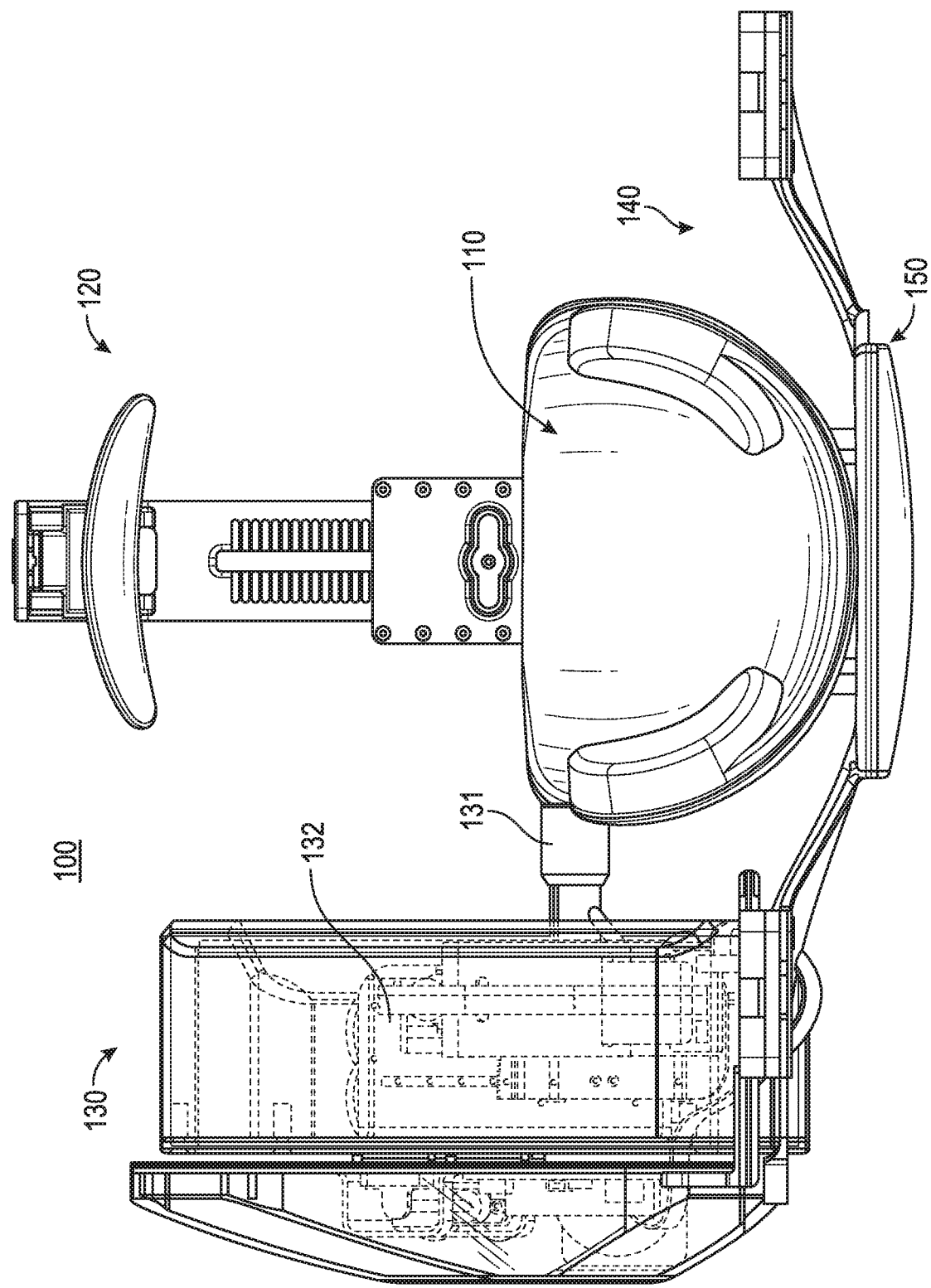
Figure 1C:
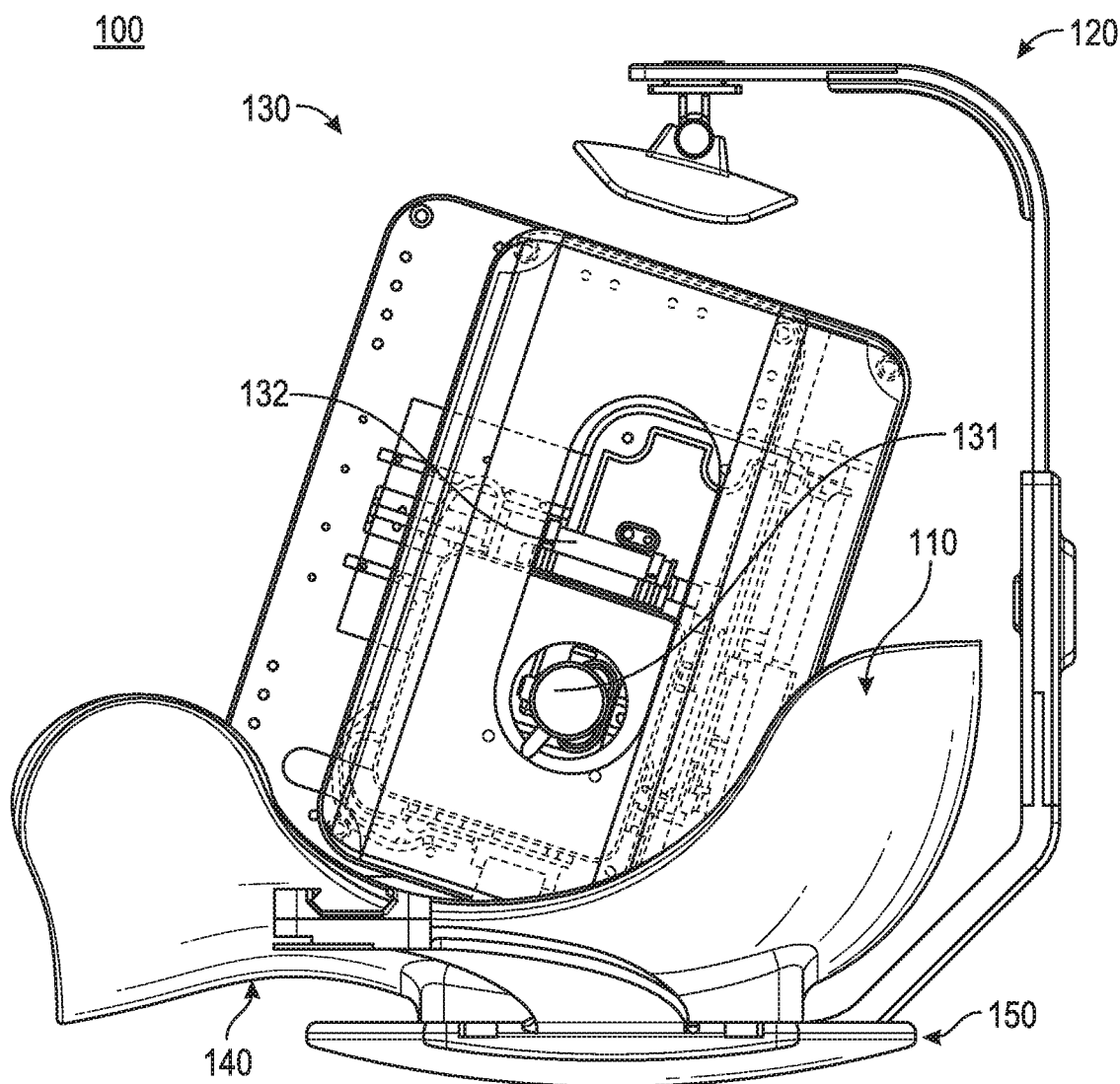
Figure 1D:
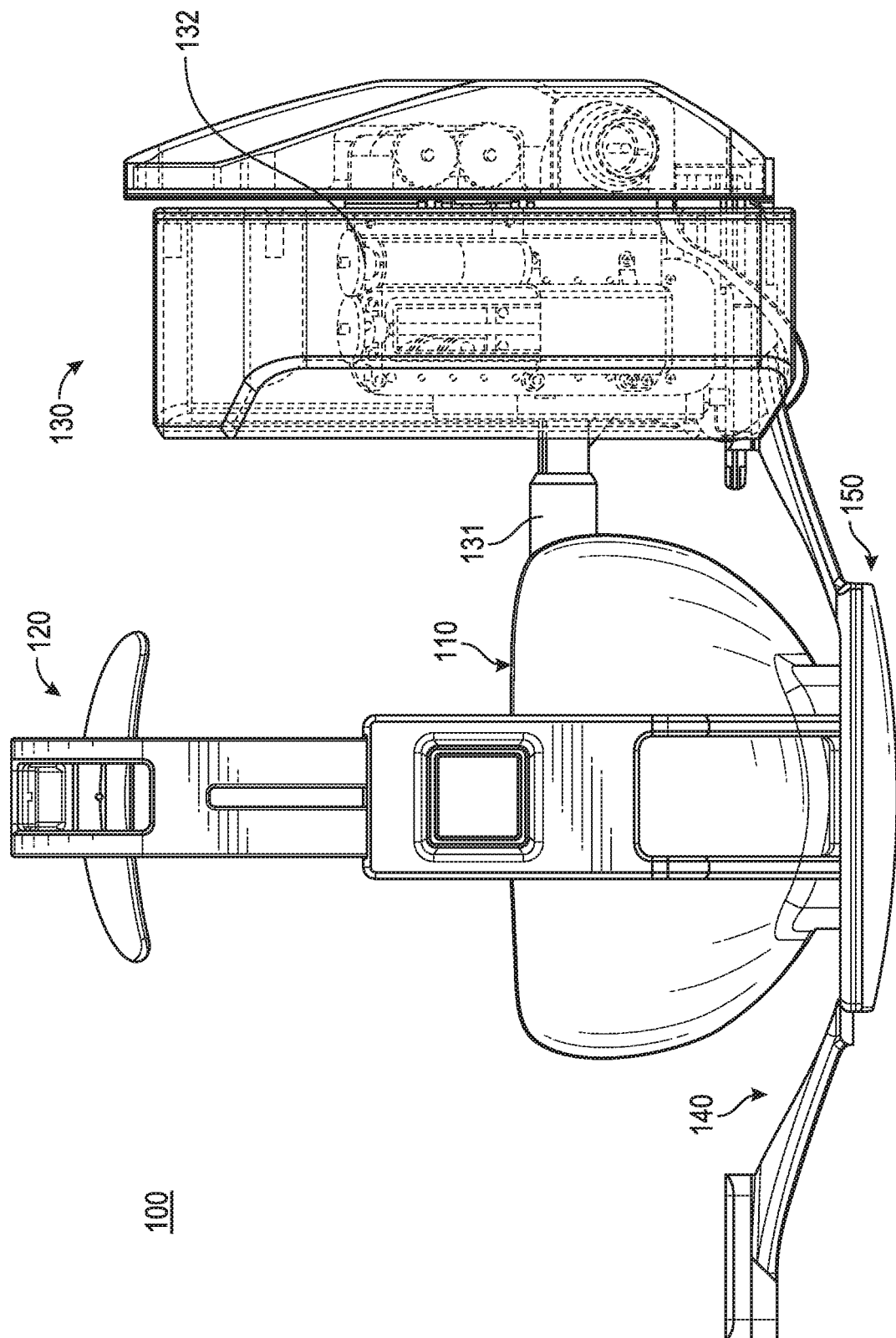
Figure 1F:
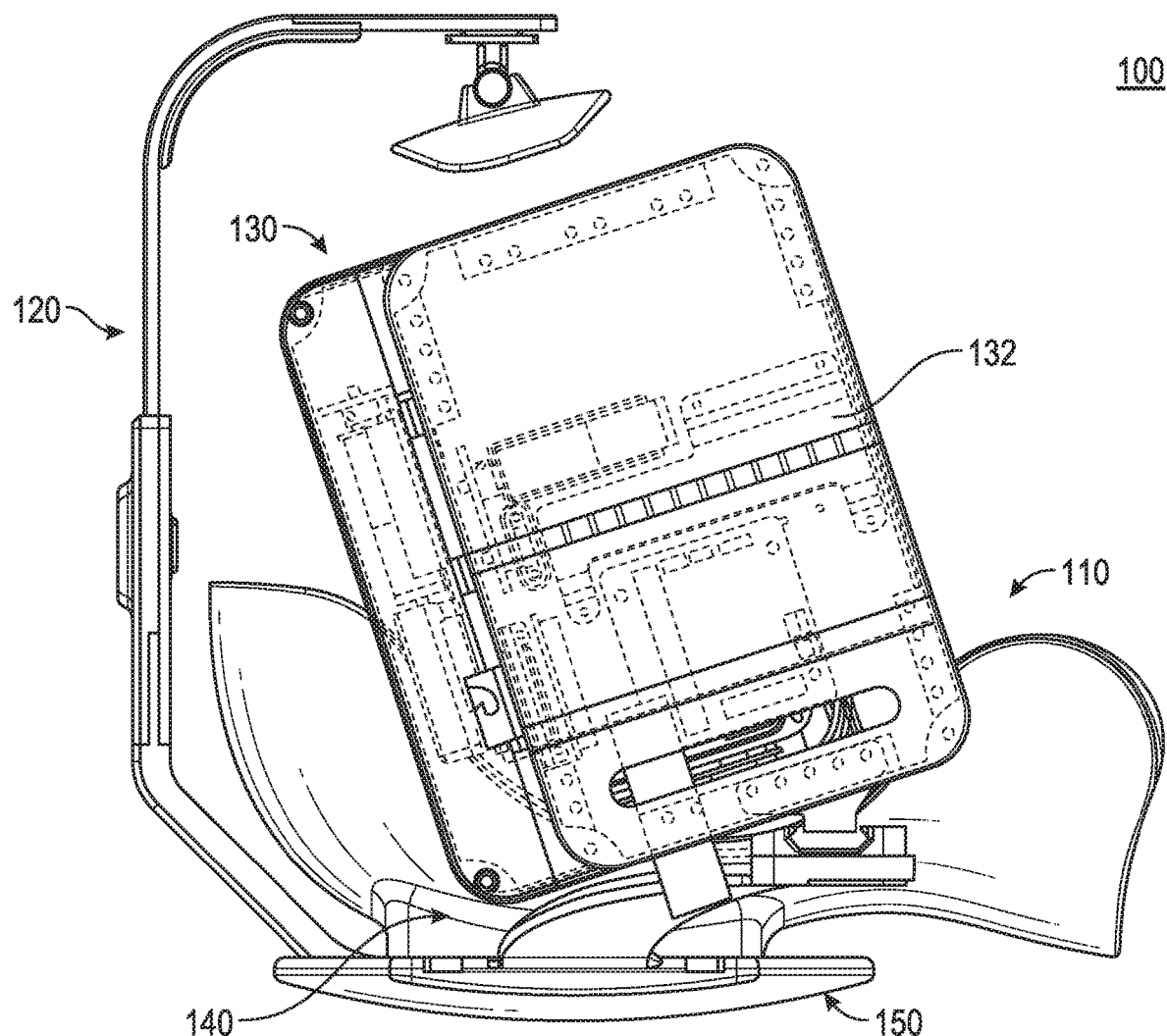
Figure 1G:
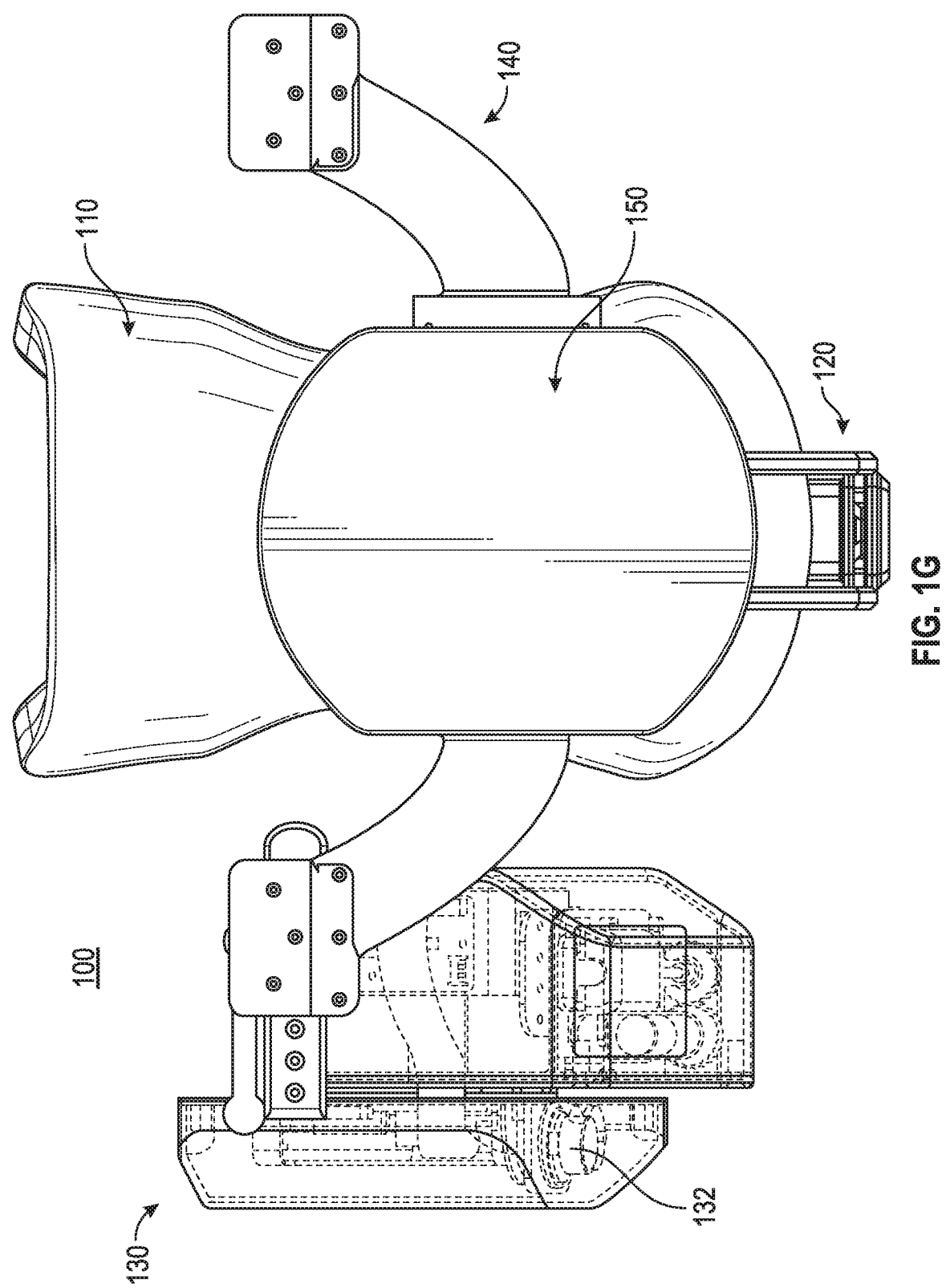
Figure 2A:
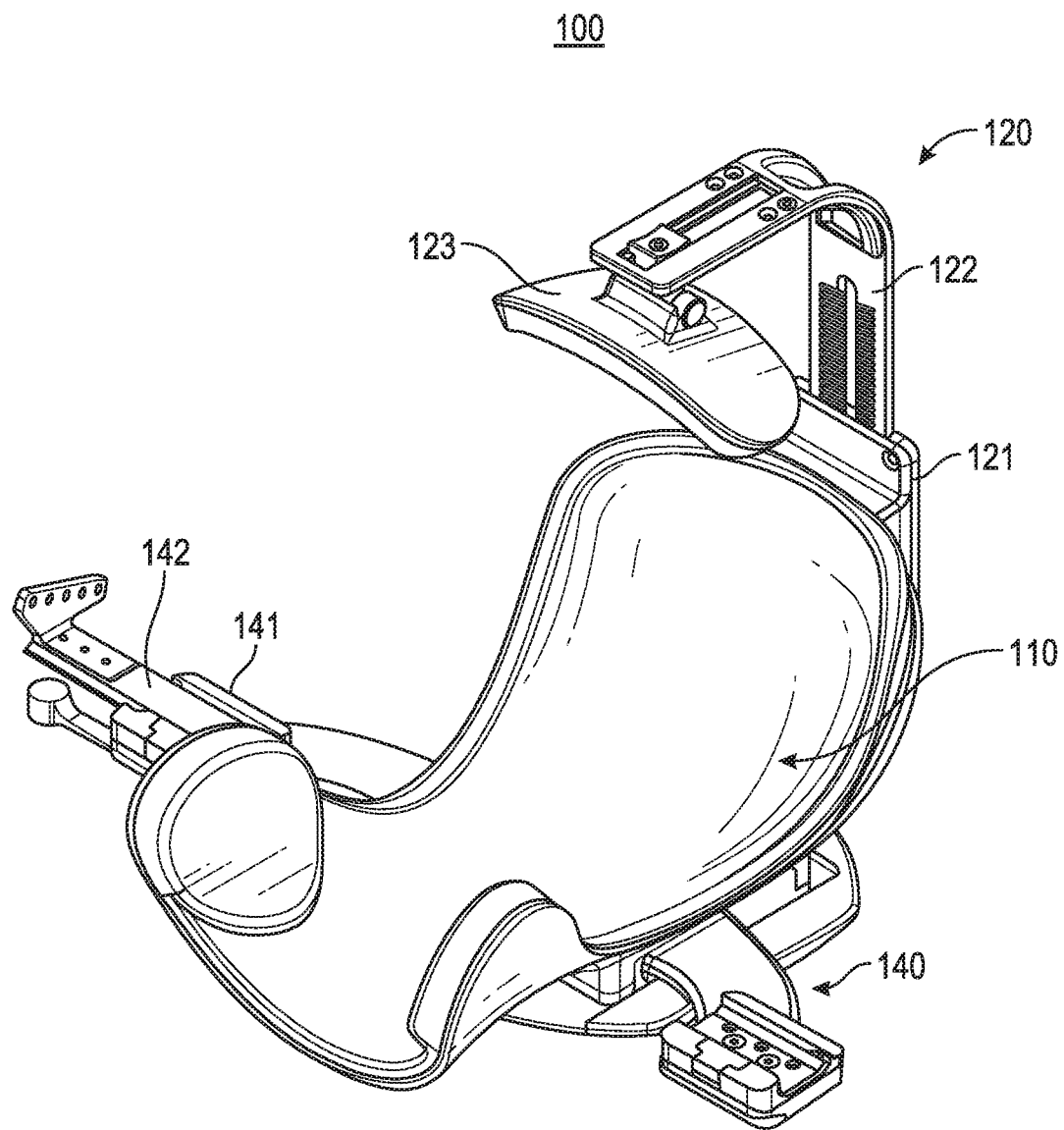
Figure 2C:
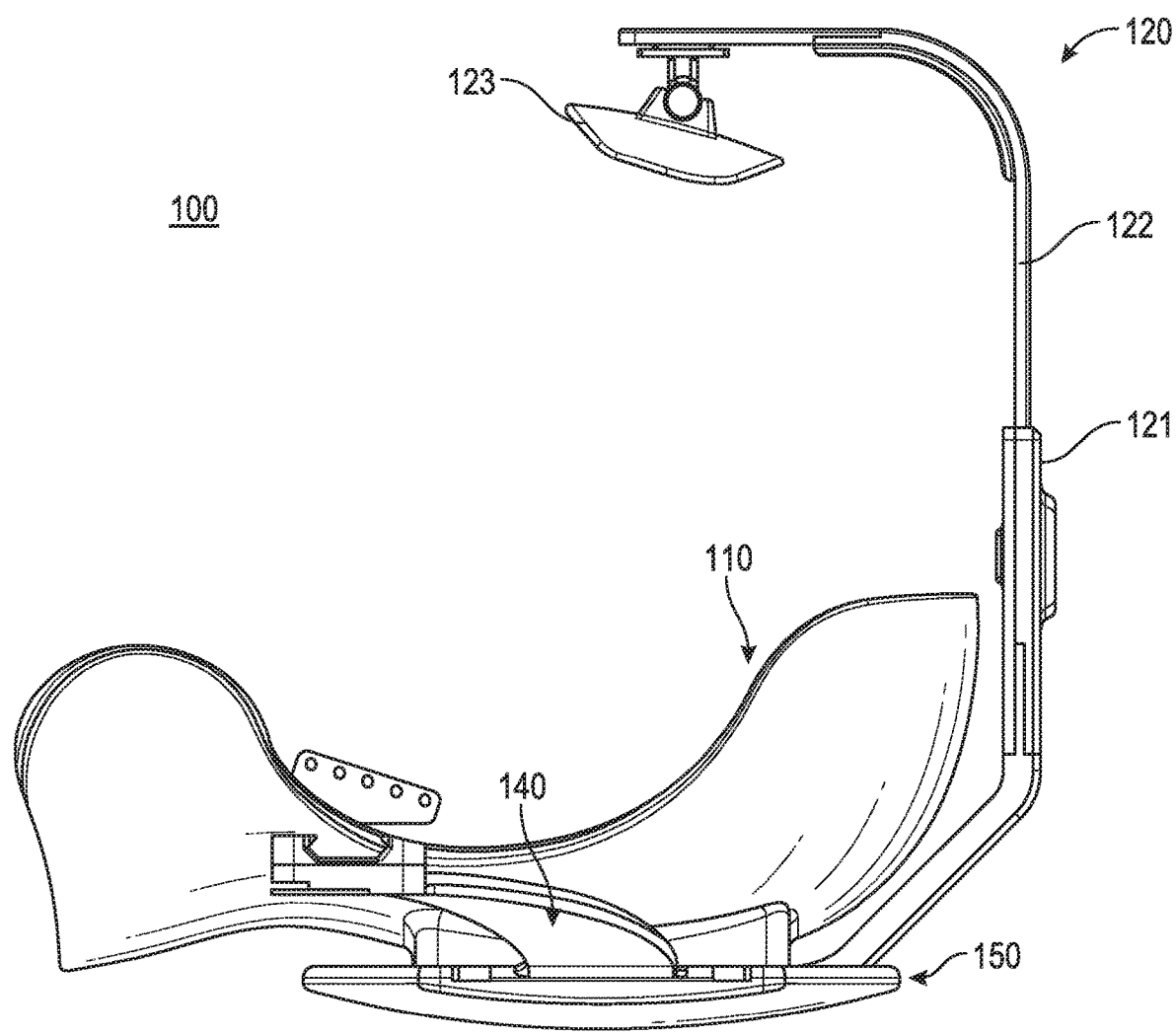
Figure 2D:
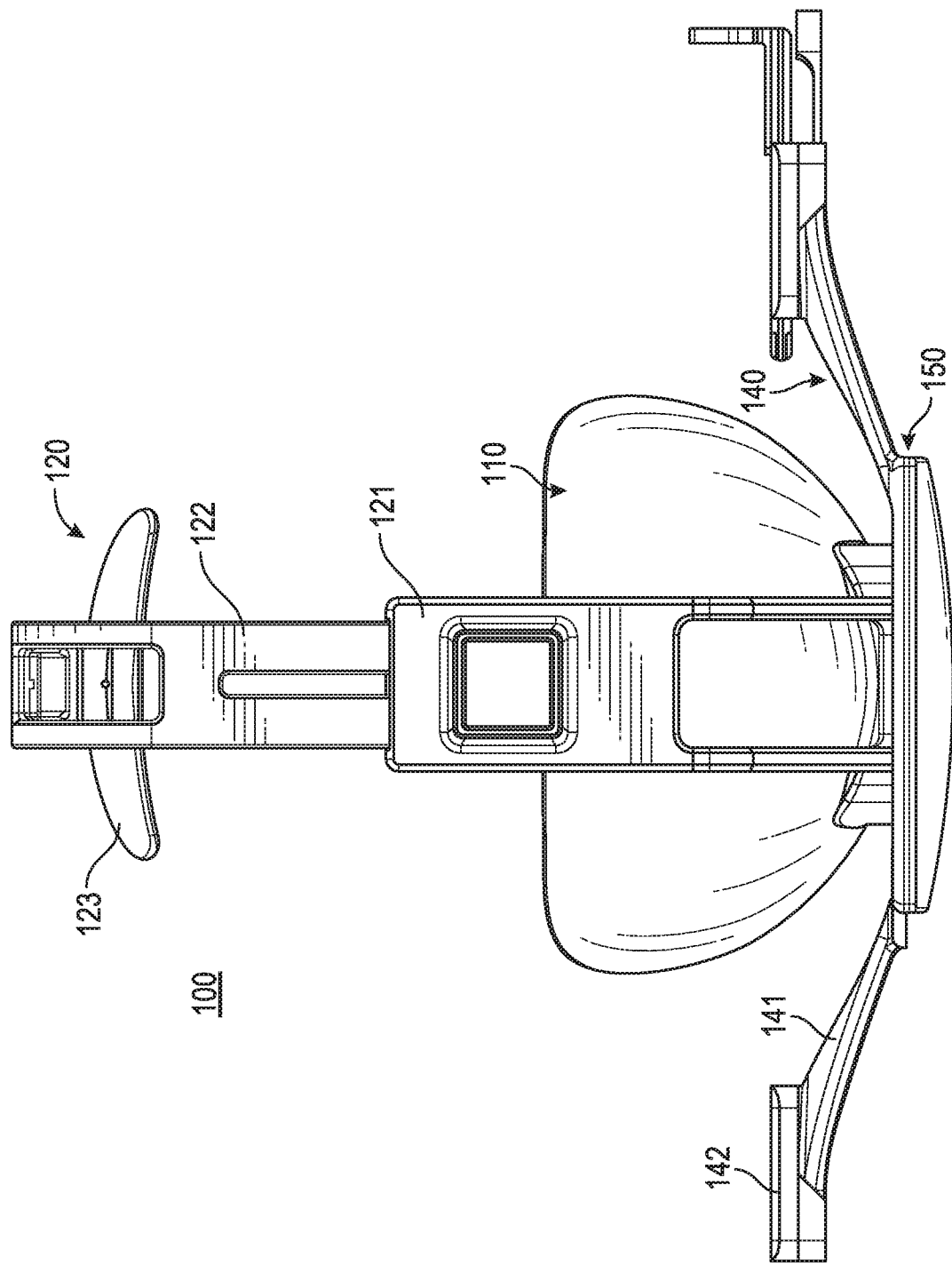
Figure 2F:
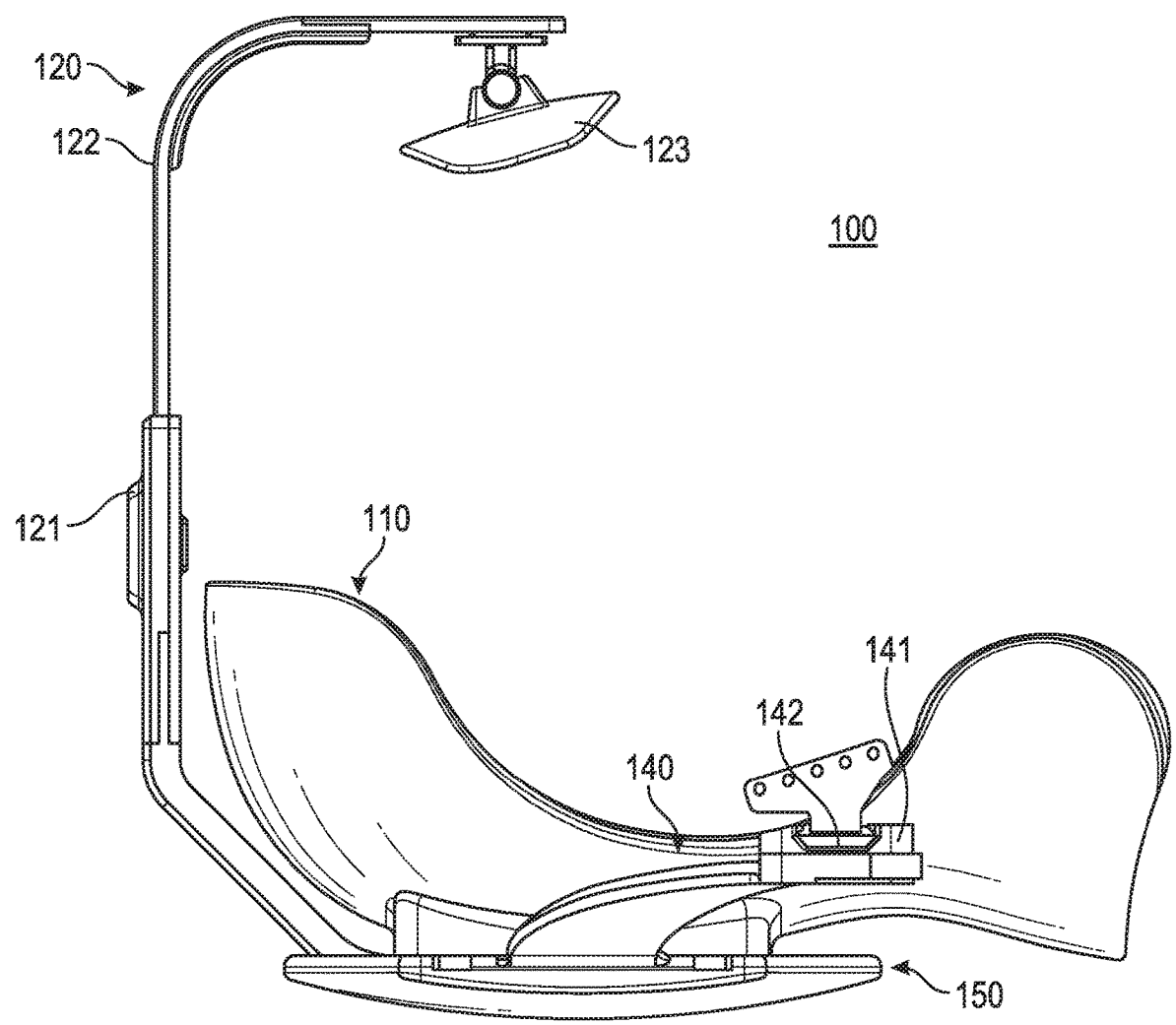

The detailed description set forth below in connection with the appended drawings is intended as a description of various configurations and is not intended to represent the only configurations in which the concepts described herein may be practiced. The detailed description includes specific details for providing a thorough understanding of various concepts. However, it will be apparent to those skilled in the art that these concepts may be practiced without these specific details. In some instances, well-known structures and components are shown in block diagram form in order to avoid obscuring such concepts.

In the following description of various arrangements, reference is made to the accompanying drawings which form a part hereof and in which are shown, by way of illustration, specific arrangements in which the arrangements may be practiced. It is to be understood that other arrangements may be utilized, and structural changes may be made without departing from the scope of the various arrangements disclosed in the present disclosure.

In some arrangements, headsets provide dynamic stability of a subject's head therein such that a device attached to the headset can move along with head movements of the subject, to optimize performance of the device. Furthermore, by allowing movement with the headset (e.g., movement of the headset along with the head while the headset is attached thereto), subject anxiety may be reduced due to the subject not being completely restricted from movement. In addition, in some arrangements, the headsets allow for use on subjects that have anatomy shifting characteristics in specific positions (e.g., stroke subjects that heavily bias their neck to the left or right shoulder such that their head is not aligned with the spinal axis).

FIG. 1A, FIG. 1B, FIG. 1C, FIG. 1D, FIG. 1E, FIG. 1F, and FIG. 1G illustrate various views of a dynamic headset apparatus 100 including a device 130 coupled thereto according to various arrangements. FIG. 2A, FIG. 2B, FIG. 2C, FIG. 2D, FIG. 2E, FIG. 2F, and FIG. 2G illustrate various views of the dynamic headset apparatus 100 illustrated in FIGS. 1A-1G, without the coupled device 130, according to various arrangements.

In some arrangements, the dynamic headset apparatus 100 includes a head cradle 110, a restraint system 120, the device 130, a device attachment mechanism 140, and a mount 150. In some arrangements, the cradle 110 is configured to receive and support a subject's head (e.g., during operation of the device 130). In some arrangements, the cradle 110 includes a frame and padding attached to the frame. The frame supports the padding, while the padding is configured to contact a human head. In some arrangements, the frame of the cradle 110 is shaped to suitably contour and support varying head sizes and shapes, and the frame is also shaped to adequately position a user's head in a workspace of the device 130. In some arrangements, the frame of the cradle 110 is made from any suitably malleable material that allows for flexing, such as, but not limited to, flexible plastics, polyethylene, urethanes, polypropylene, ABS, nylon, fiber-reinforced silicones, structural foams, or the like.

In some arrangements, the padding of the cradle 110 is made from any suitable soft material, such as, but not limited to, closed cell foam, open cell foam, self-skinning open or closed cell foams, cast, aerated, or extruded silicone or urethane, polyurethane gels that are configured to distribute pressure efficiently, or the like. In some arrangements, the padding of the cradle 110 has any suitable firmness for supporting a head, such as, but not limited to, in a range of about 0.1 pound per square inch (psi) to about 60 psi (e.g., in a range of about 0.1 psi to about 10 psi) or within other suitable ranges of firmness. In some arrangements, the padding of the cradle 110 has memory for expanding to fit contours of a head. In some arrangements, the padding (e.g., foam) of the cradle 110 is compressed and expands after a user's head is placed in the headset apparatus 100 so that the padding expands to secure the headset apparatus 100. In some arrangements, the cradle 110 including the padding is manufactured by any suitable process for affixing the padding within the headset apparatus 100, such as, but not limited to, injection molding, laminating, adhesive mounting (e.g., gluing or bonding), co-molding, co-casting, injection, snapping, by Velcro fastening, by hook and loop fastening, friction fitting, attaching with barbs, using screw bosses, or the like.

In other arrangements, the padding of the cradle 110 includes an inflatable bladder. In some arrangements, the bladder is a hollow void that is filled manually or with a pump. In such arrangements, the inflatable bladder is self-inflating with an internal structure that has a memory and that expands within the bladder to inflate to at least about 90% capacity. In other arrangements, the bladder is inflated to other suitable capacities, such as, but not limited to, at least about 95% capacity, at least about 80% capacity, at least about 70% capacity, and so on. In further arrangements, inflation is assisted with an integrated pump or an external filling or pumping source. In some arrangements, the inflatable bladder is filled with air, gas, liquid, or any other suitable element for affixing or securing the inflatable padding of the headset apparatus 100 to a user's head. In other arrangements, the bladder is filled with plastic beads or pellets. In particular arrangements, the bladder that is filled with plastic beads or pellets becomes rigid, so as to capture or form around a subject's head, when a vacuum is applied to the bladder.

In some arrangements, the cradle 110 is shaped to form a recess or cavity for receiving a head of a subject. In some arrangements, the cavity defined by the cradle 110 also retains and restricts the head of the subject to remain within the cradle 110. In some arrangements, the shape of the cradle 110 is defined to correspond and contour to the shape of a head of a subject (e.g., the shape of the cradle 110 is concave to receive the convex shape of the head of the subject). In some arrangements, the cradle 110 is elongated so as to also contact a neck area of a subject (e.g., an upper neck area of the subject). In some arrangements, the elongated cradle 110 provides added stability between a subject and the dynamic headset apparatus 100. In some arrangements, the elongated portion of the cradle 110 that is configured to contact the neck of the subject include two lateral protrusions. In some arrangements, the lateral protrusions surrounding the neck portion so as to provide further restraint and security of the subject within the dynamic headset apparatus 100. Accordingly, in some arrangements, the surface of the cavity defined by the cradle 110 has a curvature that substantially corresponds or aligns with a back of a head and portion of a neck of a subject. In other arrangements, the cradle 110 is designed to contact the back of a head of the subject, but not the neck of the subject.

In some arrangements, the cradle 110 has varying widths along its length. For example, in some arrangements, at the top of the cradle 110 (e.g., the portion of the cradle 110 that is adjacent to the restraint system 120) the cradle 110 has a relatively large width. Furthermore, in some arrangements, towards the middle of the cradle 110, the width condenses and then widens again thereafter towards the bottom of the cradle 110. In other arrangements, the cradle 110 can define any suitable shape for adequately receiving a head of a subject. For example, the cradle 110 can define a substantially flat surface, an elevated surface, a recess at which a subject places his or her head, and so on. In some arrangements, the cradle 110 is a simple platform for placing a head of a subject.

In some arrangements, the restraint system 120 is configured to restrain a subject's head when placed in the cradle 110. In some arrangements, the restraint system 120 includes a foundation 121, a body 122, and a contact 123. In some arrangements, the foundation 121 is attached to the mount 150. In some arrangements, the body 122 includes an elongated section that is configured to slide into the foundation 121, and lock while in the foundation 121, so as to provide adjustability of the restraint system 120 to accommodate different heads of different subjects (e.g., different sizes and shapes). In some arrangements, the contact 123 is attached to the body 122, and the contact 123 is configured to contact and apply pressure against a subject's head (e.g., forehead) for securing the headset apparatus 100 to the subject. In some arrangements, the contact 123 is configured to pivot at a location where the contact 123 is attached to the body 122 to provide further adjustability for different sized and shaped heads of subjects. In some arrangements, the contact 123 includes a padding for contacting a subject's head, and the padding is made from any suitable soft material, such as, but not limited to, closed cell foam, open cell foam, self-skinning open or closed cell foams, cast, aerated, or extruded silicone or urethane, polyurethane gels that are configured to distribute pressure efficiently, or the like.

In some arrangements, the headset apparatus 100 includes different forms of the restraint system 120. For example, the body 122 of the restraint system 120 can extend laterally or diagonally (e.g., upwards and diagonally) from the foundation 121 such that the contact 123 is configured to contact a side portion of the subject's head (e.g., a temple, a portion adjacent to the forehead, and so on). The body 122 can extend in a telescoping action from the foundation 121. In some arrangements, a plurality of bodies 122 can extend from the foundation 121, and each of the bodies 122 is attached to a separate contact 123 such that the restraint system 120 is configured to contact and restrain the subject's head at multiple locations along the subject's head. For example, in addition to a middle body (e.g., the body 122 as shown), a plurality of bodies (each of which may be a body such as but not limited to, the body 122) can extend laterally from the foundation 121 and end in contacts (each of which may be a contact such as but not limited to, the contact 123) configured to contact side portions of a subject's head. In other arrangements, the headset apparatus 100 does not include the restraint system 120. In some arrangements, the restraint system 120 includes a plurality of contacts 123 at the end of the body 122 and each of the plurality of contacts 123 is configured to contact a different location of the head of the subject.

In some arrangements, the device 130 is modular and can be attached and detached from the headset apparatus 100 via the attachment mechanism 140. In some arrangements, the headset apparatus 100 is used in conjunction with a medical device for use with respect to a user's head (e.g., an ocular monitoring system, a breathing device, a device for monitoring neurological activity, a surgical device, a device for monitoring radioactive traces, or any other device that is optimized when the device itself is not positionally disturbed with respect to a user's head). In other arrangements, the headset apparatus 100 is used in conjunction with a non-medical device for use with respect to a user's head (e.g., a virtual reality eyepiece).

In some arrangements, the device 130 includes a transducer or a probe 131 and robotics 132 for controlling the probe 131, collectively referred to as an "instrument." In that regard, "instrument" as used herein refers to at least one data collection device (e.g., a probe such as but not limited to, the probe 131) and devices (e.g., positioning components such as but not limited to, the robotics 132) configured to control position and operations (e.g., data collection) of the data collection device. The robotics 132 are configured to translate the probe 131 along a surface of a head and to move the probe 131 towards and away from the head. In some arrangements, an end of the probe 131 interfaces with the robotics 132, and the robotics 132 include components, such as, but not limited to, a motor assembly and the like for controlling the probe 131 (e.g., control z-axis pressure, normal alignment, or the like of the probe 131).

In some arrangements, the probe 131 includes a first end and a second end that is opposite to the first end. In some arrangements, the first end includes a concave surface that is configured to be adjacent to or contact a scanning surface (e.g., a head of a subject). The concave surface is configured with a particular pitch to focus generated energy towards the scanning surface. In some arrangements, the device 130 is a Transcranial Doppler (TCD) apparatus such that the first end of the probe 131 is configured to be adjacent to or contact and align along a human head (e.g., a side of the human head), and the first end of the probe 131 is configured to provide ultrasound wave emissions from the first end and directed into the human head (e.g., towards the brain). In other arrangements, the probe is configured to emit other types of waves during operation, such as, but not limited to, infrared, x-rays, electromagnetic, thermal, near-infrared, optical, lighting, audio, electroencephalography, or the like.

In some arrangements, the second end of the probe 131 is coupled to the robotics 132. In some arrangements, the second end of the probe 131 includes a threaded section along a portion of the body of the probe 131, and the second end is configured to be secured in the robotics 132 via the threads (e.g., by being screwed into the robotics 132). In other arrangements, the probe 131 is secured in the robotics 132 by any other suitable connecting means, such as, but not limited to, welding, adhesive, one or more hooks and latches, one or more separate screws, press fittings, or the like.

In other arrangements, the probe 131 is attached within the headset apparatus 100 without any robotics 132, such that the probe 131 is configured to be manually operated by an operator while the headset apparatus 100 is positioned on a user's head. For example, a user's head can be placed in the headset apparatus 100 and an operator can manually shift and orient the probe 131 while the probe 131 is activated. Accordingly, the probe 131 attached at the headset apparatus 100 will not be affected by some movements (e.g., rotation) of a user's head since the headset apparatus 100 is a dynamic headset apparatus that can allow the probe 131 to move along with movement of the user's head, thereby optimizing performance by the operator of the probe 131.

Further disclosure regarding probe systems that can be used in conjunction with the headsets described herein can be found in non-provisional patent application Ser. No. 15/399,648, titled ROBOTIC SYSTEMS FOR CONTROL OF AN ULTRASONIC PROBE, and filed on Jan. 5, 2017, which is incorporated herein by reference in its entirety.

In some arrangements, the headset apparatus 100 holds other medical and non-medical devices that are used and stabilized with respect to a user's head. For example, in some arrangements, an ocular device is a device that is optimized by maintaining positioning and alignment with a user's eyes (e.g., if the ocular device is shifted with respect to a user's eyes, performance of the ocular device may decline). In some arrangements, the ocular device is attached at the headset apparatus 100 so as to cover the eyes of a subject. As an example of a non-medical device use with respect to the headset apparatus 100, in some arrangements, the headset apparatus 100 can be used in connection with the ocular device that is a virtual reality device configured to provide a virtual experience to the user such that any disturbance of the positioning of the ocular device in front of the user's eyes may cause a degradation in the user's virtual experience.

In some arrangements, the ocular device is a medical device designed to track ocular behavior of a subject (e.g., to diagnose whether the user has experienced a concussion). In other arrangements, the ocular device is an ocular diagnosis or treatment tool for determining or adjusting vision of the user. As an example, the ocular device is a device for correcting imperfect vision of a user (e.g., laser eye surgery). As another example, in some arrangements, the ocular device is an ocular diagnostic tool for determining a vision prescription of a user, presence of one or more eye conditions (e.g., glaucoma, cataracts, ocular hypertension, uveitis, or the like), and so on. In some arrangements, the ocular device is designed to cover and interact with both eyes simultaneously or in sequence. In other arrangements, the ocular device is designed to cover and interact with a single eye (e.g., while the other eye remains uncovered). In some arrangements, because the headset apparatus 100 is dynamic such that the ocular device can move along with movement of a user's head, the ocular device can remain stable, and movement of the ocular device can be minimized so that performance of the ocular device is optimized. The ocular device can be provided with any of the headset apparatuses described herein.

In some arrangements, the attachment mechanism 140 is configured to receive and secure the device 130. In other arrangements, the attachment mechanism 140 is configured to receive and secure other medical and non-medical devices (e.g., those discussed above). In some arrangements, the attachment mechanism 140 includes a track 141 and a slider 142. The track 141 receives the slider 142 and the slider 142 is adjustable along the track 141. For example, the slider 142 can slide within the track 141 and can be locked in place at a desired location. In some arrangements, the attachment mechanism 140 includes two sets of the track 141 and the slider 142, with each set located at an opposite side of the headset apparatus 100. Accordingly, in some arrangements, a plurality of devices 130 can be attached at the headset apparatus 100 for operation with respect to both sides of a subject's head.

In some arrangements, the device 130 is affixed to the slider 142 so that adjustment of the slider 142 results in adjustment of the device 130 with respect to a subject's head (e.g., telescoping adjustment towards and away from the subject's head). In some arrangements, the bottom of the device 130 is connected to the slider 142. In particular arrangements, the device 130 is affixed to the attachment mechanism 140 by any suitable connection mechanism, such as, but not limited to, welding, adhesive, one or more separate bolts, one or more hooks and latches, one or more separate screws, press fittings, or the like. In some arrangements, the attachment mechanism 140 (e.g., the track 141 and/or the slider 142) are made from any suitable rigid material, such as, but not limited to, hard plastic, metals, aluminum, steel, titanium, magnesium, various alloys, rigid plastics, composites, carbon fiber, fiber glass, expanded foam, compression molded foam, stereolithography (SLA) or Fused Deposition Modeling (FDM)-made materials, Reaction Injection Molding (RIM) molding, acrylonitrile butadiene styrene (ABS), thermoplastic olefin (TPO), nylon, polyvinyl chloride (PVC), fiber reinforced resins, or the like.

Figure 3A:
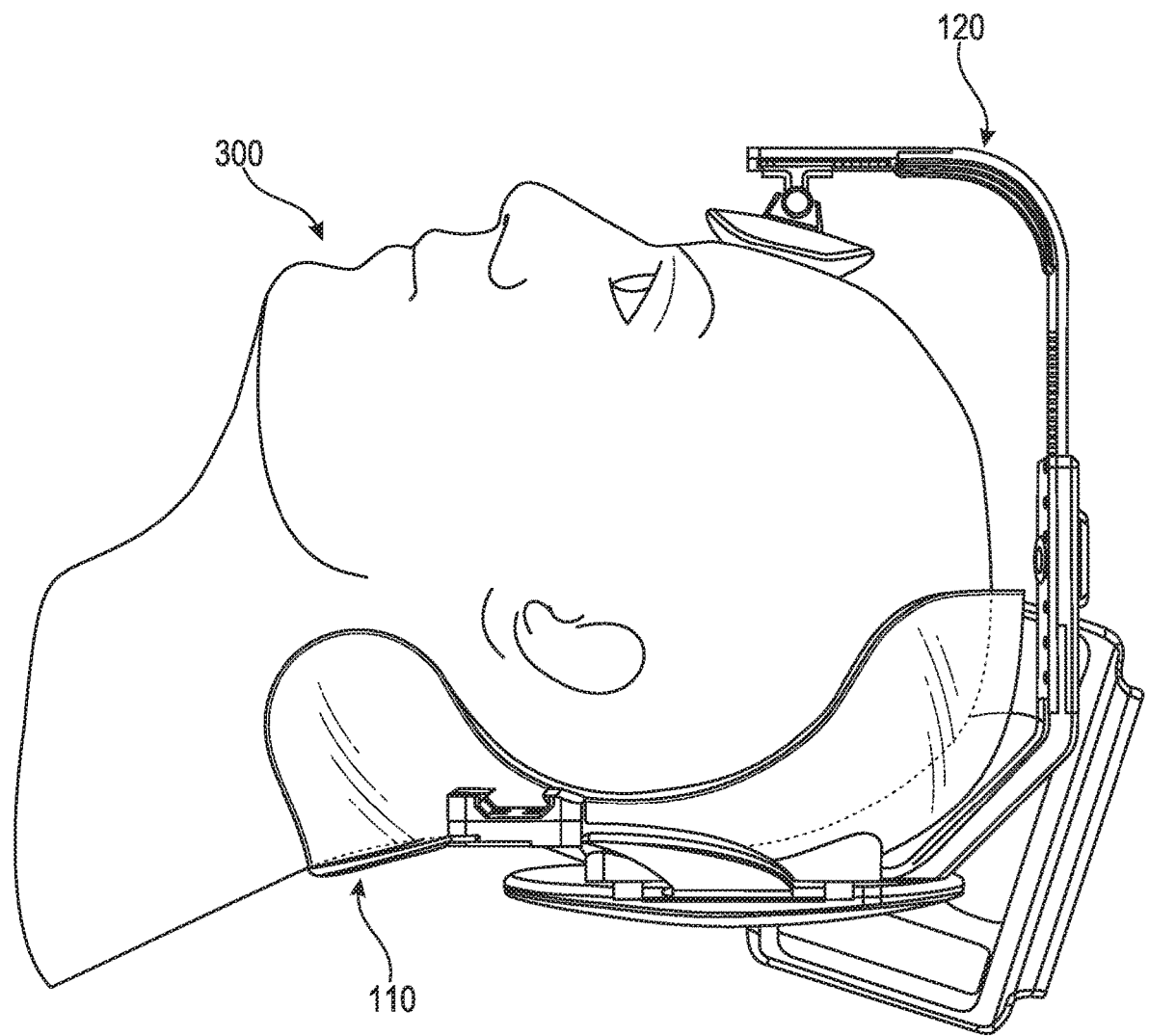
FIG. 3A and FIG. 3B illustrate views of the dynamic headset apparatus illustrated in FIGS. 1A-1G with a subject's head therein according to various arrangements.
Figure 3B:
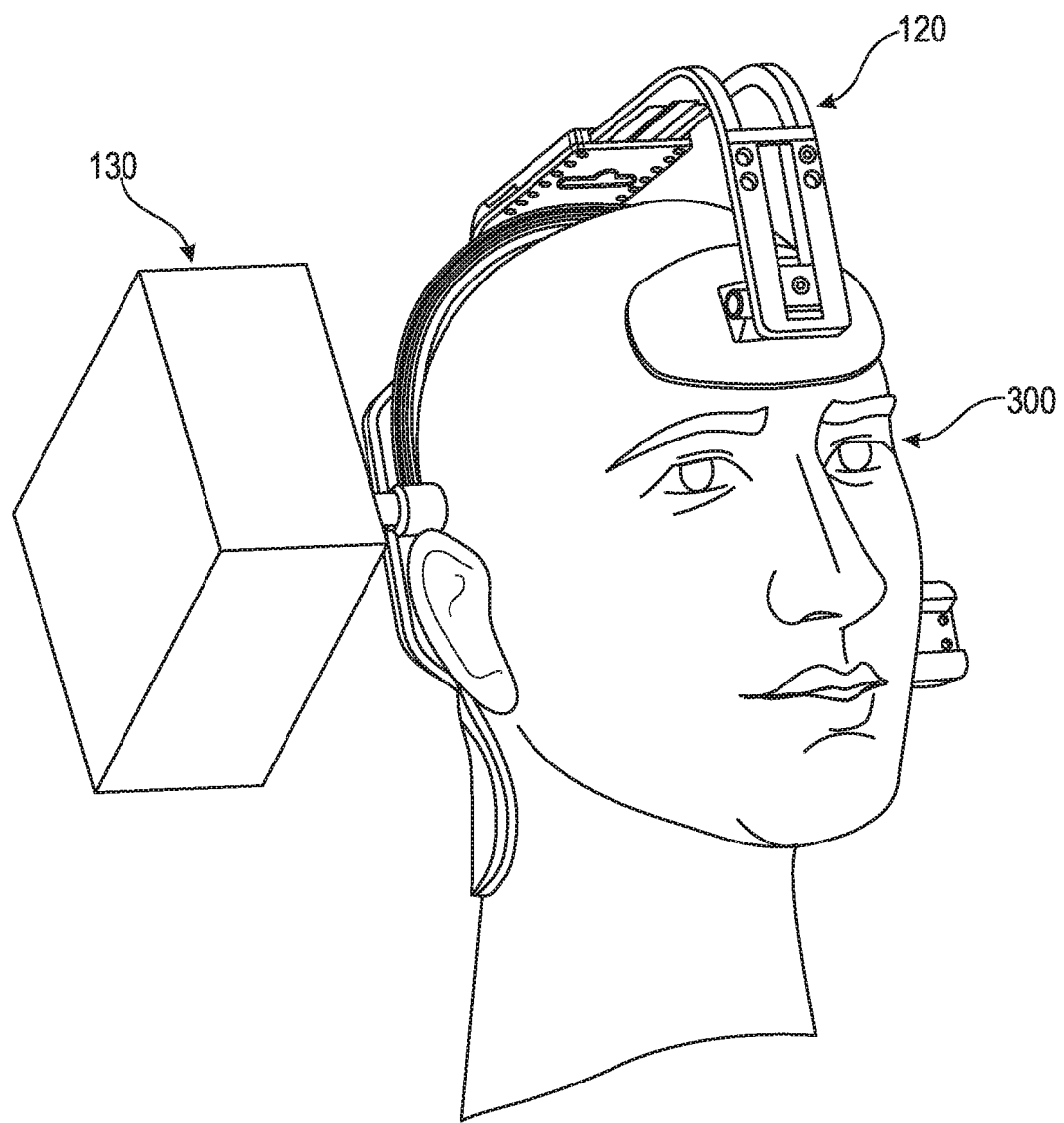
Figure 4A:
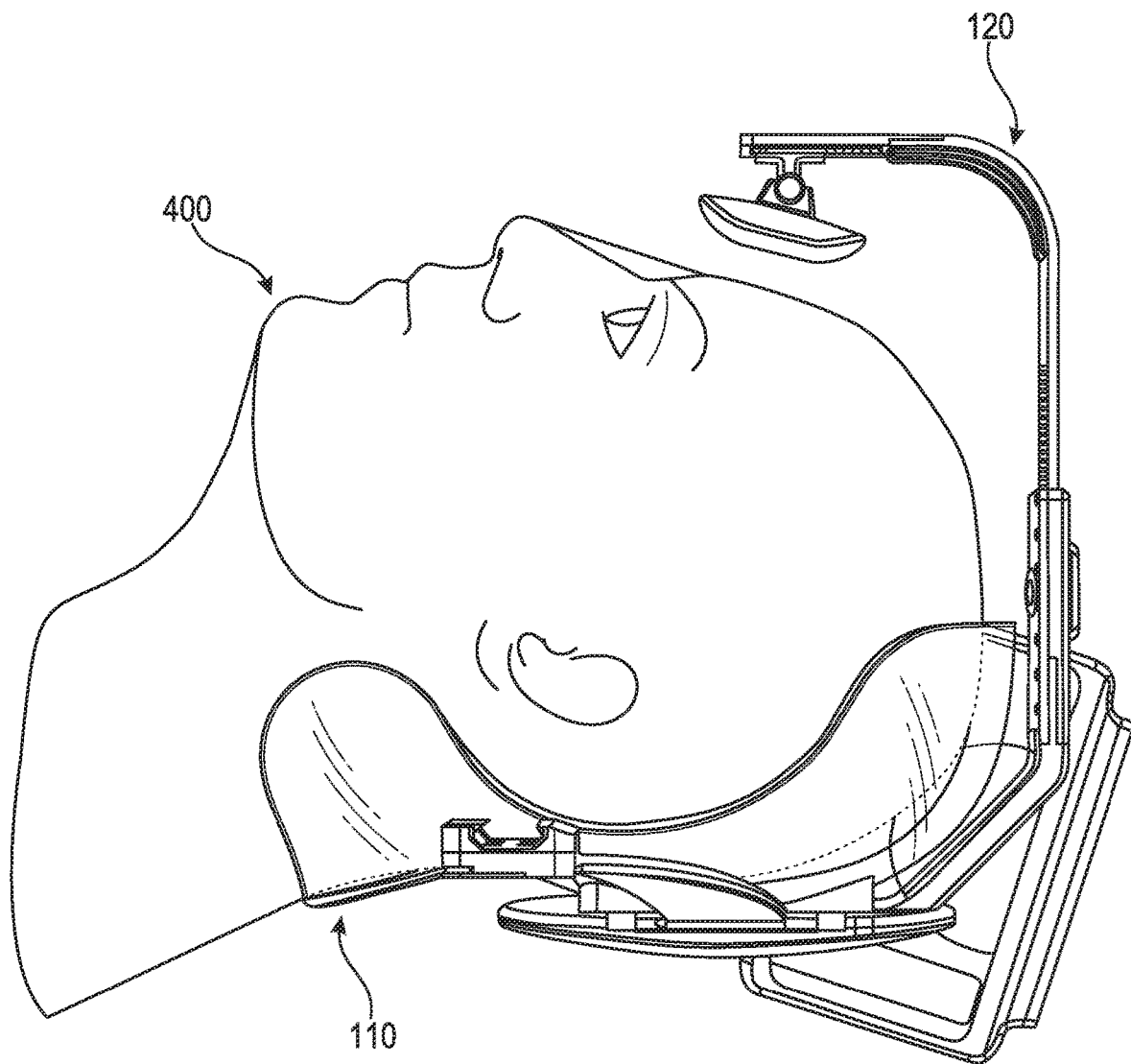
FIG. 4A and FIG. 4B illustrate views of the dynamic headset apparatus illustrated in FIGS. 1A-1G with a subject's head therein according to various arrangements.
Figure 4B:
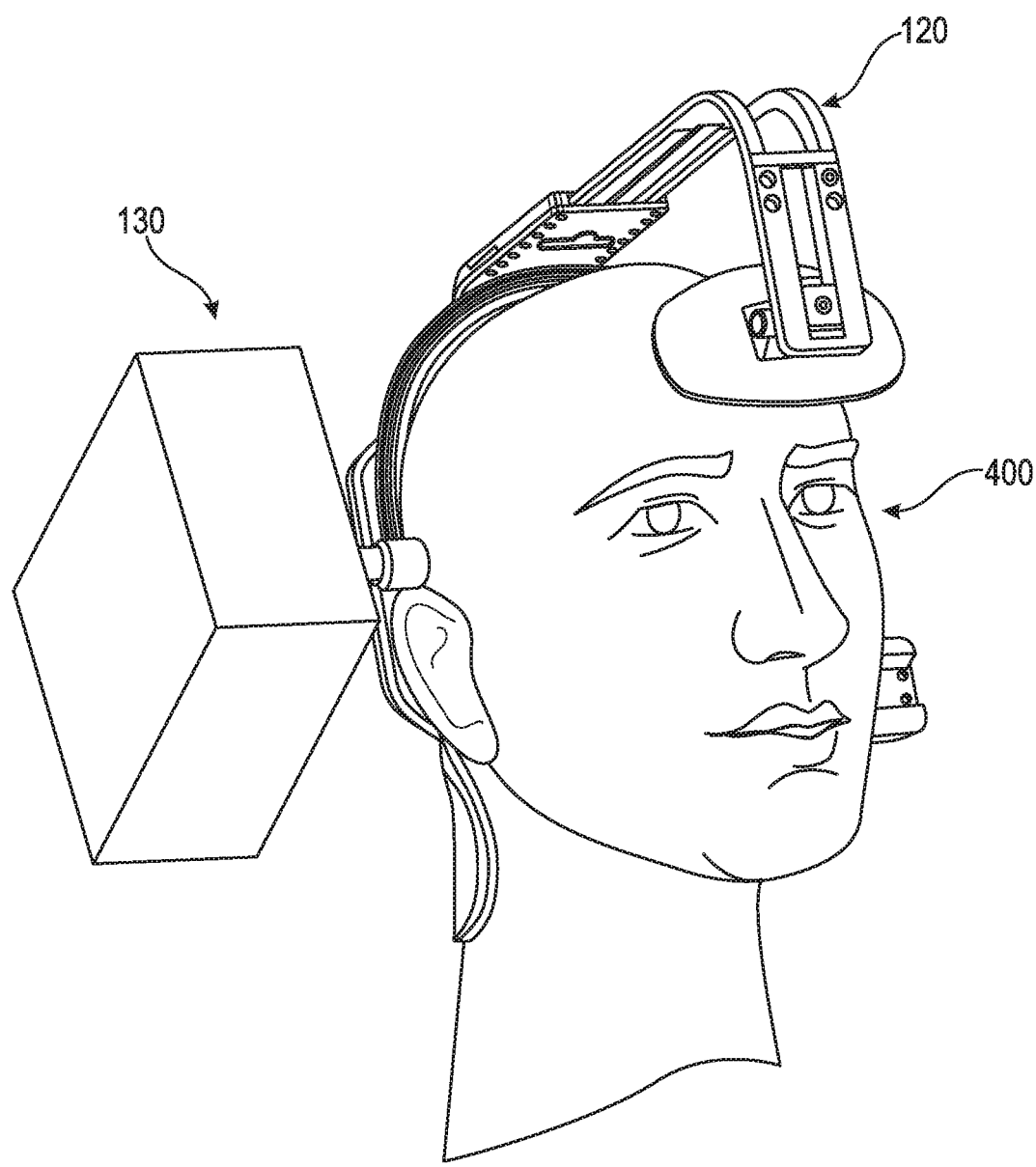

FIG. 3A and FIG. 3B illustrate views of the dynamic headset apparatus 100 illustrated in FIGS. 1A-1G with a subject's head 300 therein according to various arrangements. FIG. 4A and FIG. 4B illustrate views of the dynamic headset apparatus 100 illustrated in FIGS. 1A-1G with a subject's head 400 therein according to various arrangements. The head 300 represents a male head that is larger than 99% of head sizes, while the head 400 represents a female head that is larger than only 1% of head sizes. FIGS. 3A, 3B, 4A, and 4B illustrate the versatility of the headset apparatus 100 that provides a system in which a wide range of head sizes can be accommodated and adequately operated on by the device 130. As shown, despite the large size difference of the heads 300 and 400, each of the heads 300 and 400 still remain adequately within range of the device 130 for being operated on by the device 130. In particular, the cradle 110 is capable of accommodating and supporting different head sizes for use in conjunction with the device 130.

Figure 5A:
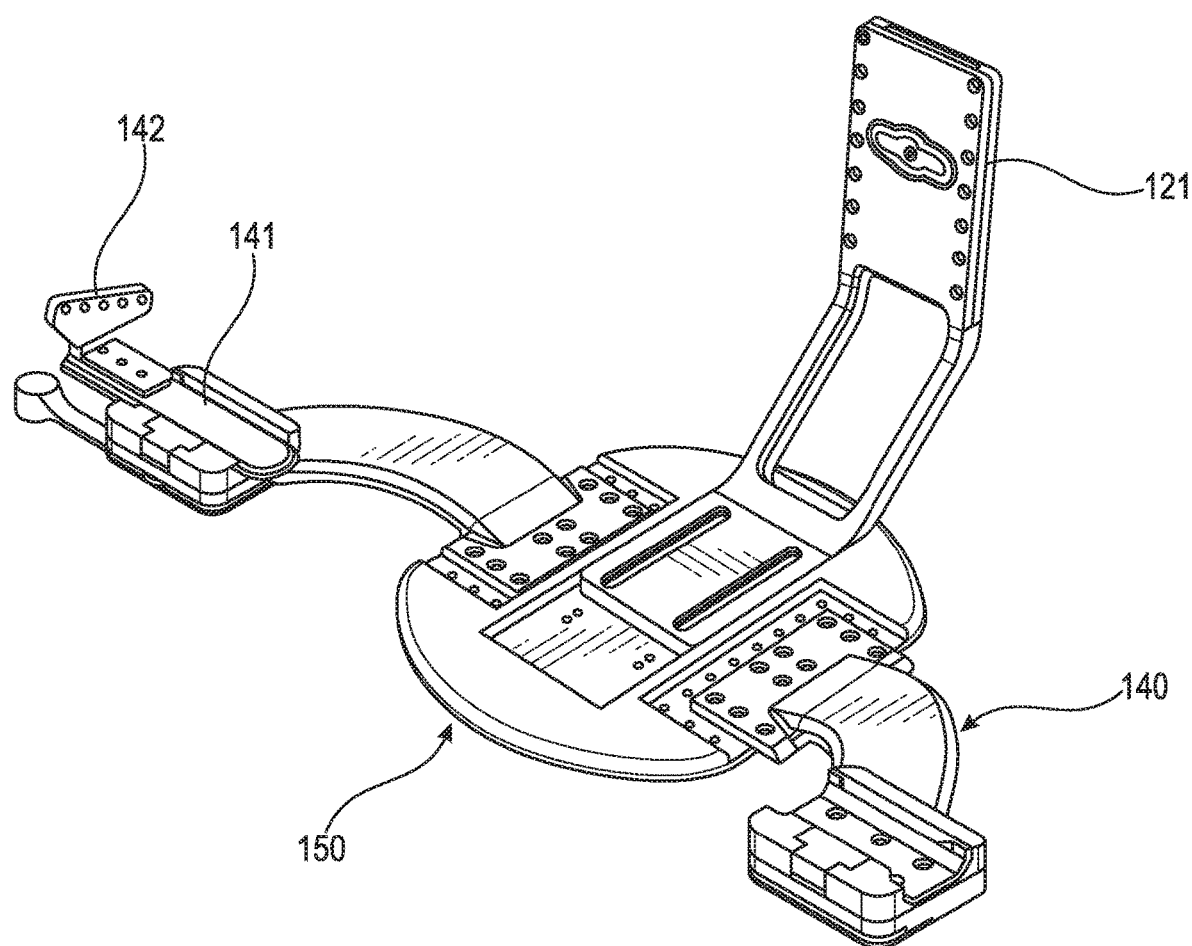
FIG. 5A and FIG. 5B illustrate a portion of the dynamic headset apparatus illustrated in FIGS. 1A-1G according to various arrangements.
Figure 5B:
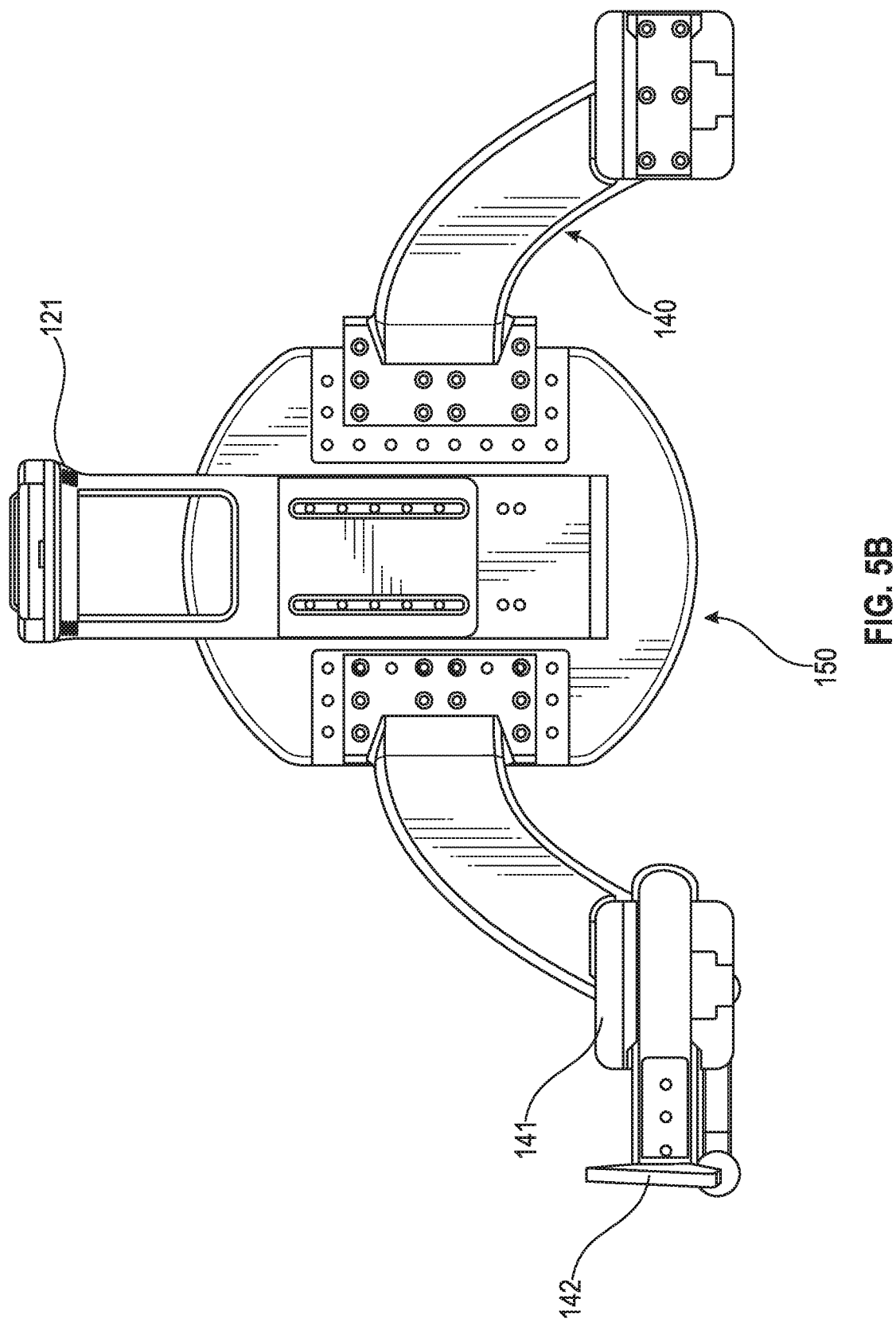
Figure 6B:
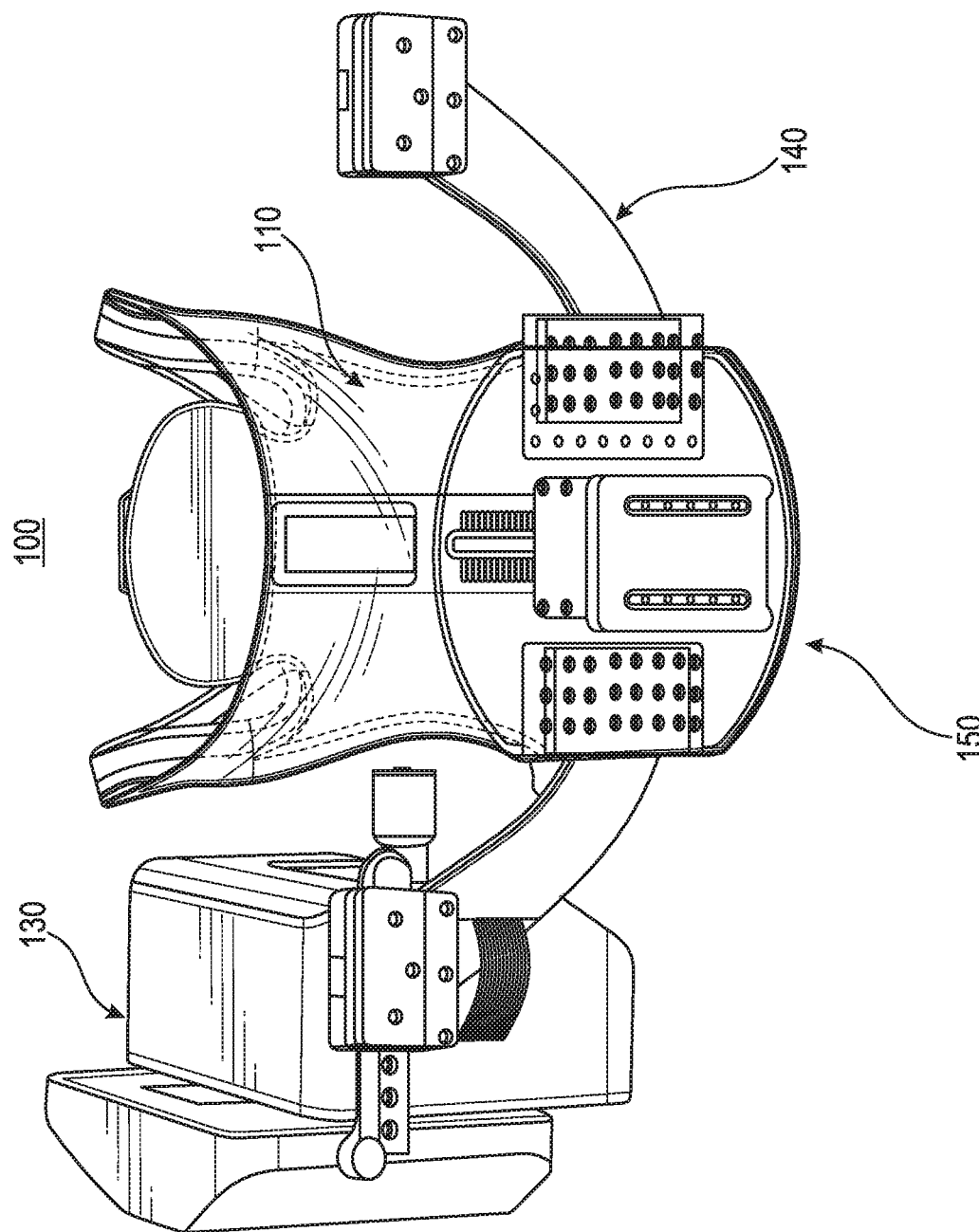
Figure 7A:
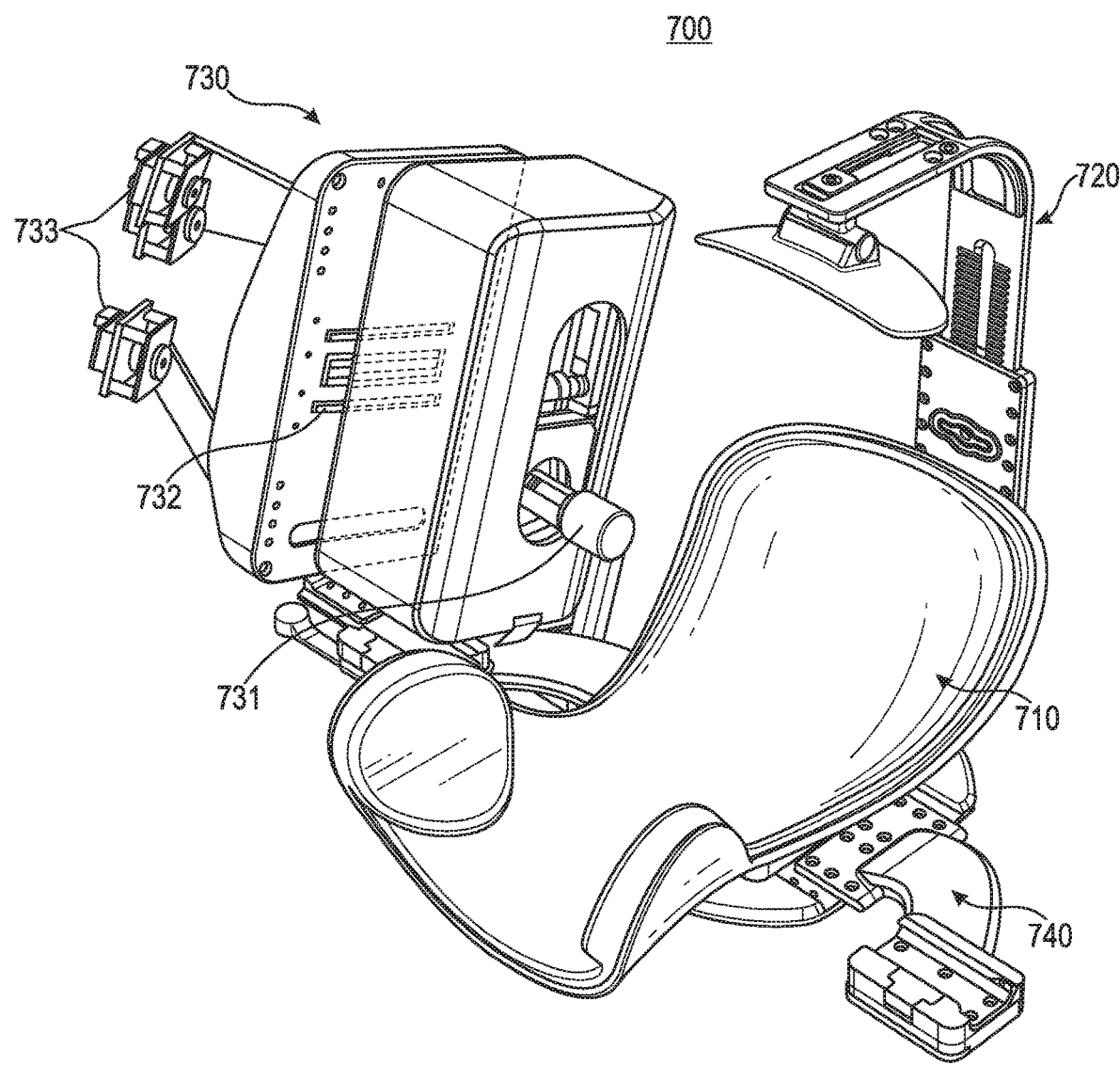
FIG. 7A, FIG. 7B, FIG. 7C, FIG. 7D, FIG. 7E, and FIG. 7F illustrate various views of a dynamic headset apparatus including a device coupled thereto according to various arrangements.
Figure 7B:
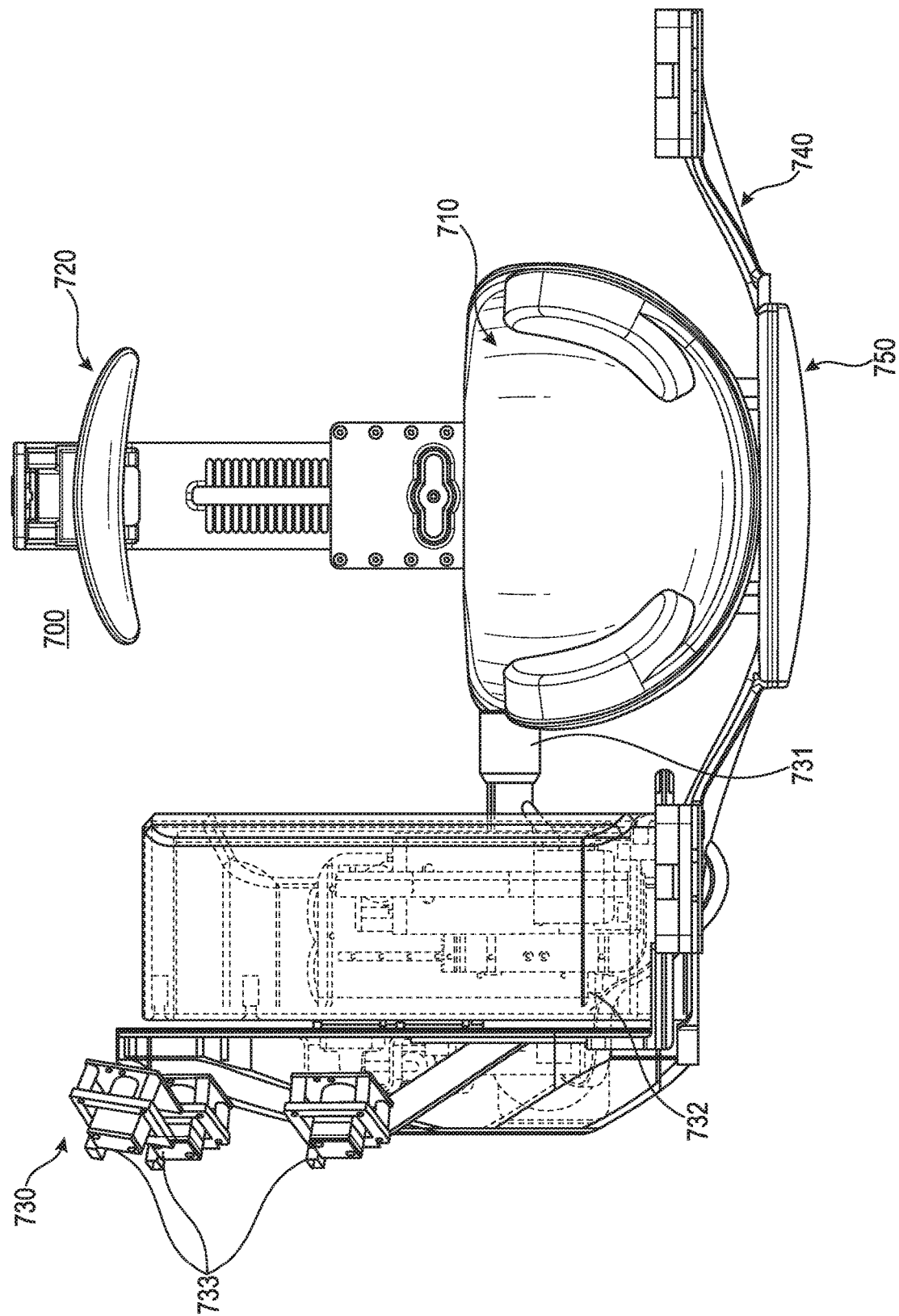
Figure 7C:
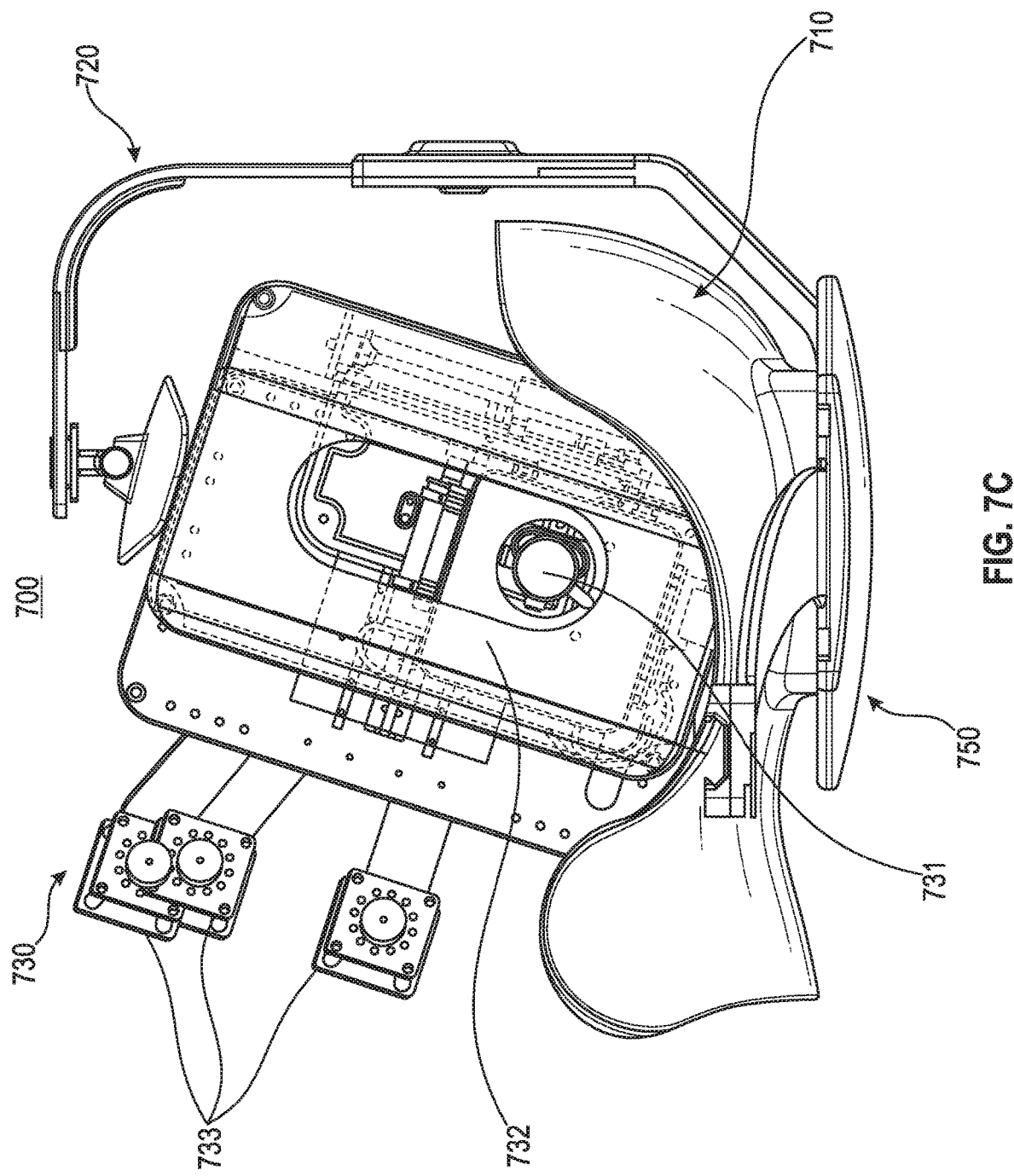
Figure 7D:
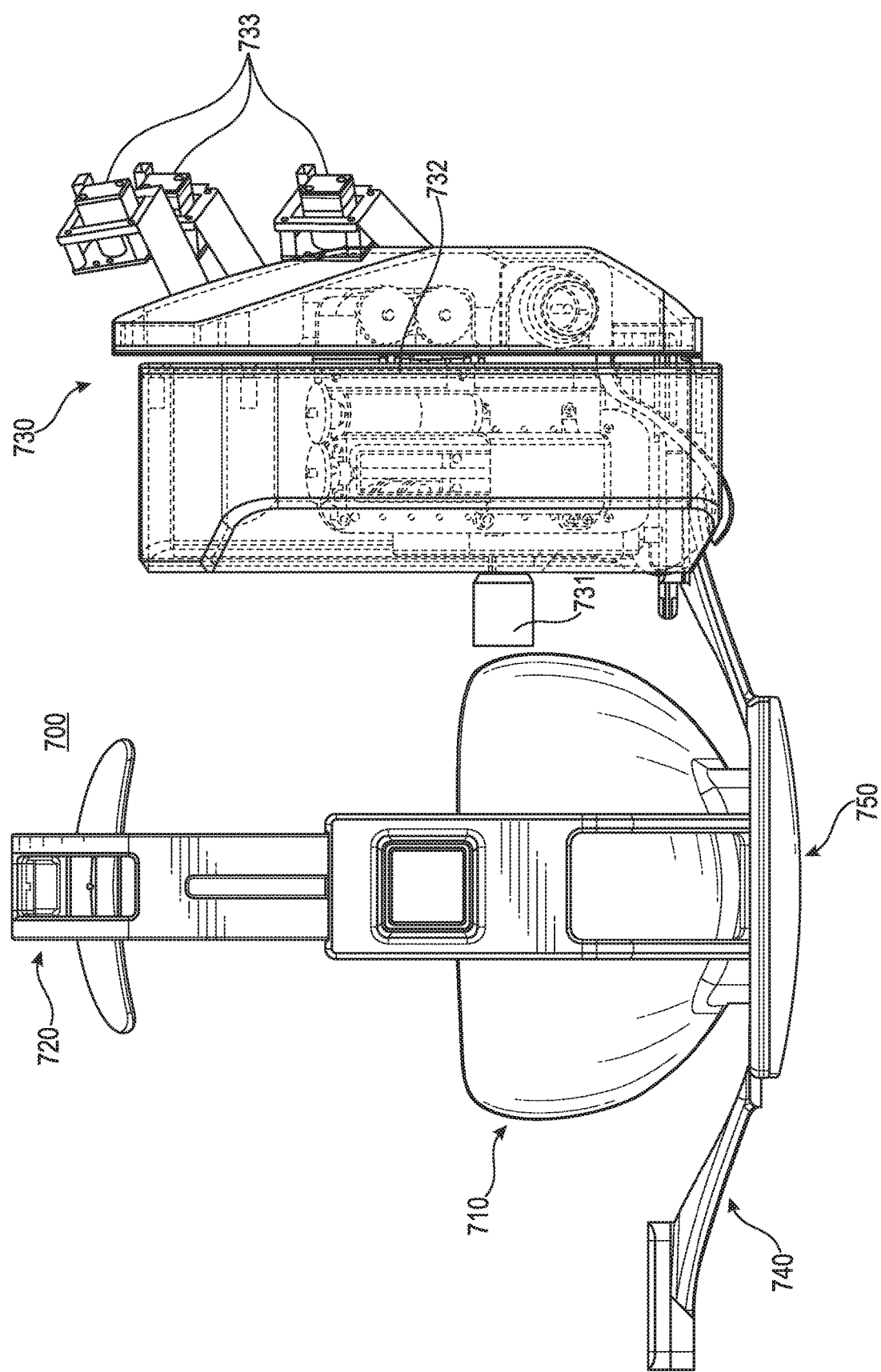
Figure 7E:
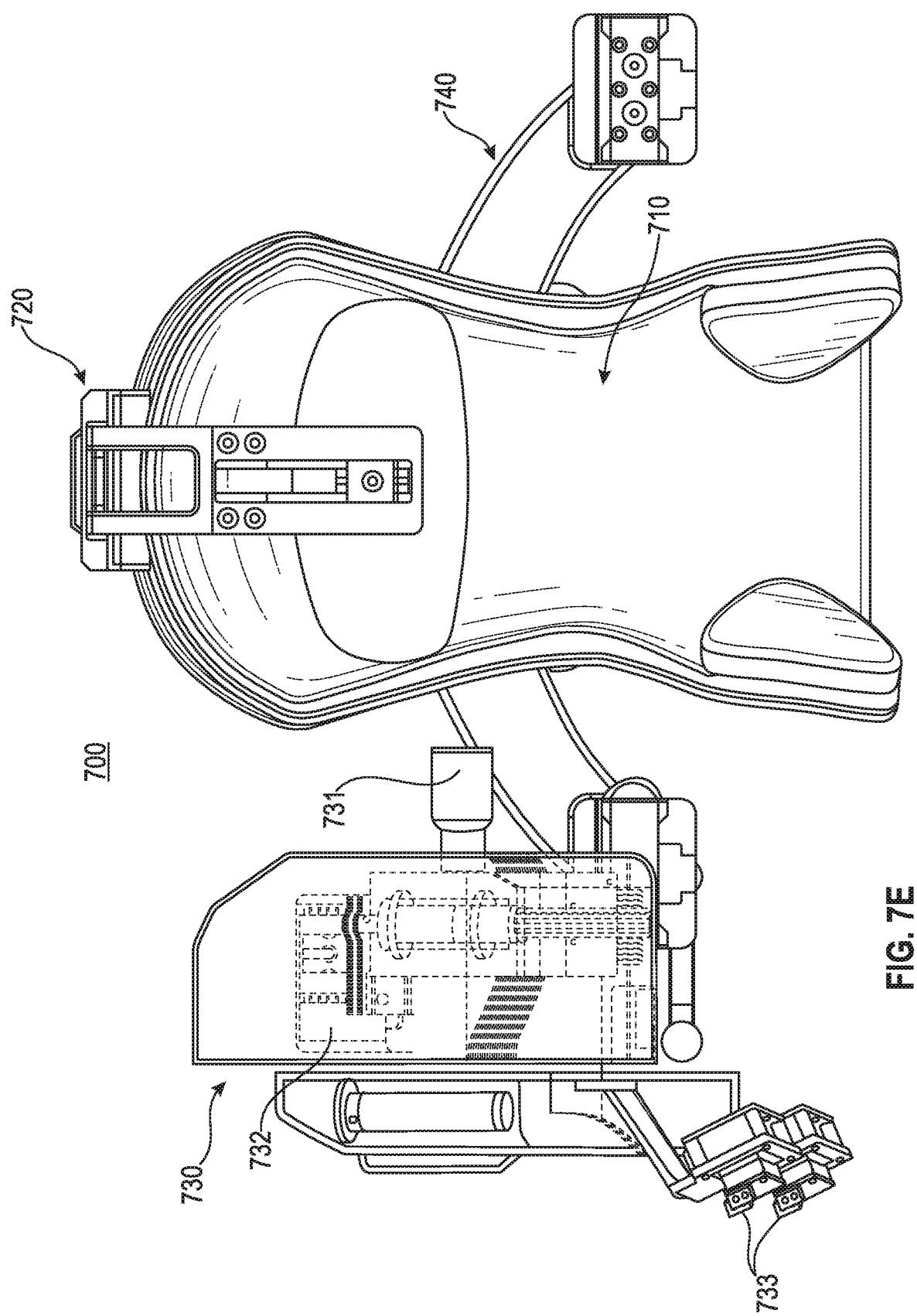
Figure 7F:
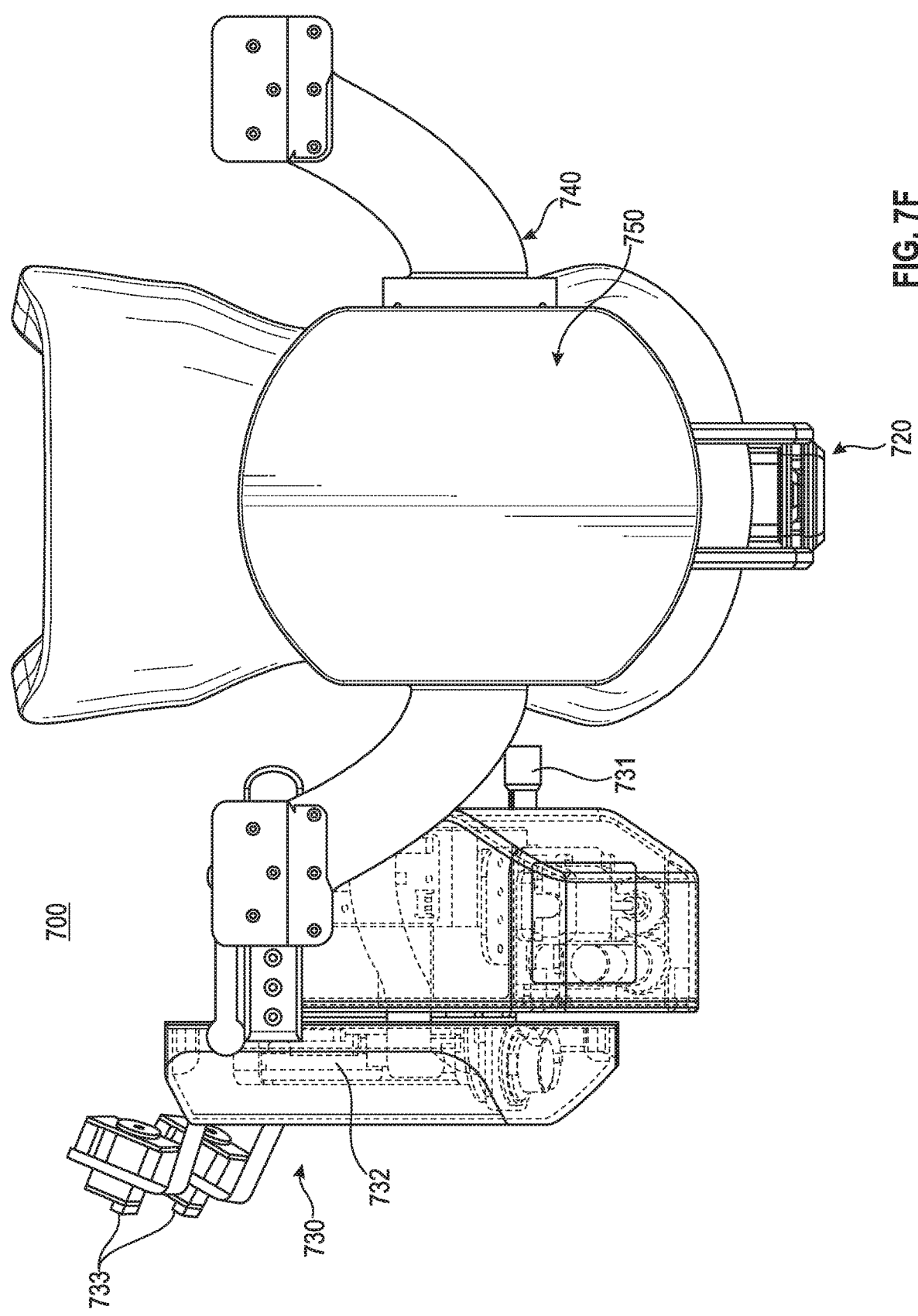
Figure 8A:
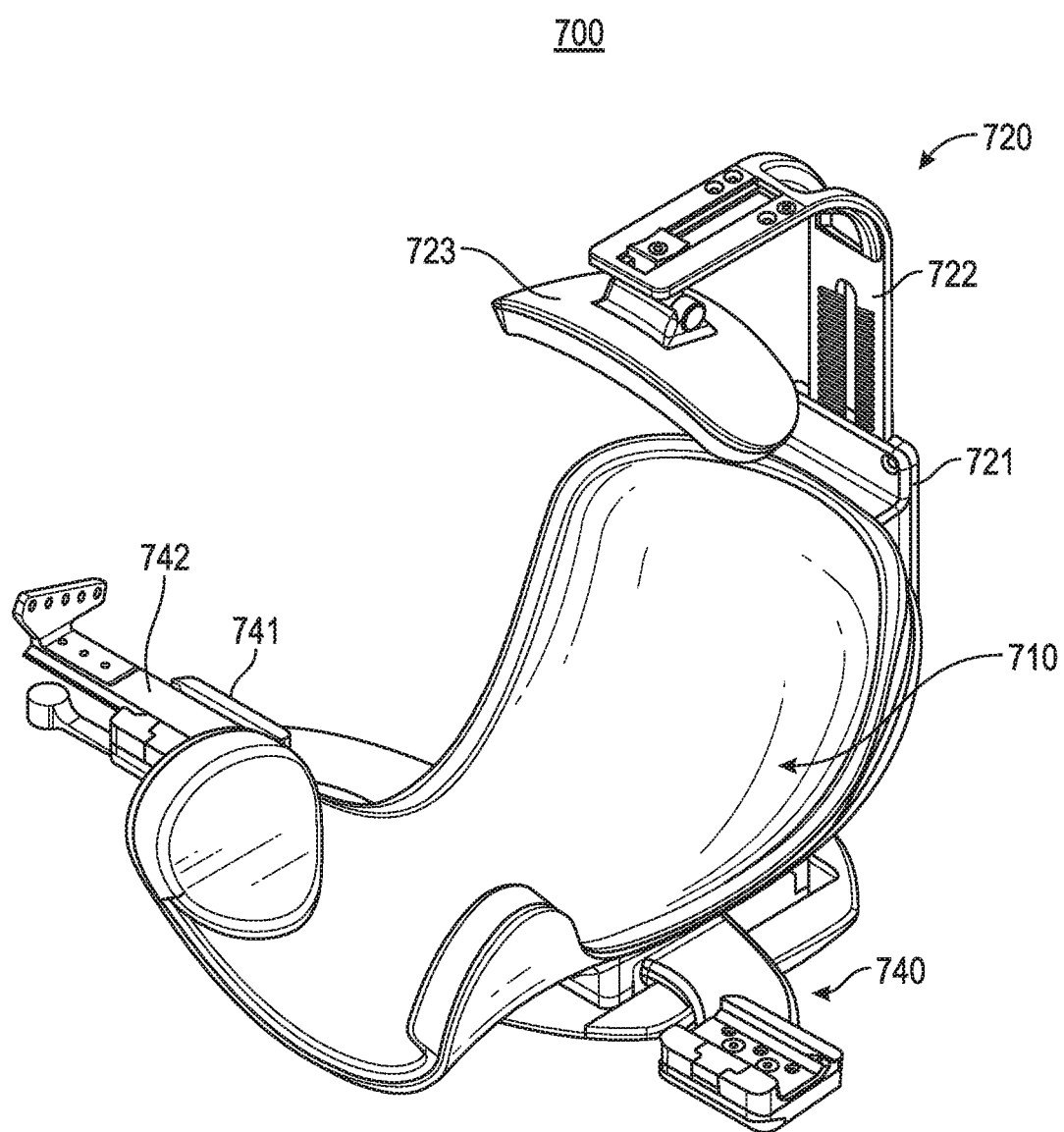
FIG. 8A, FIG. 8B, FIG. 8C, FIG. 8D, FIG. 8E, FIG. 8F, and FIG. 8G illustrate various views of the dynamic headset apparatus illustrated in FIGS. 7A-7F, without the coupled device, according to various arrangements.
Figure 8B:
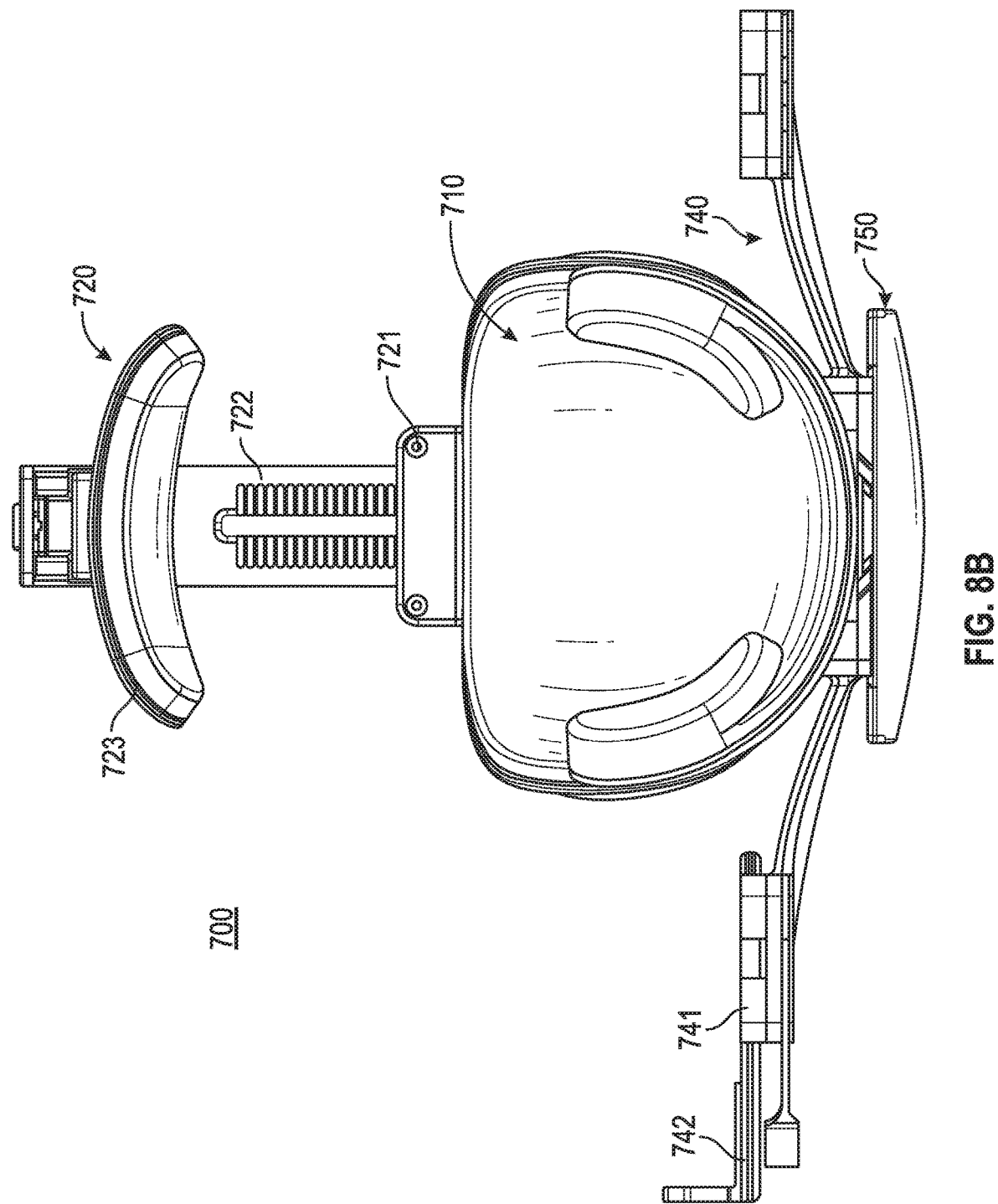
Figure 8C:
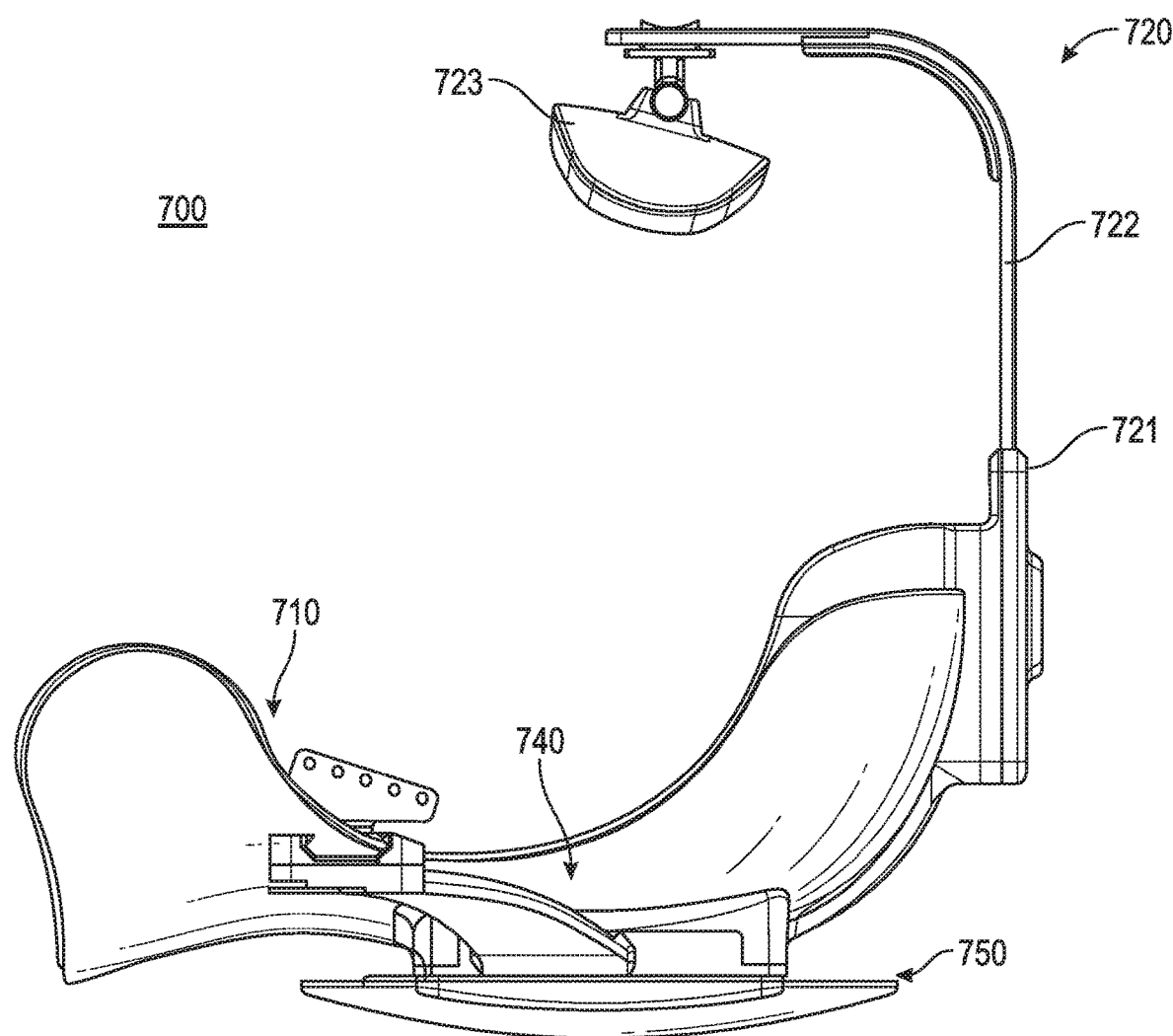
Figure 8D:
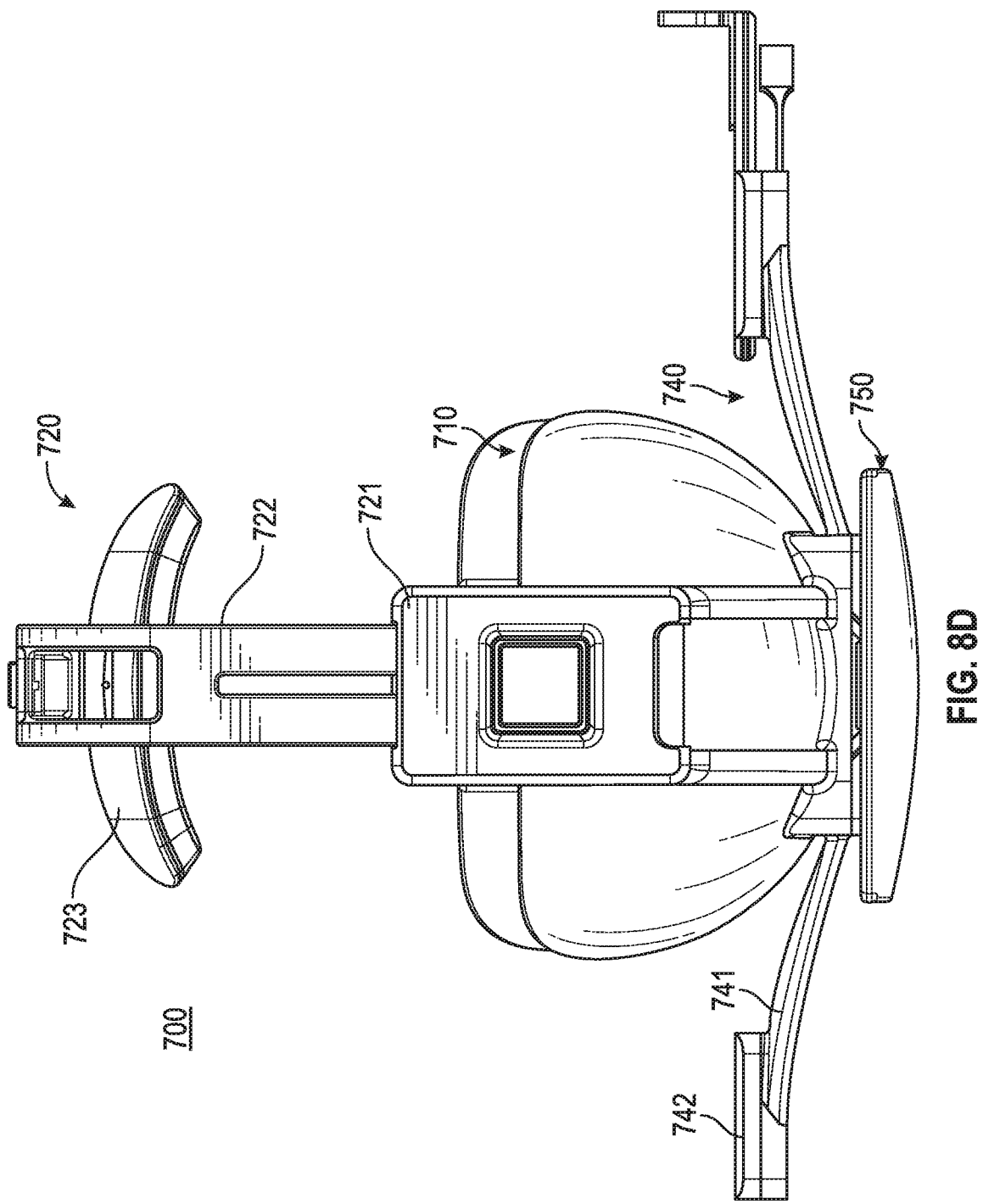
Figure 8E:
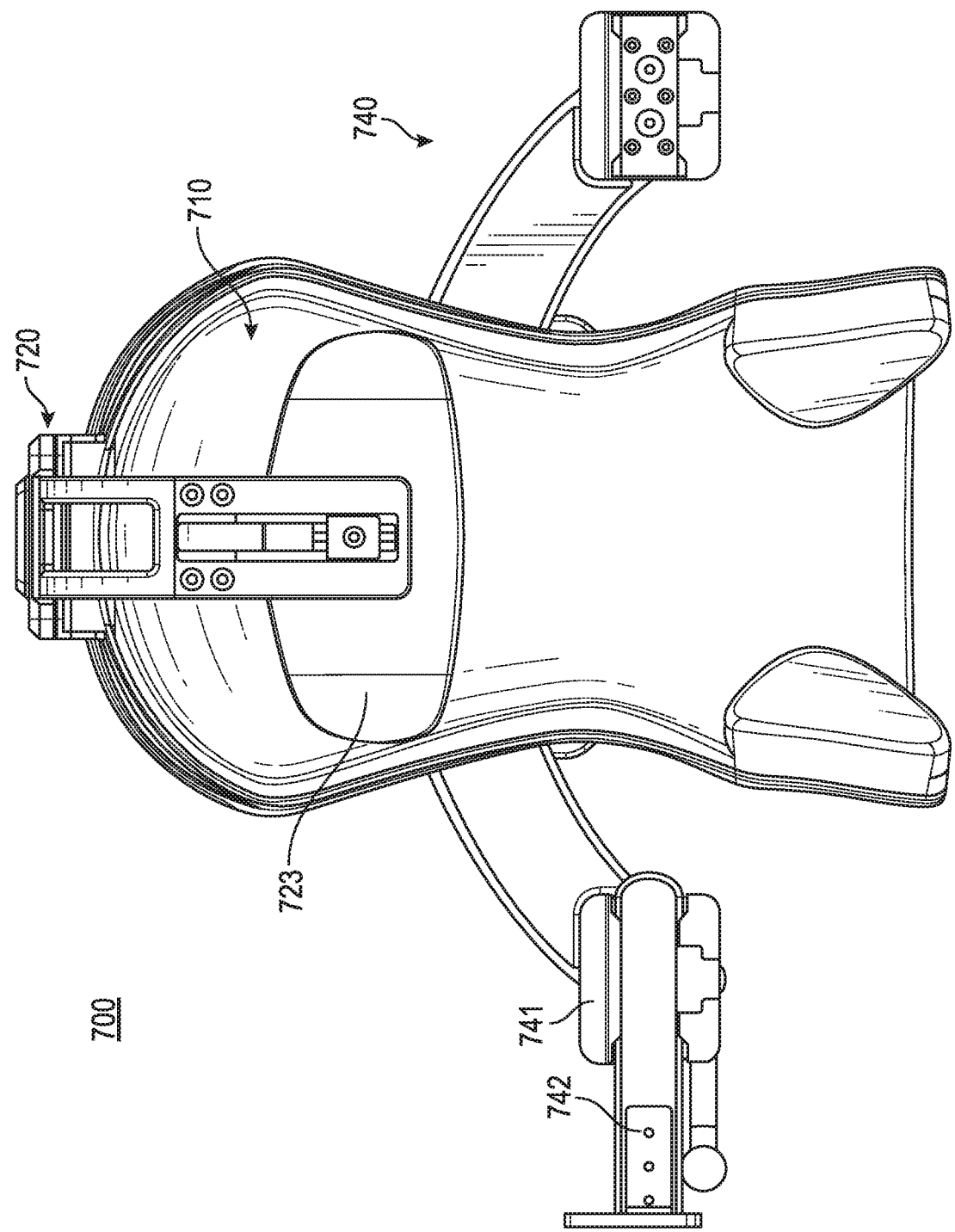
Figure 8F:
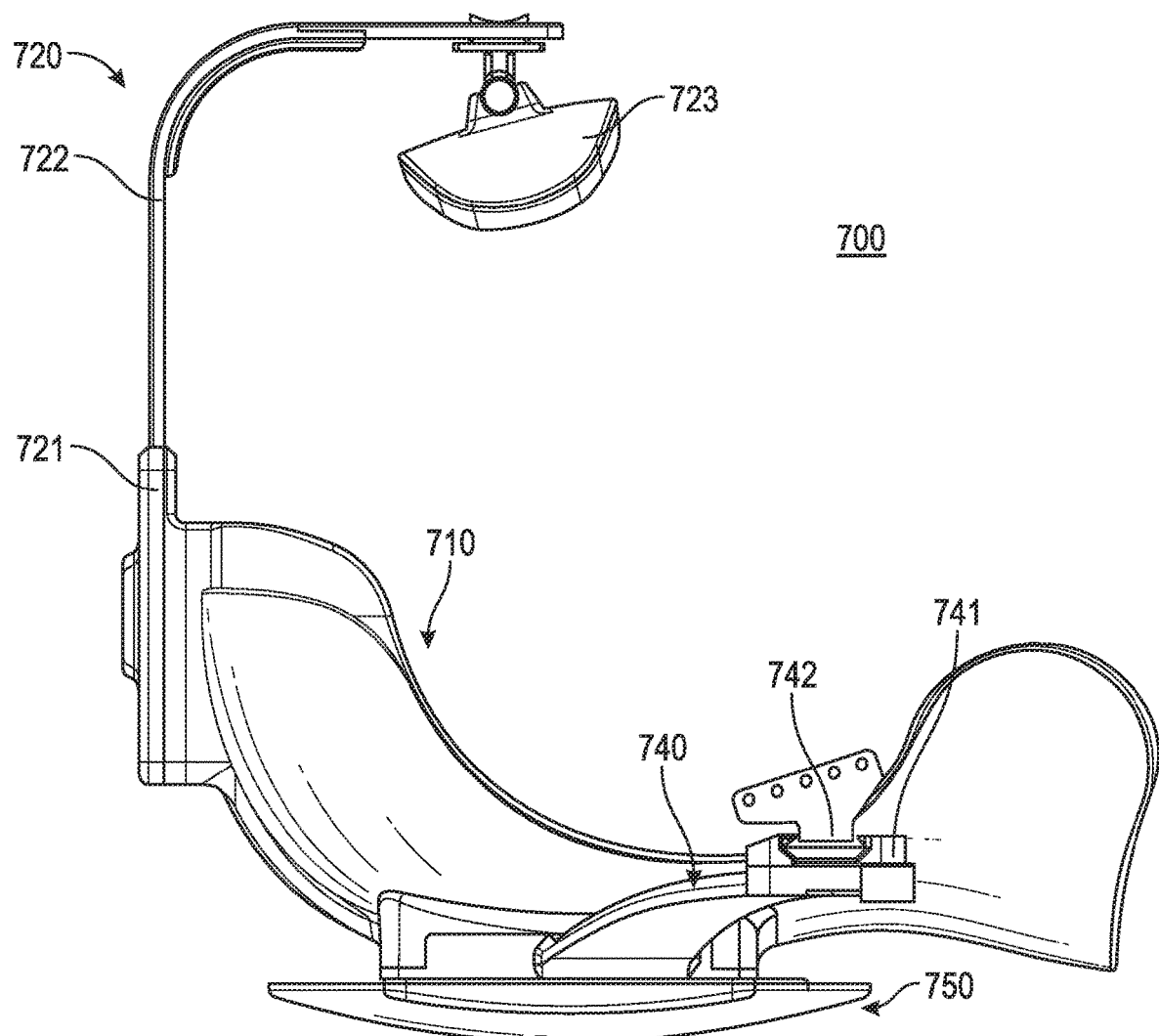
Figure 8G:
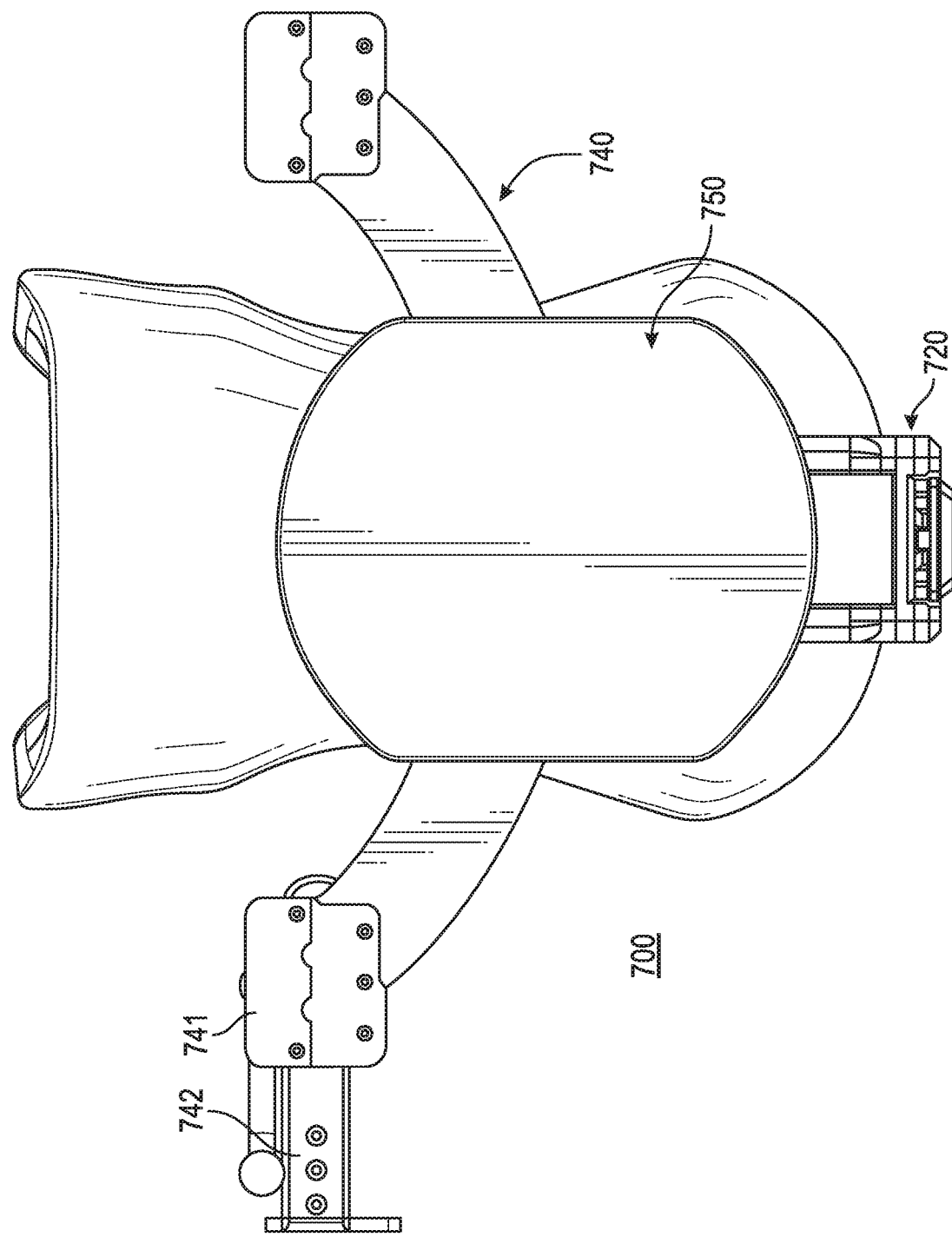
Figure 9A:
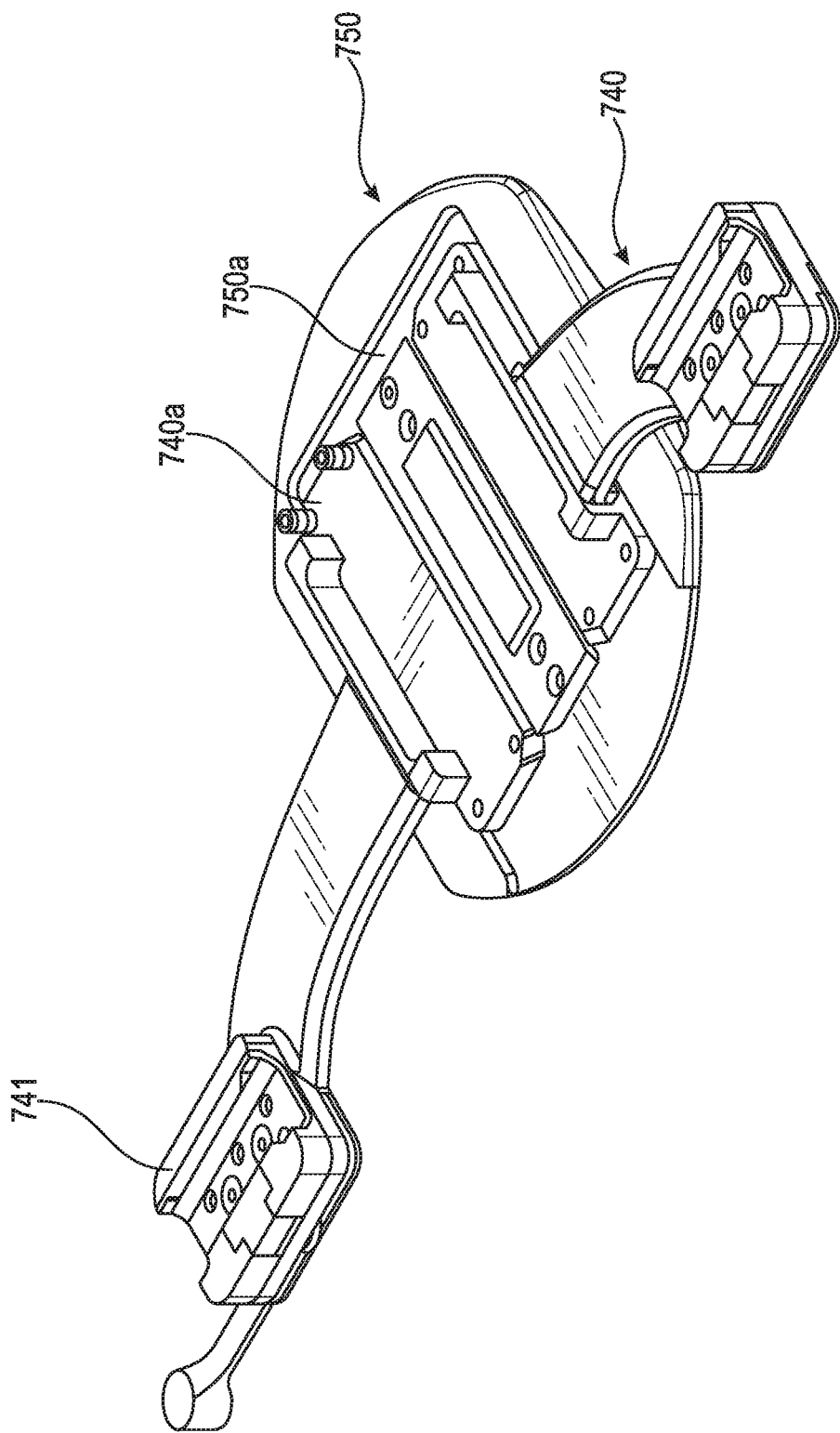
FIG. 9A, FIG. 9B, FIG. 9C, and FIG. 9D illustrate a portion of the dynamic headset apparatus illustrated in FIGS. 7A-7F according to various arrangements.
Figure 9B:
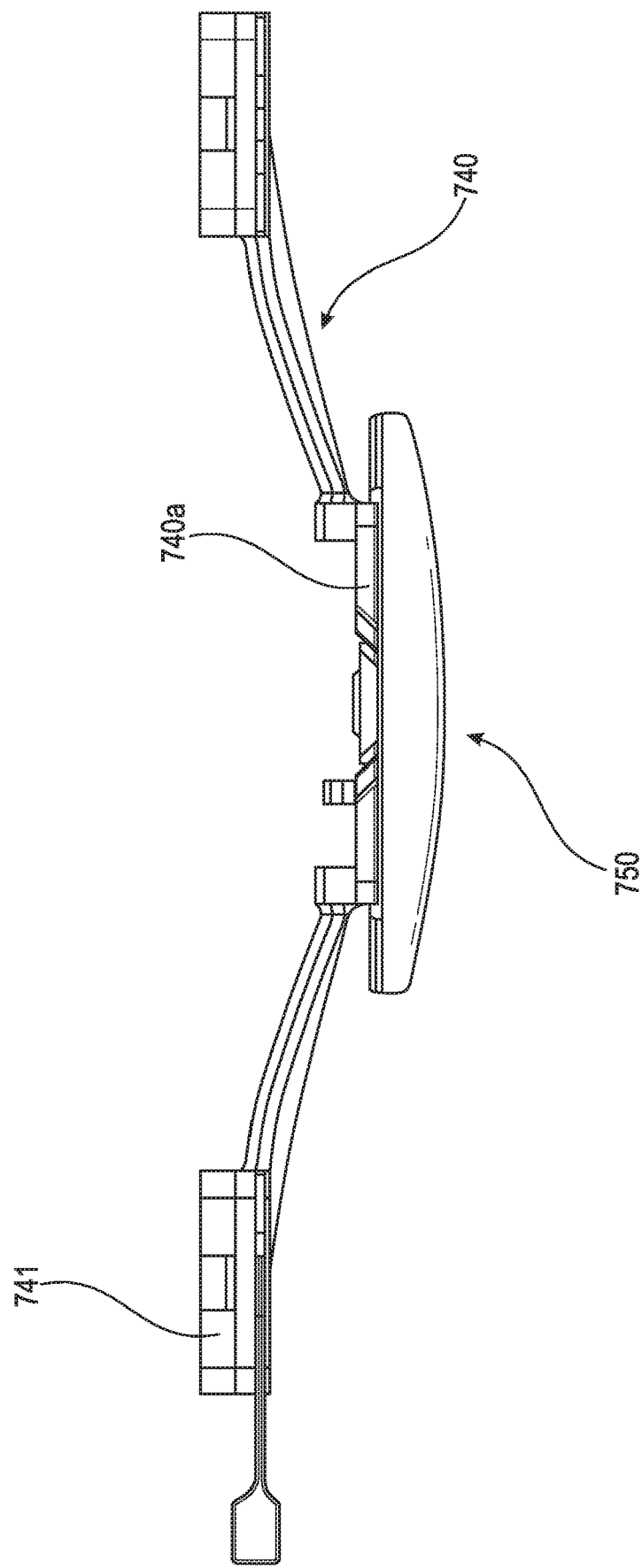
Figure 9C:
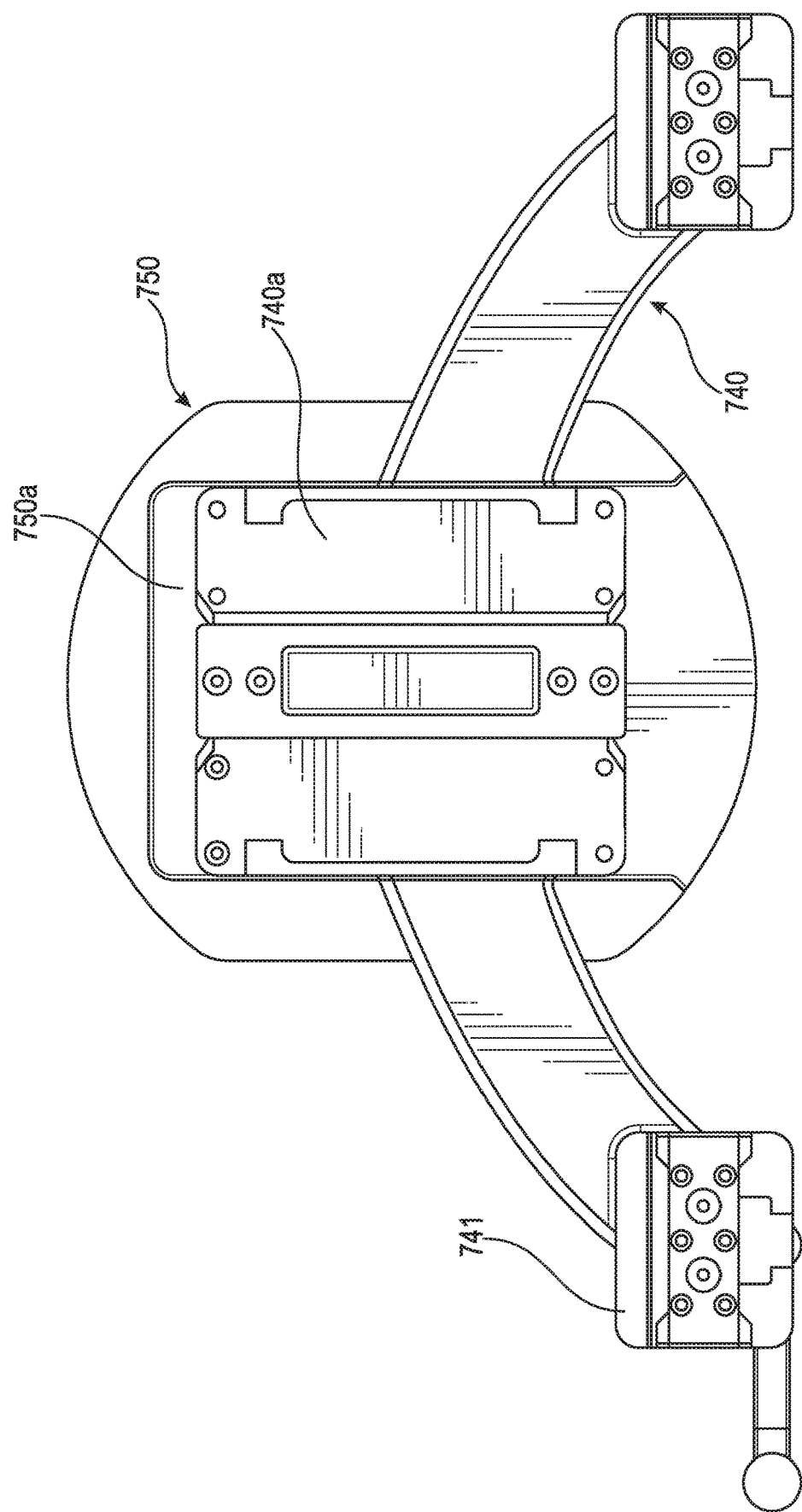
Figure 9D:
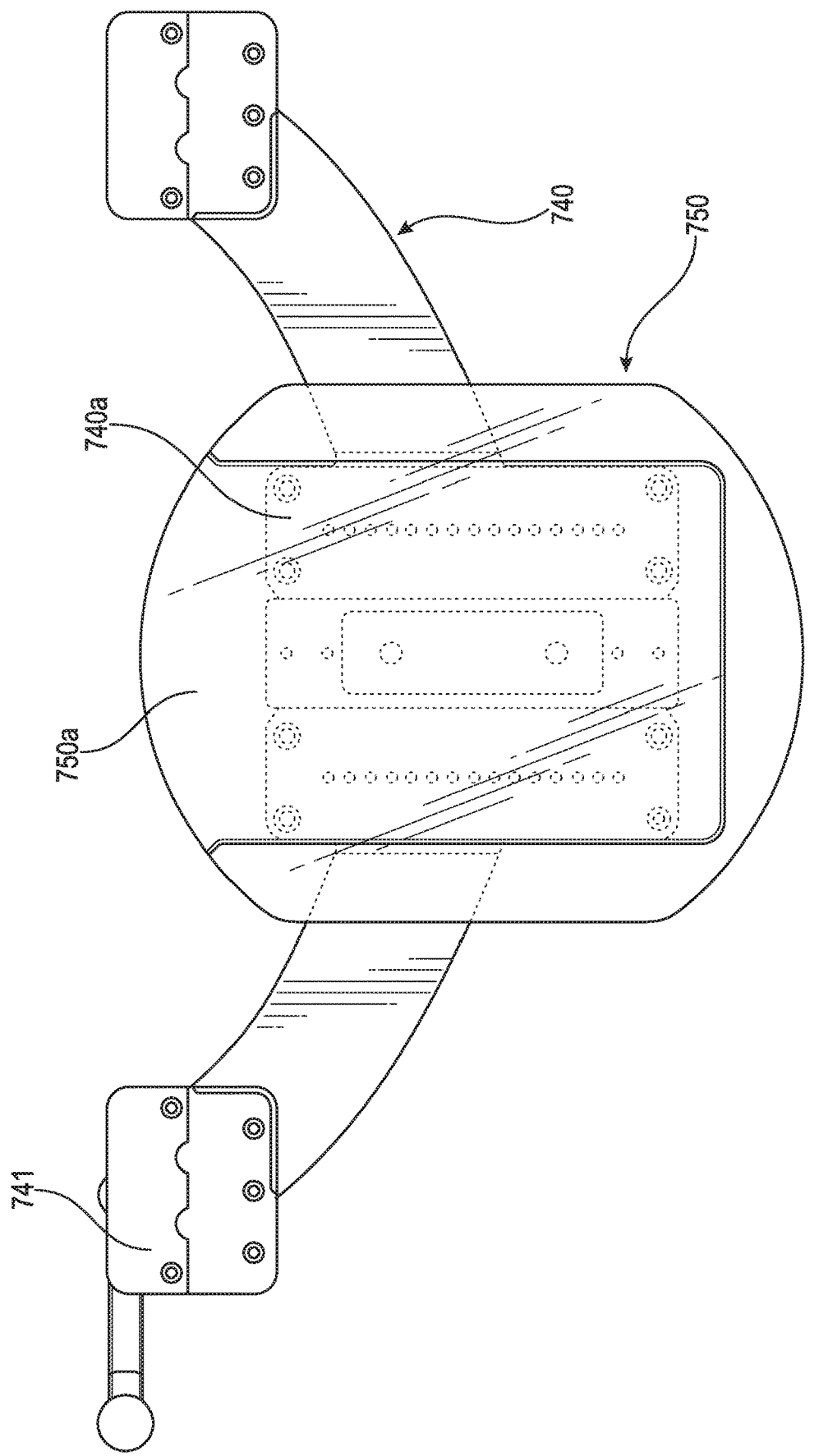
Figure 10A:
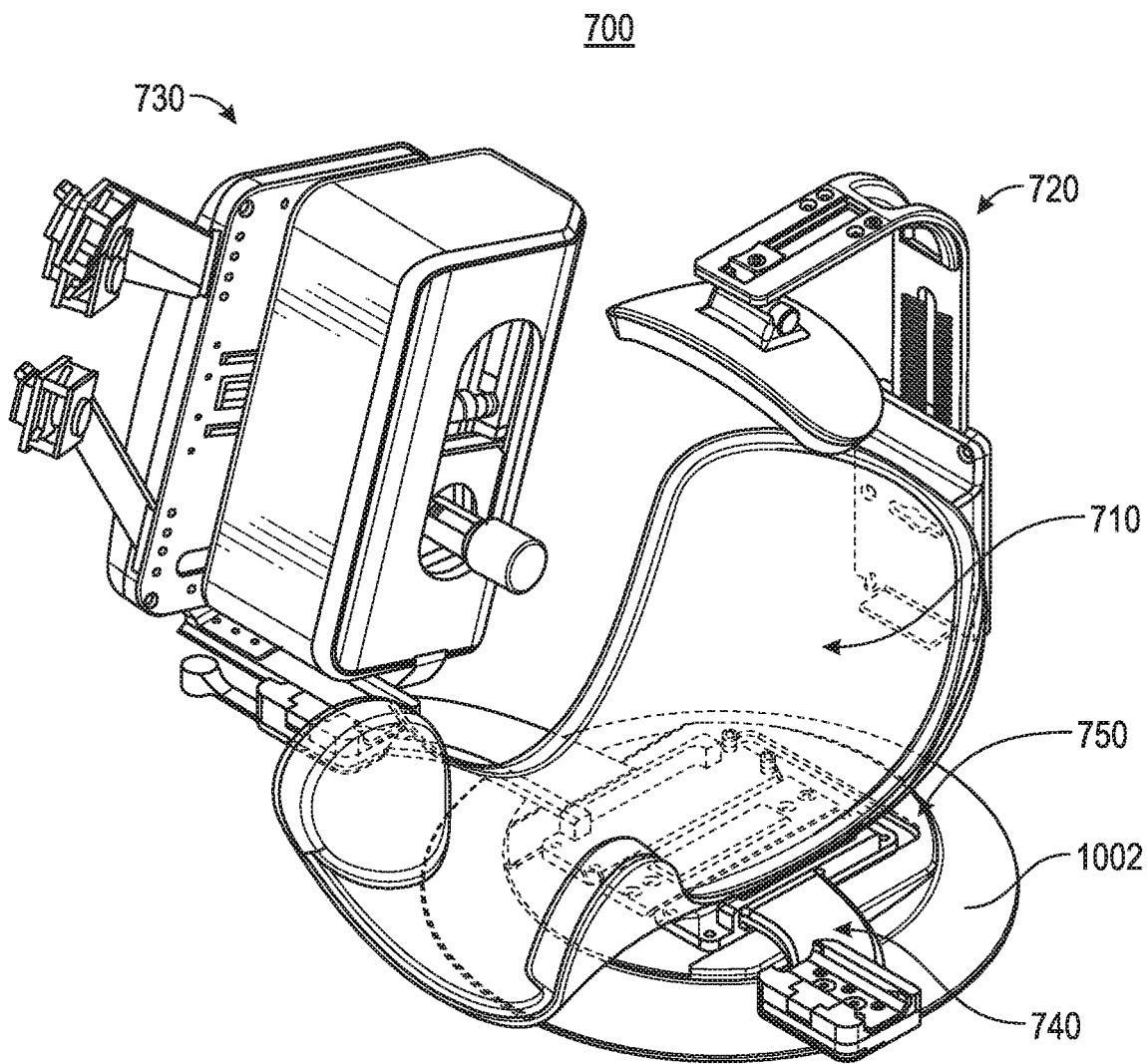
FIG. 10A, FIG. 10B, FIG. 10C, and FIG. 10D illustrate a rotation base contacting the dynamic headset apparatus illustrated in FIGS. 7A-7F according to various arrangements.
Figure 10B:
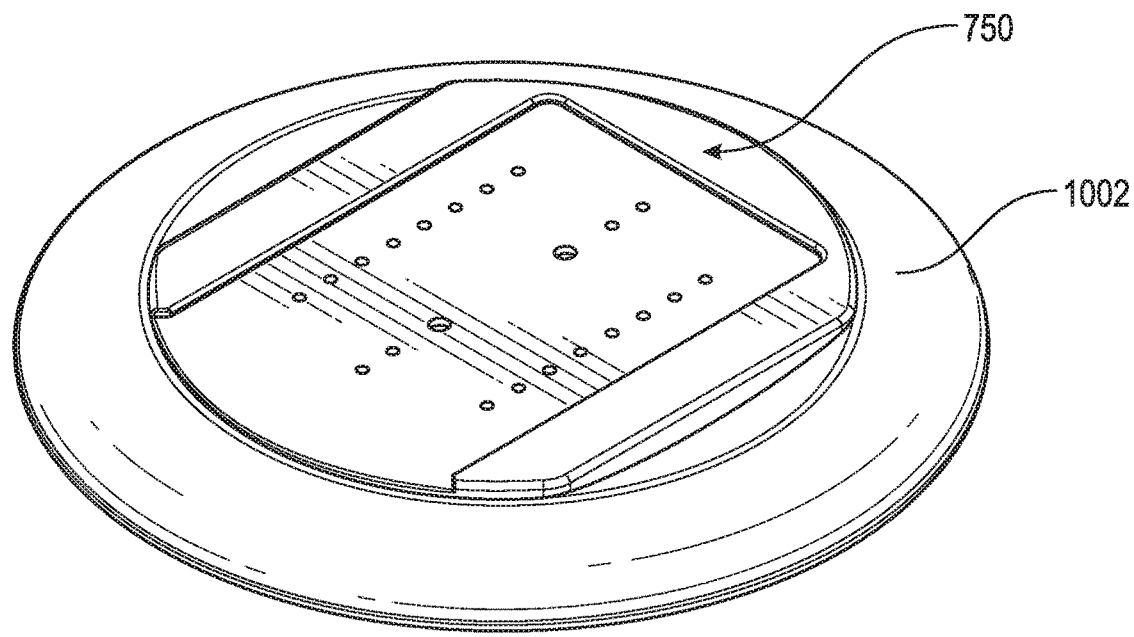
Figure 10C:
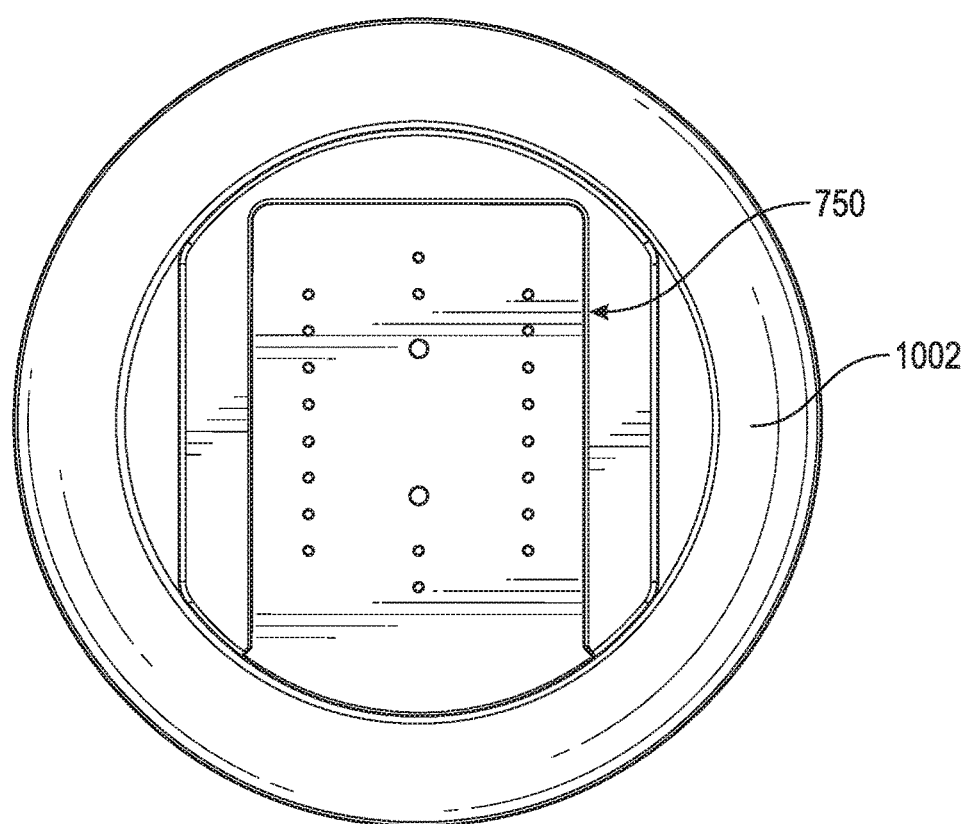
Figure 10D:
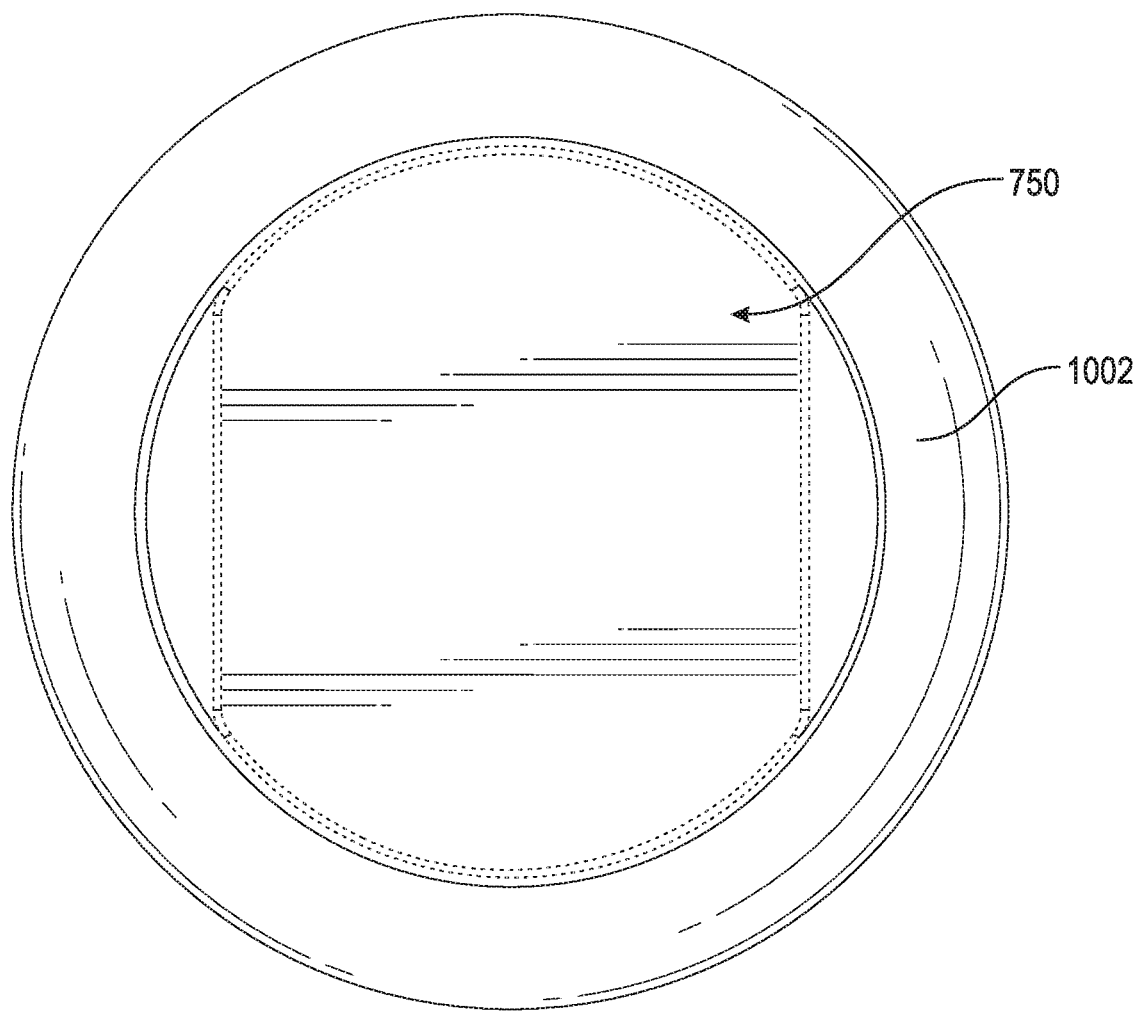
Figure 11A:
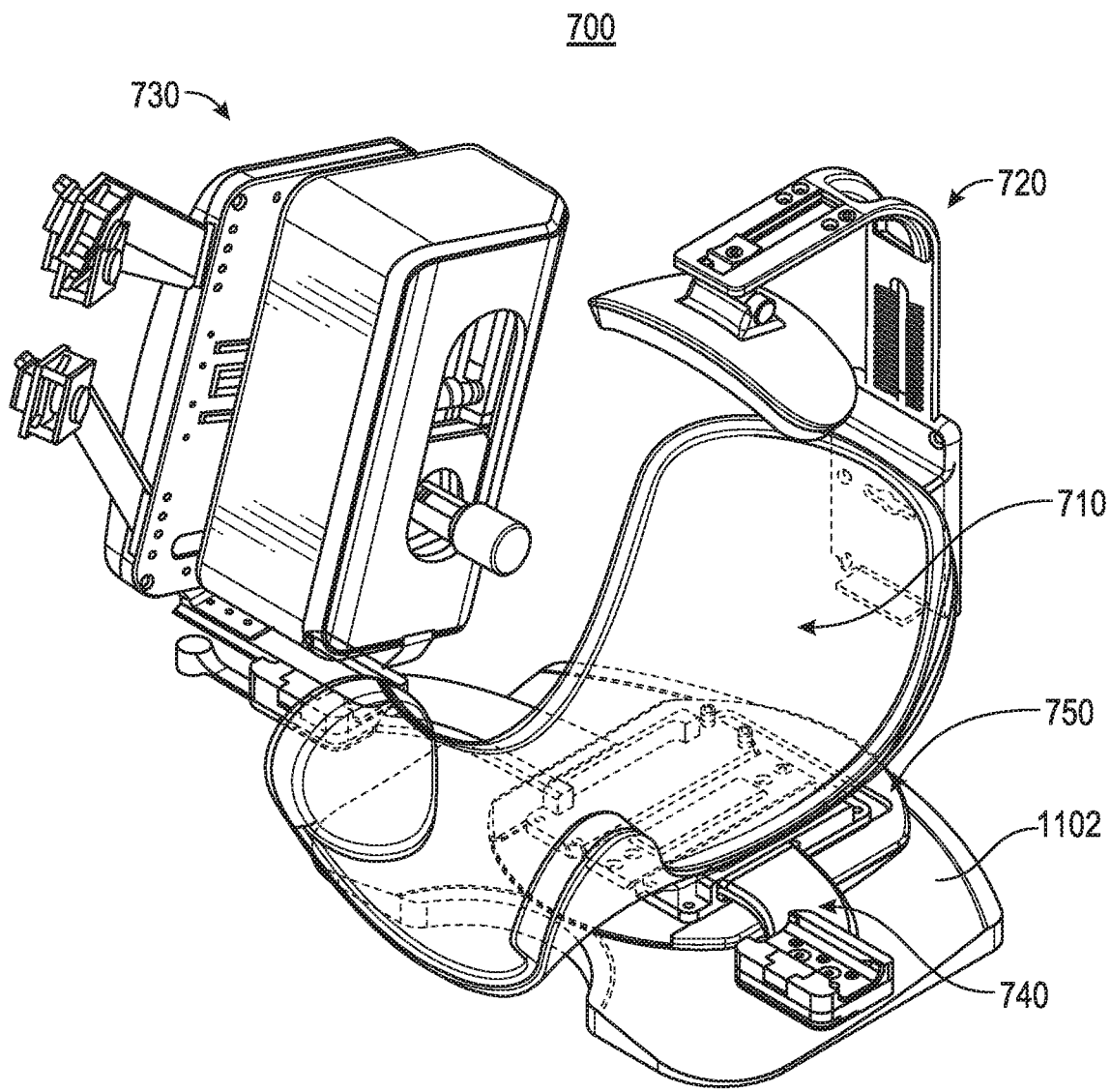
FIG. 11A, FIG. 11B, FIG. 11C, and FIG. 11D illustrate a slide base contacting the dynamic headset apparatus illustrated in FIGS. 7A-7F according to various arrangements.
Figure 11B:
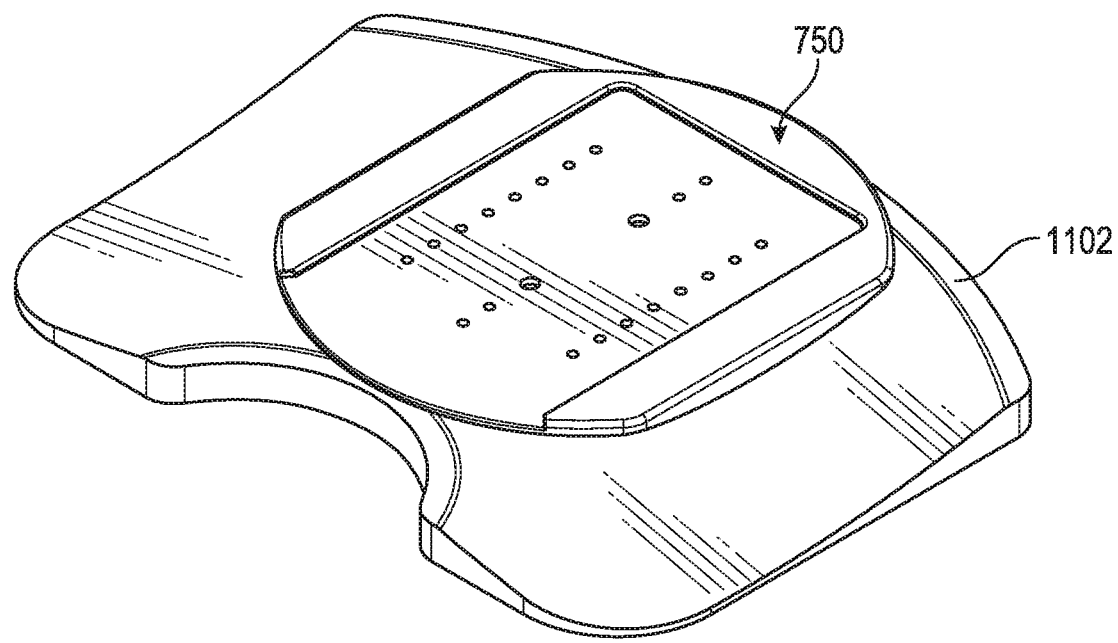
Figure 11C:
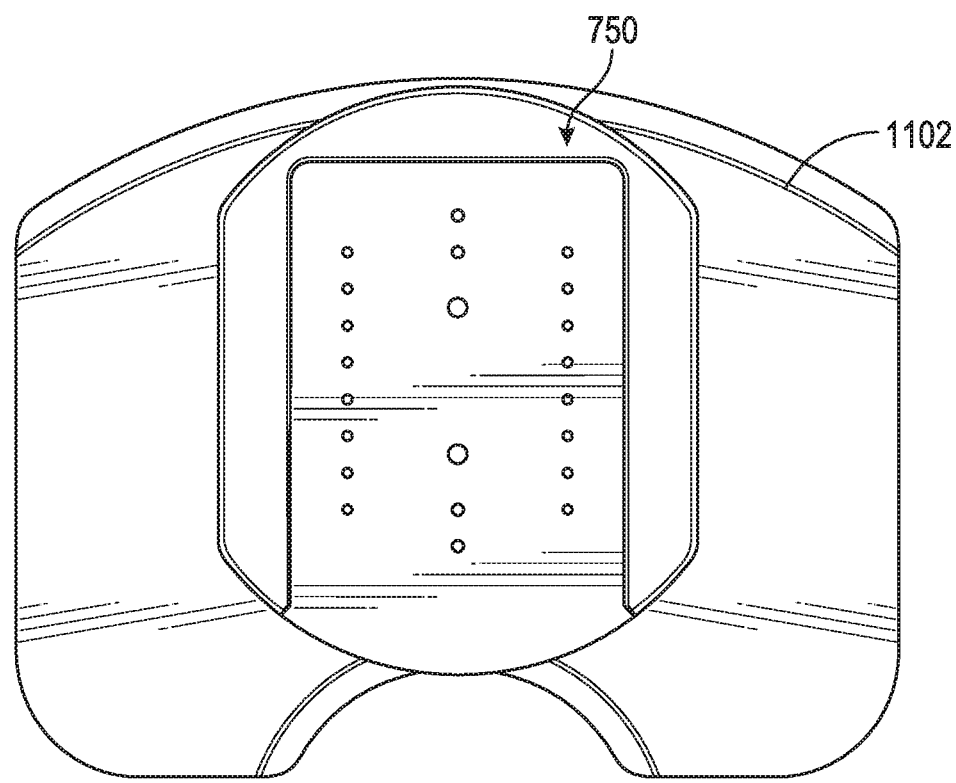
Figure 11D:
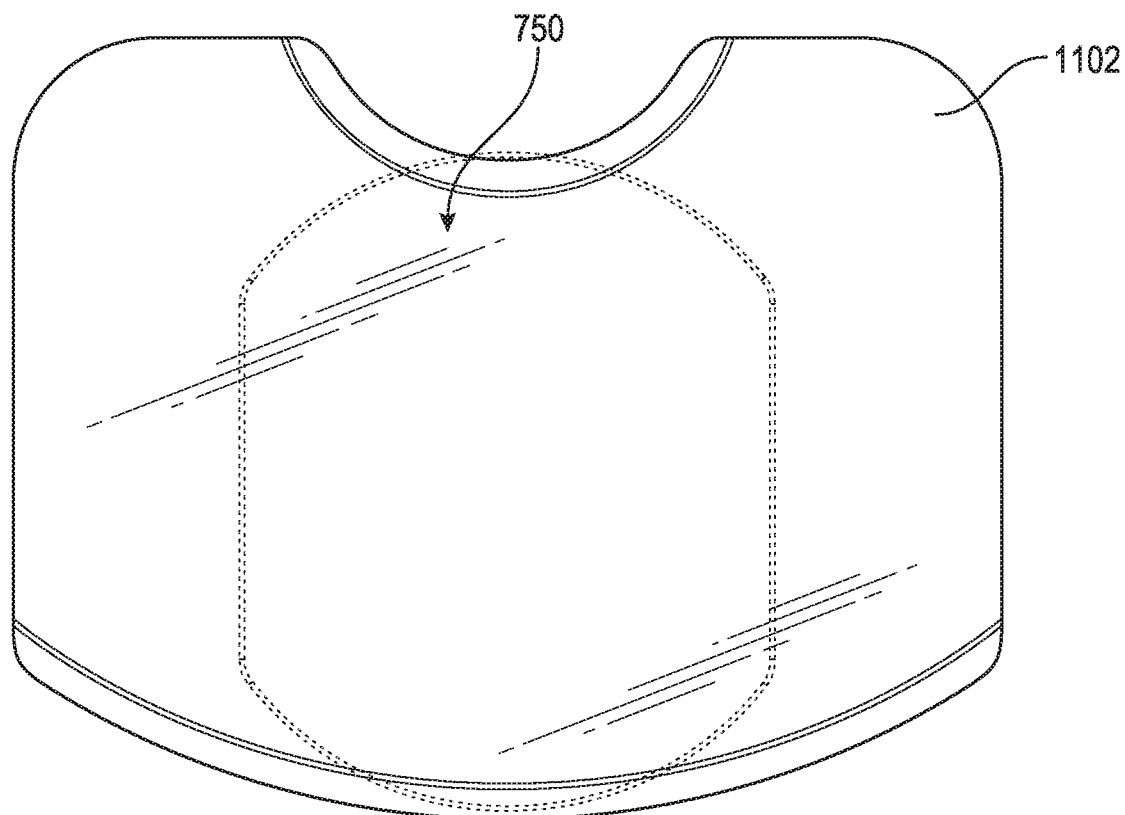

FIG. 5A and FIG. 5B illustrate a portion of the dynamic headset apparatus 100 illustrated in FIGS. 1A-1G according to various arrangements. FIG. 6A and FIG. 6B illustrate transparent views of the dynamic headset apparatus 100 illustrated in FIGS. 1A-1G according to various arrangements.

In some arrangements, the mount 150 is affixed to the restraint system 120 (e.g., the foundation 121), the attachment mechanism 140, and the cradle 110. In some arrangements, one or more of the restraint system 120, the attachment mechanism 140, and the cradle 110 are attached to the mount 150 via a plurality of screws and/or bolts. In other arrangements, one or more of the restraint system 120, the attachment mechanism 140, and the cradle 110 are attached to the mount by any other suitable connecting means, such as, but not limited to, welding, adhesive, one or more hooks and latches, press fittings, or the like. In some arrangements, one or more of the restraint system 120, the attachment mechanism 140, and the cradle 110 are permanently affixed to the mount 150. In other arrangements, one or more of the restraint system 120, the attachment mechanism 140, and the cradle 110 are releasably attached to the mount 150.

In some arrangements, the mount 150 is rounded at its bottom to allow it to move with a user. For instance, if the user wants to turn their head to the right, the mount 150 enables the system to roll right such that devices of the headset apparatus 100 stay in the same position relative to the user's head. In other words, the device 130 stays in the same position relative to the head even if the user is moving within the dynamic headset apparatus 100.

In some arrangements, the attachment mechanism 140 is coupled to the mount 150 so that movement at the mount 150 results in corresponding movement at the attachment mechanism 140 such that the instrument (including but not limited to, the device 130) also correspondingly moves along with the mount 150 and the attachment mechanism 140. For example, as a head of a subject in the cradle 110 rotates (e.g., leftward, rightward, forward, backward, and so on), the mount 150 (e.g., that is connected or otherwise coupled to the cradle 110), the attachment mechanism 140 (e.g., that is connected or otherwise coupled to the mount 150), and the device 130 (e.g., that is connected or otherwise coupled to the attachment mechanism 140) also rotate in an equal amount or a substantially equal amount of rotation as the head of the subject. As such, in some arrangements, the instrument, including the device 130 (e.g., the probe 131 of the device 130), that is located at a certain position with respect to the head of the subject when the head of the subject is in a first position (e.g., a position in which the head of the subject is facing straight upwards, before the rotation) will be located in that same position with respect to the head of the subject after the head of the subject moves (e.g., rotates) to a second position (e.g., a position in which the head of the subject is facing off center from straight upwards, after the rotation).

For example, in some arrangements, at the dynamic headset apparatus 100, the head of the subject is in the first position and the instrument (e.g., the probe 131) is located at a temple of the head of the subject, and when the head of the subject moves (e.g., rotates) to the second position, the instrument (e.g., the probe 131) will still be located at the temple of the head of the subject. In other words, in some arrangements, the head of the subject in the first position and the device 130 (e.g., the probe 131) are aligned along a first plane (e.g., a plane that is parallel to the surface on which the headset apparatus is placed), and when the head of the subject moves (e.g., rotates) to the second position, the device 130 and the head of the subject will still be aligned but on a second plane different from the first plane. For example, the first plane may be different from the second plane by an amount of degree of rotation (e.g., 5 degrees, 10 degrees, and so on).

In some arrangements, the mount 150 is configured to be placed atop a base such that the mount 150 and the base move or pivot relative to each other to allow particular movements of a subject's head within the headset apparatus 100. In some arrangements, the addition of the base provides added stability. Further details pertaining to bases are described below.

In some arrangements, the mount 150 is made from any suitable rigid material, such as, but not limited to, hard plastic, metals, aluminum, steel, titanium, magnesium, various alloys, rigid plastics, composites, carbon fiber, fiber glass, expanded foam, compression molded foam, stereolithography (SLA) or Fused Deposition Modeling (FDM)-made materials, Reaction Injection Molding (RIM) molding, acrylonitrile butadiene styrene (ABS), thermoplastic olefin (TPO), nylon, polyvinyl chloride (PVC), fiber reinforced resins, or the like.

FIG. 7A, FIG. 7B, FIG. 7C, FIG. 7D, FIG. 7E, and FIG. 7F illustrate various views of a dynamic headset apparatus 700 including a device 730 coupled thereto according to various arrangements. FIG. 8A, FIG. 8B, FIG. 8C, FIG. 8D, FIG. 8E, FIG. 8F, and FIG. 8G illustrate various views of the dynamic headset apparatus 700 illustrated in FIGS. 7A-7F, without the coupled device 730, according to various arrangements.

In some arrangements, the headset apparatus 700 includes a cradle 710, a restraint system 720, the device 730, an attachment mechanism 740, and a mount 750. In some arrangements, the restraint system 720 includes a foundation 721, a body 722, and a contact 723. In some arrangements, the device 730 includes a transducer or a probe 731, robotics 732, and one or more cameras 733. The cameras 733 are configured to perform registration on a subject's head to automatically determine boundaries of travel for the probe 731 during operation of the device 730.

FIG. 9A, FIG. 9B, FIG. 9C, and FIG. 9D illustrate a portion of the dynamic headset apparatus 700 illustrated in FIGS. 7A-7F according to various arrangements. In some arrangements, the central portion 740a of the attachment mechanism 740 is configured to be positioned within a recessed portion 750a of the mount 750. In some arrangements, a length of the recessed portion 750a is longer than a length of the central portion 740a of the attachment mechanism 740 such that the attachment mechanism 740 is capable of sliding along the length of the recessed portion 750a. Accordingly, because the attachment mechanism 740 and the mount 750 are slidably attached to each other, the cradle 710 (e.g., that is attached to the central portion 740a of the attachment mechanism 740) can be adjusted to optimally position various subject heads such that the heads are not angled too far forward (e.g., a subject's chin towards the subject's chest) or too far backward (e.g., a subject's chin away from the subject's chest). In some arrangements, the attachment mechanism 740 and the mount 750 are included in the headset apparatus 100 or the attachment mechanism 140 and the mount 150 are included in the headset apparatus 700.

FIG. 10A, FIG. 10B, FIG. 10C, and FIG. 10D illustrate a rotation base 1002 contacting the dynamic headset apparatus 700 illustrated in FIGS. 7A-7F according to various arrangements. In some arrangements, the rotation base 1002 includes a concave recess at the center of the rotation base 1002 for receiving the mount 750. In some arrangements, the concave rotation base 1002 receives the convex mount 750 such that the mount 750 is capable of movement along one or more axes within the rotation base 1002. For example, while a subject's head is inside the headset apparatus 700, the subject is at least capable of shaking his head side to side (e.g., rotation about an axis along the length of the subject's neck) and capable of nodding his head forward and backward (e.g., rotation about an axis perpendicular to the length of the subject's neck). In particular arrangements, as the head of the subject nods forward and backward or shakes from side to side, the mount 750 slides within the base 1002 to allow the subject some freedom of movement while maintaining alignment between the device 730 and the head of the subject.

In some arrangements, materials of the mount 750 and the rotation base 1002 can be selected to inhibit or enhance slidable movement therebetween. For example, the rotation base 1002 and the mount 750 can both be made from nylon, or the mount 750 can be made from polished aluminum and the base 1002 from nylon, to enhance slidable movement between the mount 750 and the rotation base 1002. In some arrangements, one or both of the contacting surfaces of the mount 750 and/or the rotation base 1002 are textured to inhibit slidable movement between the mount 750 and the rotation base 1002.

FIG. 11A, FIG. 11B, FIG. 11C, and FIG. 11D illustrate a slide base 1102 contacting the dynamic headset apparatus 700 illustrated in FIGS. 7A-7F according to various arrangements. In some arrangements, the rotation base 1002 includes a concave recess along the length of the slide base 1102 for receiving the mount 750. Accordingly, the slide base 1102 provides one or more axes of rotation (e.g., similar as those provided by the rotation base 1002), and further provides an axis of rotation that allows a subject's head to slide along the length of the slide base 1102 (e.g., by rotating the head in a motion arcing from one shoulder to another shoulder of the subject). The materials used for the rotation base 1002 can be implemented as materials used for the slide base 1102.

Figure 12A:
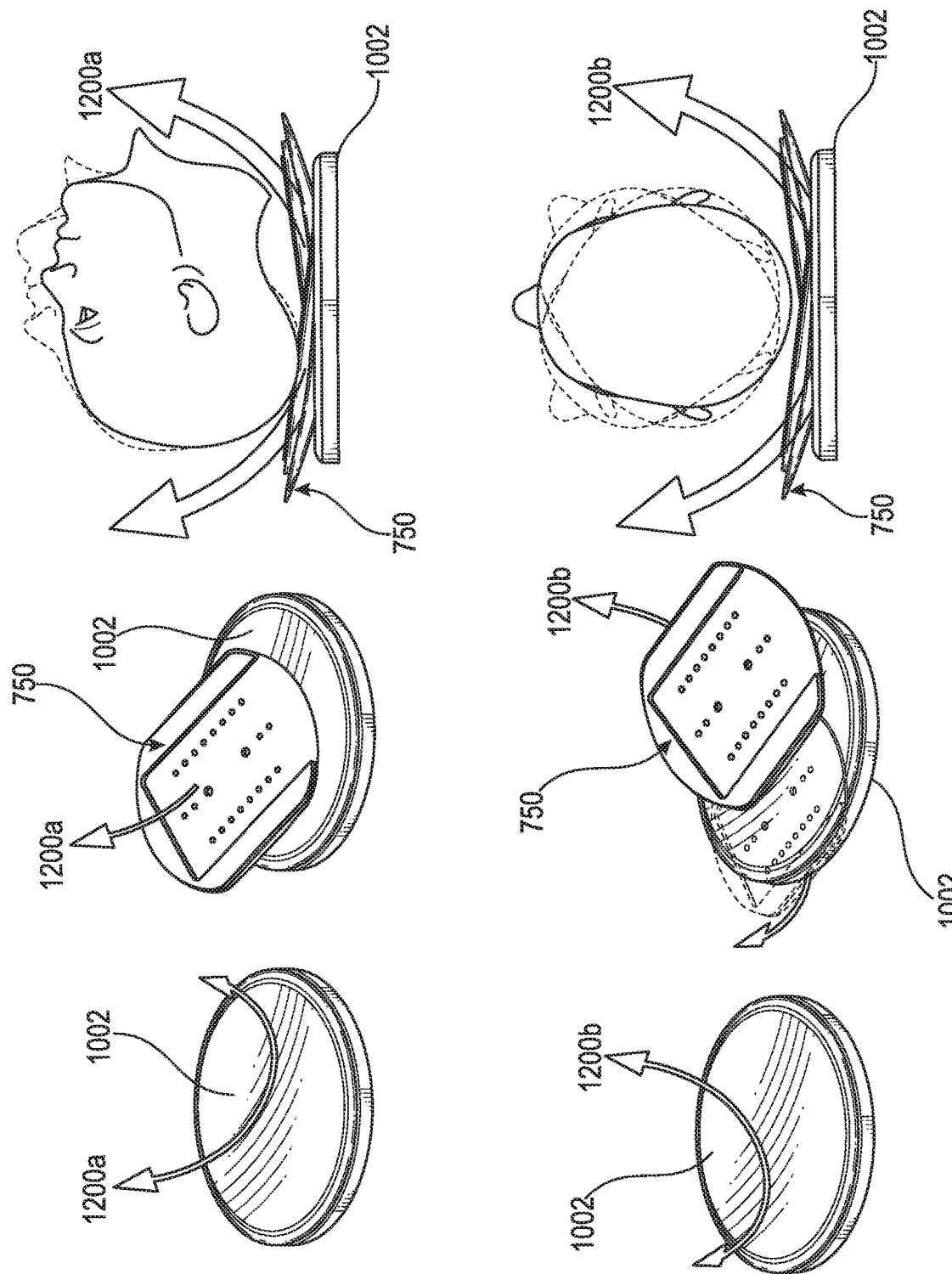
FIG. 12A illustrates movement of a dynamic headset within the rotation base illustrated in FIGS. 10A-10D according to various arrangements.

FIG. 12A illustrates movement of the dynamic headset apparatus 700 within the rotation base 1002 illustrated in FIGS. 10A-10D according to various arrangements. As discussed above, in some arrangements, the dynamic headset apparatus 700 including the mount 750 that is in contact with the rotation base 1002 is capable of movement (e.g., rotation) along one or more axes. For example, the first axis of rotation can be through a central location where the mount 750 contacts the rotation base 1002 such that movement of the headset apparatus 700 follows a first path of movement 1200a. In addition, the second axis can be perpendicular to the first axis and allow for movement of the headset apparatus 700 to follow a second path of movement 1200b. In some arrangements, other axes and paths of movement are enabled by the rotation base 1002, such as many different paths (e.g., those similar to the first path 1200a and the second path 1200b but in different orientations or turned at various degrees from the first path 1200a and the second path 1200b) that allow the mount 750 to slide within the rotation base 1002. For example, in addition to the first path 1200a and the second path 1200b, the mount 750 can move along a path that is anywhere between the first path 1200a and the second path 1200b.

Figure 12B:
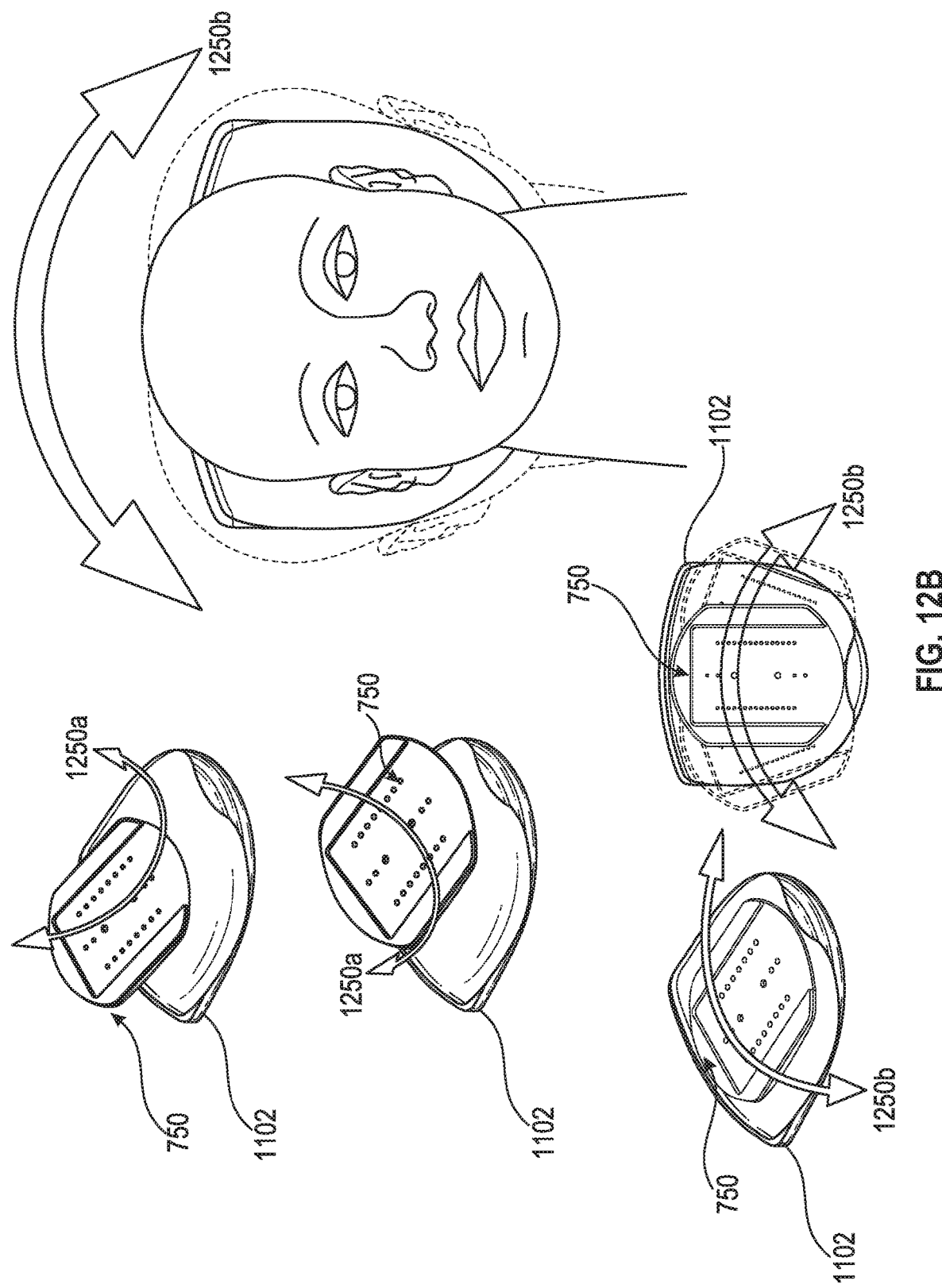
FIG. 12B illustrates movement of a dynamic headset within the slide base illustrated in FIGS. 11A-11D according to various arrangements.

FIG. 12B illustrates movement of the dynamic headset apparatus 700 within the slide base 1102 illustrated in FIGS. 11A-11D according to various arrangements. In some arrangements, the slide base 1102 allows the headset apparatus 700 to move about one or more axes of rotation that are provided for by the rotation base 1002. For example, the slide base 1102 allows the headset apparatus 700 to travel along a first path of movement 1250a (e.g., similar to the first path of movement 1200a). Furthermore, the slide base 1102 allows the headset apparatus 700 to travel along the length of the slide base 1102 such that the headset apparatus 700 is capable of following a second path of movement 1250b. In some arrangements, the slide base 1102 allows the mount 750 (and therefore the headset apparatus 700) to at least allow a head of a subject to nod forward and backward along the first path of movement 1250a and to turn in an arcing motion along the second path of movement 1250b.

In some arrangements, other bases utilized in connection with the mount 750 can be used to provide different paths of motion for a head of a subject or to restrict movement of the head of the subject in certain directions. For example, in some arrangements, a base can allow vertical motion of the head of the subject (e.g., such that the head slides upward towards the restraint system 720 and downward towards the body of the subject). In some arrangements, a base provides rotational movement of the mount 750 but not sliding movement. In some arrangements, bases provide for controlled paths of movement of the headset apparatus 100 and 700 while also providing stability at the mount 150 and 750, as the bases are interposed between the mount 150 and 750 and the surface on which the headset apparatus 100 and 700 and the base lie. In some arrangements, a base is not utilized and the mount 150 and 750 is placed directly on top of the surface on which the headset apparatus 100 and 700 lie. In some arrangements, motion of the headset apparatus 100 and 700 without the use of a base can be illustrated with reference to FIGS. 13A and 13B.

In some arrangements, the mount 150 and 750 have different shapes such that the bases have different corresponding shapes to fit the shapes of the mount 150 and 750. For example, the mount 150 and 750 can have a convex rectangular shape such that the bases have a corresponding concave rectangular shape for allowing slidable movement of the mount 150 and 750 within the base as described above. As another example, the mount 150 and 750 can have a convex pyramid shape having a protruding point that can be received in a base having a corresponding concave shape. In other arrangements, the mount 150 and 750 have any other suitable shape for allowing sliding and/or rotational movement within the bases.

Figure 13A:
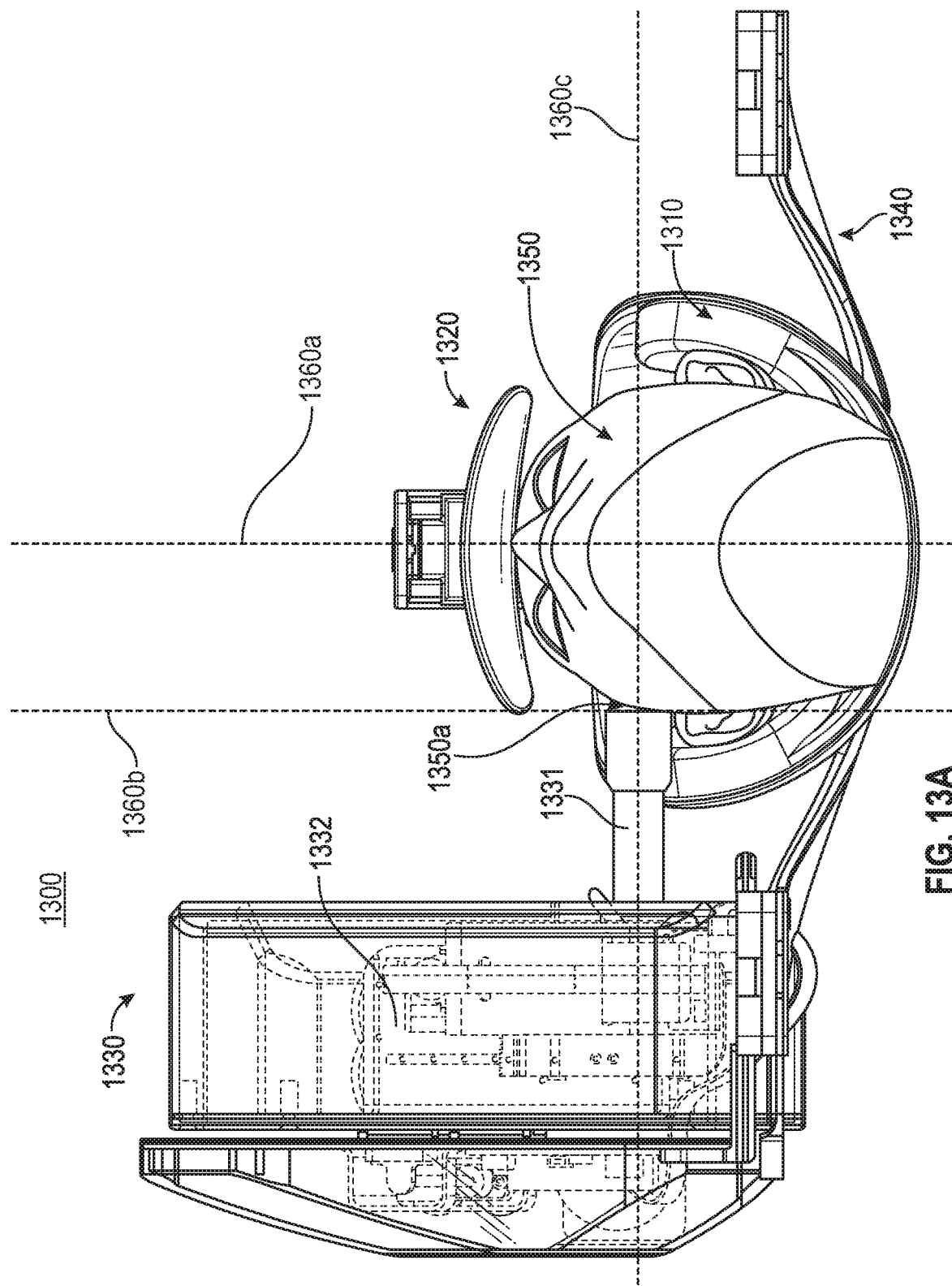
FIG. 13A illustrates a front view of a dynamic headset apparatus and a head of a subject therein according to various arrangements.

FIG. 13A illustrates a front view of a dynamic headset apparatus 1300 and a head 1350 of a subject therein according to various arrangements.

In some arrangements, the headset apparatus 1300 includes a cradle 1310, a restraint system 1320, a device 1330, and one or more attachment mechanisms 1340 that are attached to the head cradle 1310. In some arrangements, the device 1330 includes a transducer or a probe 1331 and robotics 1332. In some arrangements, the elements 1300, 1310, 1320, 1330, 1340, 1331, and 1332 incorporate description from similarly labelled elements as disclosed above. As shown in FIG. 13A, the head 1350 of the subject is facing straight upwards such that the headset apparatus 1300 is level with the platform on which the headset apparatus 1300 is placed. For example, as shown in FIG. 13A, the attachment mechanisms 1340 on both sides of the head cradle 1310 are at substantially the same height from the platform.

In some arrangements, a first reference line 1360a extends through the center of the head 1350 (e.g., through a nose of the head 1350 in a direction extending from the restraint system 1320 and through the center of the head cradle 1310), a second reference line 1360b extends through a location 1350a at which the probe 1331 contacts or is proximate the head 1350, and a third reference line 1360c that extends lengthwise through the probe 1331 towards the head 1350 and through the location 1350a at which the probe 1331 contacts or is proximate the head 1350. The first reference line 1360a and the second reference line 1360b extend substantially parallel to each other and the third reference line 1360c extends substantially perpendicular to each of the first reference line 1360a and the second reference line 1360b. As shown in FIG. 13A, when the head 1350 is facing substantially upward in a default state, the third reference line 1360c is substantially parallel to the platform on which the headset apparatus 1300 is placed, while the first reference line 1360a and the second reference line 1360b are substantially perpendicular to the platform on which the headset apparatus 1300 lies.

FIG. 13B illustrates a front view of the dynamic headset apparatus 1300 and the head 1350 of the subject therein as illustrated in FIG. 13A after an amount of rotation of the head 1350 of the subject according to various arrangements.

In some arrangements, the head cradle 1310 directly contacts the platform on which the headset apparatus 1300 lies. In other words, in some arrangements, the headset apparatus 1300 does not include a mount under the head cradle 1310 as described in other arrangements herein. In some arrangements, the head cradle 1310 has a convex or rounded bottom surface that contacts the platform. Accordingly, in some arrangements, the bottom surface of the head cradle 1310 allows rotation of the headset apparatus 1300 such that the head 1350 of the subject can twist his or her head 1350 within the head cradle 1310 and such that the entire headset apparatus 1300 rotates along with the head 1350 that lies within the head cradle 1310. Accordingly, because the headset apparatus 1300 rotates along with the rotation of the head 1350, the location 1350a at which the probe 1331 contacts or is proximate the head 1350 is the same location before and after the rotation by the head 1350 of the subject.

As shown in FIG. 13B, the head 1350 deviates from its upward-facing default position and rotates away from the device 1330. For example, the head 1350 of the subject may rotate to his or her left at the neck while resting within the head cradle 1310. In some arrangements, after the rotation of the head 1350 within the head cradle 1310, the first reference line 1360a rotates from that shown in FIG. 13A corresponding to the amount of rotation of the head 1350 of the subject. In addition, in some arrangements, because the entire headset apparatus 1300 rotates along with the head 1350, the second reference line 1360b also rotates from that shown in FIG. 13A corresponding to the amount of rotation of the head 1350 of the subject. In other words, in some arrangements, after rotation of the head 1350, the first reference line 1360a and the second reference line 1360b rotate a substantially same amount such that the first reference line 1360a and the second reference line 1360b remain substantially parallel. In addition, in some arrangements, the third reference line 1360c also rotates from that shown in FIG. 13A corresponding to the amount of rotation of the head 1350 of the subject and corresponding to the amount of rotation of the first reference line 1360a and the second reference line 1360b such that the third reference line 1360c remains substantially perpendicular to the first reference line 1360a and the second reference line 1360b.

Accordingly, in some arrangements, because of the above-described motion of the headset apparatus 1300 in response to a given amount of rotation of the head 1350 of the subject within the head cradle 1310, the location 1350a at which the probe 1331 contacts or is proximate the head 1350 is the same or substantially the same before (e.g., FIG. 13A) and after (e.g., FIG. 13B) the rotation of the head 1350 of the subject. Although the FIG. 13A and FIG. 13B illustrate lateral rotation, in some arrangements, other rotational motion of the head 1350 can still result in the location 1350a, at which the probe 1331 contacts or is proximate the head 1350, remaining stable (or consistent or locked or fixed) before and after the rotational motion, such as, but not limited to, forward and backward rotational movement (e.g., nodding of the head 1350), diagonal rotational movement, and so on.

In addition, in some arrangements, the headset apparatus 1300 provides for the axis of rotation of the head 1350 to be the same as the axis of rotation of the headset apparatus 1300 and components (e.g., the instrument as described herein) thereof. For example, as the head 1350 of the subject twists to his or her left as shown in FIG. 13B, the axis of rotation of the head 1350 is along a length of the neck of the subject, and similarly, the axis of rotation of, for example, the probe 1331 is also along the length of the neck (e.g., the same axis of rotation as that of the head 1350). In additional arrangements, other rotational movements of the head 1350 (e.g., forward and backward rotation or nodding of the head 1350) will result in similar rotational movements of the headset apparatus 1300 and components thereof such that the axis of the rotation of the head 1350 will be the same as the axis of rotation of the headset apparatus 1300 and components thereof.

Although FIG. 13A and FIG. 13B illustrate the headset apparatus 1300 without a mount, other arrangements including a mount described herein (e.g., headset apparatuses 100 and 700) can exhibit similar movements. For example, in some arrangements, the mount (e.g., mount 150 or 750) that is convex or rounded can allow rotation of the headset apparatus in response to rotation of a subject's head in a similar fashion as the headset apparatus 1300 does and as described above. Furthermore, in some arrangements, when a headset apparatus is used in conjunction with a base (e.g., bases 1002 or 1102), further paths of movement of the head of the subject are available such that the location 1350a at which the probe 1331 contacts or is proximate the head 1350 remains stable (or consistent or locked or fixed) before and after the permitted movement of the head 1350 (e.g., those movements illustrated in FIGS. 12A and 12B).

In some arrangements, the headset apparatuses described herein are used in conjunction with a surface on which the headset apparatuses are placed (e.g., either directly or with a base interposed therebetween). For example, the surface can include a bed (e.g., a gurney) such that the subject can lay down into the headset apparatus such that the subject's head is horizontal (e.g., the subject is in a supine position). Accordingly, in some arrangements, the subject's head is not burdened with the weight of the headset, as the weight of the device mounted to the headset, and the other components of the headset apparatus, is supported by, for example, the mount, the base that receives the mount, and the platform or surface on which the headset is placed (e.g., a bed or gurney). Accordingly, in some arrangements, the headset is capable of moving along with head movements of a subject while the subject's head is not actually supporting the weight of the headset. In particular arrangements, the subject's head does not support any of the weight of the headset, as the mount, the base, and the platform supports the total weight of the headset, including any device attached thereto.

Although different arrangements of a dynamic headset apparatus are described herein, any one or more features of one arrangement can be incorporated into another arrangement and features of any two or more arrangements can be combined as desired. For example, one or more features of the headset apparatus 100 can be incorporated into the headset apparatus 700, and vice versa. Furthermore, in some arrangements, although the mount 750 of the headset apparatus 700 is illustrated as being used in conjunction with the bases 1002 and 1102, the mount 150 of the headset apparatus 100 or any other mount described herein can also be used in conjunction with the bases 1002 and 1102.

In other arrangements, the headset apparatuses described herein are positioned such that a subject is in a seated position, and the subject's head is vertical. In particular arrangements, the headset apparatus is mounted to a vertical platform or surface such that the subject's head bears little or no weight of the headset apparatus. For example, the vertical headset can be mounted to a wall, a chair, and the like. The above used terms, including "held fast," "mount," "attached," "coupled," "affixed," "connected," "secured," and the like are used interchangeably. In addition, while certain arrangements have been described to include a first element as being "coupled" (or "attached," "connected," "fastened," etc.) to a second element, the first element may be directly coupled to the second element or may be indirectly coupled to the second element via a third element.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. All structural and functional equivalents to the elements of the various aspects described throughout the previous description that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed as a means plus function unless the element is expressly recited using the phrase "means for."

It is understood that the specific order or hierarchy of steps in the processes disclosed is an example of illustrative approaches. Based upon design preferences, it is understood that the specific order or hierarchy of steps in the processes may be rearranged while remaining within the scope of the previous description. The accompanying method claims present elements of the various steps in a sample order, and are not meant to be limited to the specific order or hierarchy presented.

The previous description of the disclosed implementations is provided to enable any person skilled in the art to make or use the disclosed subject matter. Various modifications to these implementations will be readily apparent to those skilled in the art, and the generic principles defined herein may be applied to other implementations without departing from the spirit or scope of the previous description. Thus, the previous description is not intended to be limited to the implementations shown herein but is to be accorded the widest scope consistent with the principles and novel features disclosed herein.

Although discrete examples and arrangements are illustrated and described herein, any given arrangement, feature, component, design, and the like of the given arrangement, can be incorporated into another given arrangement described herein.

The various examples illustrated and described are provided merely as examples to illustrate various features of the claims. However, features shown and described with respect to any given example are not necessarily limited to the associated example and may be used or combined with other examples that are shown and described. Further, the claims are not intended to be limited by any one example.

What is claimed is:

1. A dynamic headset apparatus comprising:
   a head cradle having a top surface and a bottom surface opposite the top surface, wherein the top surface is configured to receive a head of a subject and the bottom surface has a convex shape and is configured to face a platform on which the dynamic headset apparatus is placed; and
   a device comprising an instrument configured to transmit or receive acoustic energy with respect to the head of the subject and be adjacent to the head of the subject when the head of the subject is in the head cradle.

2. The dynamic headset apparatus of claim 1, wherein an amount of rotation of the head of the subject in the head cradle is configured to result in a same amount of rotation at the instrument.

3. The dynamic headset apparatus of claim 2, wherein the rotation of the head of the subject and the rotation of the instrument are configured to be about a same axis.

4. The dynamic headset apparatus of claim 2, wherein the head cradle is shaped such that the instrument is configured to be adjacent to a same location at the head of the subject before and after the rotation of the head of the subject.

5. The dynamic headset apparatus of claim 1, wherein the convex bottom surface of the head cradle has a rounded shape.

6. The dynamic headset apparatus of claim 1, wherein the head cradle contacts the platform on which the dynamic headset apparatus is placed.

7. The dynamic headset apparatus of claim 1, further comprising a mount under the head cradle, wherein the convex bottom surface is configured to face a platform on which the dynamic headset apparatus is placed.

8. The dynamic headset apparatus of claim 7, wherein the mount is attached to the head cradle.

9. The dynamic headset apparatus of claim 7, wherein the dynamic headset apparatus further comprises a base having a cavity configured to receive the convex bottom surface of the mount.

10. The dynamic headset apparatus of claim 9, wherein the base is configured to be interposed between the mount and the platform on which the dynamic headset apparatus is placed.

11. The dynamic headset apparatus of claim 9, wherein the cavity of the base has a larger area than that of the convex bottom surface of the mount such that the cavity defines one or more paths of movement for the mount within the cavity.

12. The dynamic headset apparatus of claim 9, wherein the cavity has a concave inner surface for receiving the convex bottom surface of the mount.

13. The dynamic headset apparatus of claim 12, wherein the concave inner surface of the cavity and the convex bottom surface of the mount are rounded.

14. The dynamic headset apparatus of claim 9, wherein the base is releasably attached to the mount.

15. The dynamic headset apparatus of claim 7, wherein the mount is shaped such that an amount of rotation of the head of the subject in the head cradle is configured to result in the same amount of rotation at the instrument.

16. The dynamic headset apparatus of claim 15, wherein the mount is shaped such that the instrument is configured to be adjacent to a same location at the head of the subject before and after the amount of rotation of the head of the subject.

17. The dynamic headset apparatus of claim 7, wherein the convex bottom surface of the mount has a round shape.

18. The dynamic headset apparatus of claim 1, wherein the instrument is configured to be located proximate to or in contact with a temporal window of the head of the subject.

19. The dynamic headset apparatus of claim 1, wherein the acoustic energy comprises ultrasound.

20. The dynamic headset apparatus of claim 1, further comprising a device attachment mechanism extending from the head cradle, wherein the device is releasably attached to the device attachment mechanism.

21. The dynamic headset apparatus of claim 1, wherein the head cradle is configured to receive a back portion of the head of the subject such that the subject is in a supine position when the head of the subject is in the head cradle.

22. A dynamic headset apparatus comprising:
    a head cradle configured to receive a head of a subject and having a bottom surface configured to face a platform on which the dynamic headset apparatus is placed;
    a device comprising an instrument configured to be adjacent to the head of the subject when the head of the subject is in the head cradle;
    a mount under the head cradle and having a convex bottom surface configured to face a platform on which the dynamic headset apparatus is placed; and
    a base having a cavity configured to receive the convex bottom surface of the mount wherein the cavity of the base has a larger area than that of the convex bottom surface of the mount such that the cavity defines a rotational path of movement and a sliding path of movement of the mount within the cavity.

23. The dynamic headset apparatus of claim 22, wherein the cavity has a circular shape and the rotational path of movement and the sliding path of movement are in any direction from a center of the cavity.

24. The dynamic headset apparatus of claim 22, wherein the cavity has an elongated arc shape and the sliding path of movement is along the elongated arc shape.

25. The dynamic headset apparatus of claim 22, wherein the rotational path of movement and the sliding path of movement are in a same direction.

26. A method of manufacturing a dynamic headset apparatus, the method comprising:
    providing a head cradle having a top surface and a bottom surface opposite the top surface, wherein the top surface is configured to receive a head of a subject and the bottom surface has a convex shape and is configured to face a platform on which the dynamic headset apparatus is placed; and
    providing a device comprising an instrument configured to transmit or receive acoustic energy with respect to the head of the subject and be adjacent to the head of the subject when the head of the subject is in the head cradle.

* * * * *